(12) United States Patent
Hoffmann et al.

(10) Patent No.: US 9,040,554 B2
(45) Date of Patent: May 26, 2015

(54) SOLID FORMS OF NEMATOCIDAL SULFONAMIDES

(71) Applicant: E I DU PONT DE NEMOURS AND COMPANY, Wilmington, DE (US)

(72) Inventors: Christian Hoffmann, Newark, DE (US); William J Marshall, Wilmington, DE (US); Rafael Shapiro, Wilmington, DE (US); Richard A Berger, Claymont, DE (US)

(73) Assignee: E I DU PONT DE NEMOURS AND COMPANY, Wilmington, DE (US)

( * ) Notice: Subject to any disclaimer, the term of this patent is extended or adjusted under 35 U.S.C. 154(b) by 0 days.

(21) Appl. No.: 14/346,446

(22) PCT Filed: Oct. 5, 2012

(86) PCT No.: PCT/US2012/058915
§ 371 (c)(1),
(2) Date: Mar. 21, 2014

(87) PCT Pub. No.: WO2013/055584
PCT Pub. Date: Apr. 18, 2013

(65) Prior Publication Data
US 2014/0228393 A1 Aug. 14, 2014

Related U.S. Application Data

(60) Provisional application No. 61/546,660, filed on Oct. 13, 2011.

(51) Int. Cl.
*A01N 43/90* (2006.01)
*C07D 471/04* (2006.01)

(52) U.S. Cl.
CPC .............. *A01N 43/90* (2013.01); *C07D 471/04* (2013.01)

(58) Field of Classification Search
None
See application file for complete search history.

(56) References Cited

U.S. PATENT DOCUMENTS

2012/0034315 A1  2/2012  Hanagan et al.
2012/0114624 A1  5/2012  Lahm et al.

FOREIGN PATENT DOCUMENTS

WO  2010/123791 A1  10/2010
WO  2010/129500 A2  11/2010

OTHER PUBLICATIONS

D. Braga et al., "The Growing World of Crystal Forms" Chem. Commun. 2010, vol. 46, pp. 6232-6242.

*Primary Examiner* — Timothy R Rozof
(74) *Attorney, Agent, or Firm* — Renee M Lett

(57) ABSTRACT

Disclosed are solid forms of 8-chloro-N-[(2-chloro-5-methoxyphenyl)sulfonyl]-6-(trifluoromethyl)-imidazo[1,2-a]pyridine-2-carboxamide (Compound 1). Methods for the preparation of solid forms of Compound 1 and for the conversion of one solid form of Compound 1 into another are disclosed.

Disclosed are nematocidal compositions comprising a nematocidally effective amount of a solid form of Compound 1 and at least one additional component selected from the group consisting of surfactants, solid diluents and liquid carriers. Compositions comprising a mixture of a solid form of Compound 1 and at least one other nematicide, insecticide and/or fungicide are also disclosed.

Also disclosed are methods for protecting a plant from nematodes comprising applying to the plant, or portion, or seed thereof, or to the growing medium of the plant, a nematocidally effective amount of Compound 1 comprising the polymorph Form A.

17 Claims, 1 Drawing Sheet

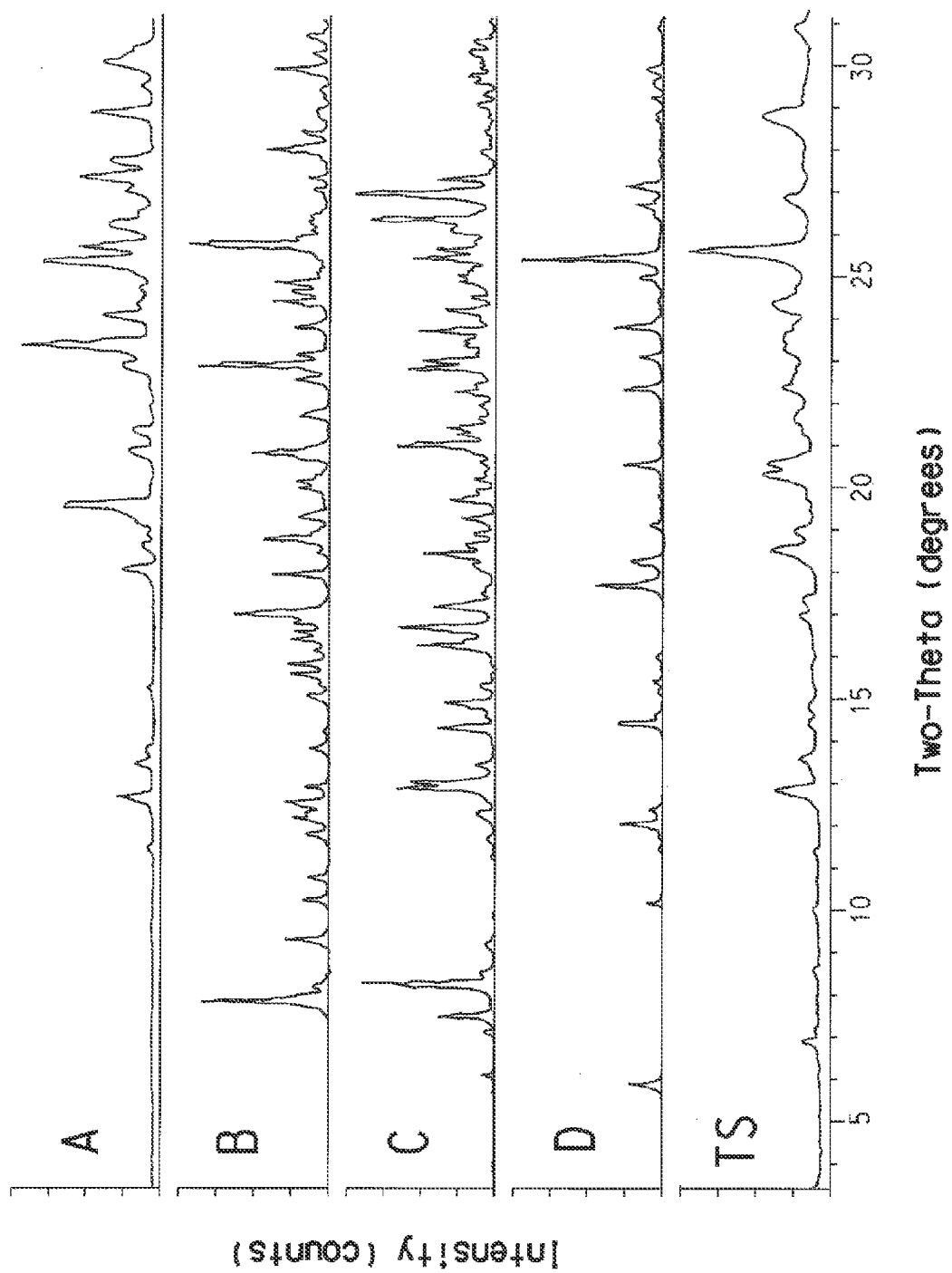

SOLID FORMS OF NEMATOCIDAL SULFONAMIDES

FIELD OF THE INVENTION

This invention relates to solid forms of 8-chloro-N-[(2-chloro-5-methoxyphenyl)sulfonyl]-6-(trifluoromethyl)-imidazo[1,2-a]pyridine-2-carboxamide, their preparation, compositions, and methods of use as nematocides.

BACKGROUND OF THE INVENTION

The solid state of chemical compounds can be amorphous (i.e. no long-range order in the positions of atoms) or crystalline (i.e. atoms arranged in an orderly repeating pattern). The term "polymorph" refers to a particular crystal form (i.e. structure of crystal lattice) of a chemical compound that can exist in more than one crystal form in the solid state. Polymorphs can differ in such chemical and physical (i.e. physiochemical) properties as crystal shape, density, hardness, color, chemical stability, melting point, hygroscopicity, suspensibility, solubility and dissolution rate, and such biological properties as biological availability, biological efficacy and toxicity.

Predicting physiochemical properties such as melting point or solubility for a crystal form in which the solid state of a chemical compound can exist remains impossible. Furthermore, even predicting whether the solid state of a compound may be present in more than one crystal form is not possible.

PCT Patent Publication WO 2010/129500 discloses the nematocidal sulfonamide 8-chloro-N-[(2-chloro-5-methoxyphenyl)sulfonyl]-6-(trifluoromethyl)-imidazo[1,2-a]-pyridine-2-carboxamide and methods for its preparation, as well as the utility of this compound as a nematocide. New solid forms of this compound, their compositions and methods of their preparation and use have now been discovered.

SUMMARY OF THE INVENTION

This invention relates to solid forms of 8-chloro-N-[(2-chloro-5-methoxyphenyl)sulfonyl]-6-(trifluoromethyl)-imidazo[1,2-a]pyridine-2-carboxamide (Compound 1). More particularly, this invention is directed to a polymorph of Compound 1 designated Form A characterized by a powder X-ray diffraction pattern having at least the 2θ reflection positions 30.367, 29.131, 27.995, 27.611, 26.49, 25.973, 25.604, 24.285, 23.582 and 19.789 degrees.

This invention also relates to methods for the direct preparation of various solid forms of Compound 1 (i.e. not starting with other solid forms of Compound 1). More particularly, this invention is directed to a method for preparing a desired polymorph of Compound 1 comprising: forming a reaction mixture by contacting 2-chloro-5-methoxybenzene sulfonamide and 8-chloro-6-trifluoromethyl-imidazo[1,2-a]pyridine-2-carbonyl chloride in the presence of a first solvent to form a solid form of Compound 1 and then mixing the solid form of Compound 1 with a second solvent to convert the solid form to the polymorph Form A. This invention also relates to methods for the conversion of one solid form of Compound 1 into another. More particularly, this invention is directed to a method for preparing a polymorph of Compound 1 designated Form A, the method comprising: forming a slurry with a solvent of one or more solid forms of Compound 1 selected from the group of forms B, C, D, solvates, amorphous forms and mixtures thereof with Form A and maintaining the slurry while the solid forms of Compound 1 convert to polymorph Form A.

This invention also relates to compounds used in the method for preparation of Compound 1 (i.e. 2-chloro-5-methoxybenzene sulfonamide and 8-chloro-6-trifluoromethyl-imidazo[1,2-a]pyridine-2-carbonyl chloride).

This invention also relates to a nematocidal composition comprising (a) polymorph Form A of Compound 1; and (b) at least one additional component selected from the group consisting of surfactants, solid diluents and liquid carriers.

This invention also relates to a nematocidal composition comprising (a) polymorph Form A of Compound 1; and (b) at least one other nematocide, insecticide and/or fungicide.

This invention further relates to a method protecting a plant from nematodes comprising applying to the plant, or portion, or seed thereof, or to the growing medium of the plant, a nematocidally effective amount of Compound 1 comprising the polymorph Form A.

BRIEF DESCRIPTION OF THE DRAWINGS

FIG. 1 shows Cu(Kα1)-powder X-ray diffraction patterns of polymorph Forms A, B, C, D and TS of Compound 1 showing absolute X-ray intensity in counts graphed against 2θ reflection positions in degrees.

DETAILED DESCRIPTION OF THE INVENTION

As used herein, the terms "comprises," "comprising," "includes," "including," "has," "having", "contains" or "containing" or any other variation thereof, are intended to cover a non-exclusive inclusion. For example, a composition, process, method, article, or apparatus that comprises a list of elements is not necessarily limited to only those elements but may include other elements not expressly listed or inherent to such composition, process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, the indefinite articles "a" and "an" preceding an element or component of the invention are intended to be nonrestrictive regarding the number of instances (i.e. occurrences) of the element or component. Therefore "a" or "an" should be read to include one or at least one, and the singular word form of the element or component also includes the plural unless the number is obviously meant to be singular.

The word "nematocide" is sometimes given the alternative spelling "nematicide" in the art. A nematocide is a compound used to control (including prevention, reduction or elimination) parasitic nematodes.

As used to in the present disclosure and claims, the term "nematode" refers to a living organism of the Phylum Nematoda. As generally defined, a "parasite" lives or grows inside or feeds on another living organism (such as a plant) described as the "host". As referred to in the present disclosure and claims a "parasitic nematode" is particularly a nematode that injures or damages tissue or causes other forms of disease in plants.

An "infestation" refers to the presence of nematodes in numbers that pose a risk to plants. The presence can be in the environment, e.g., on an agricultural crop or other type of plant.

As referred to in the present disclosure and claims, the terms "parasiticidal" and "parasiticidally" refers to observable effects on a parasitic nematode to provide protection of a plant from the nematode. Parasiticidal effects typically relate to diminishing the occurrence or activity of the target parasitic nematode. Such effects on the nematode include necrosis, death, retarded growth, diminished mobility or lessened ability to remain on or in the host plant, reduced feeding and inhibition of reproduction. These effects on parasitic nematodes provide control (including prevention, reduction or elimination) of parasitic infestation of the plant. Therefore "control" of a parasitic nematode means achieving a parasiticidal effect on the nematode. The expressions "parasiticidally effective amount" and "biologically effective amount" in the context of applying a chemical compound to control a parasitic nematode refer an amount of the compound that is sufficient to control the parasitic nematode.

The term "agronomic" refers to the production of field crops such as for food and fiber and includes the growth of soybeans and other legumes, cereal (e.g., wheat, oats, barley, rye, rice, maize/corn), leafy vegetables (e.g., lettuce, cabbage, and other cole crops), fruiting vegetables (e.g., tomatoes, pepper, eggplant, crucifers and cucurbits), potatoes, sweet potatoes, grapes, cotton, tree fruits (e.g., pome, stone and citrus), small fruit (berries, cherries) and other specialty crops (e.g., canola, sunflower, olives).

The term "nonagronomic" refers to other than field crops, such as horticultural crops (e.g., greenhouse, nursery or ornamental plants not grown in a field), turf (e.g., sod farm, pasture, golf course, lawn, sports field, etc.), agro-forestry and vegetation management.

As referred to in the present disclosure and claims, "plant" includes members of Kingdom Plantae, particularly seed plants (Spermatopsida), at all life stages, including young plants (e.g., germinating seeds developing into seedlings) and mature, reproductive stages (e.g., plants producing flowers and seeds). Portions of plants include geotropic members typically growing beneath the surface of the growing medium such as roots, tubers, bulbs and corms, and also members growing above the growing medium, such as foliage (including stems and leaves), flowers, fruits and seeds. Growing mediums include soil, liquid nutrent mediums, gel nutrent mediums or soil mixes with peat, bark, saw dust, sand, pumice, perlite, vermiculite and other similar products. As referred to herein, the term "seedling", used either alone or in a combination of words means a young plant developing from the embryo of a seed.

The term "water-miscible" in the context of "water-miscible solvent" means a liquid solvent (including mixtures of solvent compounds) that is completely soluble in water (and water soluble in the solvent) in all proportions at the temperature of the (e.g., reaction) medium comprising the water-miscible solvent. Methanol, ethanol, acetone and acetonitrile are examples of water-miscible solvents.

Conversely, the term "water-immiscible" in the context of a substance that is a "water-immiscible organic compound", "water-immiscible liquid component" or "water-immiscible liquid carrier" denotes that the substance is not soluble in water (and water soluble in the substance) in all proportions at relevant temperatures (for formulated compositions around room temperature). Typically water-immiscible substances used as liquid carriers or other liquid components in formulated compositions have little water solubility and water has little solubility in the water-immiscible substances. Often water-immiscible substances used in formulation are soluble in water in an extent of less than about 1%, or less than about 0.1%, or even less than about 0.01% by weight at about 20° C.

The expression "continuous liquid phase" in the context of liquid formulated compositions refers to the liquid phase formed by the liquid carrier. The continuous liquid phase provides the bulk liquid medium in which other formulating components are dissolved, dispersed (as solid particulates) or emulsified (as liquid droplets). When the liquid carrier is aqueous (water optionally containing dissolved water-soluble compounds), a liquid emulsified in the aqueous liquid carrier is formed by a water-immiscible liquid component.

The term "room temperature" as used in this disclosure refers to a temperature between about 18° C. and about 26° C.

The term "polymorph" refers to a particular crystal form (i.e. structure of crystal lattice) of a chemical compound that can exist in more than one crystal form in the solid state.

Embodiments of the present invention include:

Embodiment 1

The polymorph of 8-chloro-N-[(2-chloro-5-methoxyphenyl)sulfonyl]-6-(trifluoromethyl)-imidazo[1,2-a]pyridine-2-carboxamide (Compound 1) designated Form A in the Summary of the Invention and characterized by a room-temperature powder Cu(Kα1) X-ray diffraction pattern having at least the 2θ reflection positions

| 2θ |
|---|
| 30.367 |
| 29.131 |
| 27.995 |
| 27.611 |
| 26.49 |
| 25.973 |
| 25.604 |
| 24.285 |
| 23.582 |
| 19.789 |

Embodiment 2

The polymorph of 8-chloro-N-[(2-chloro-5-methoxyphenyl)sulfonyl]-6-(trifluoromethyl)-imidazo[1,2-a]pyridine-2-carboxamide (Compound 1) designated Form B in the Summary of the Invention and characterized by a −100° C. simulated Cu(Kα1) X-ray diffraction pattern having at least the 2θ reflection positions

| 2θ |
|---|
| 28.242 |
| 25.978 |
| 25.06 |
| 24.583 |
| 23.082 |
| 20.999 |
| 18.981 |
| 18.12 |
| 17.219 |
| 7.998 |

Embodiment 3

The polymorph of 8-chloro-N-[(2-chloro-5-methoxyphenyl)sulfonyl]-6-(trifluoromethyl)-imidazo[1,2-a]pyridine-2-carboxamide (Compound 1) designated Form D in the Summary of the Invention and characterized by a −100° C. simulated Cu(Kα1) X-ray diffraction pattern having at least the 2θ reflection positions

| 2θ |
|---|
| 27.323 |
| 25.581 |
| 23.958 |
| 22.459 |
| 20.68 |
| 18.398 |
| 17.821 |
| 14.558 |
| 12.182 |
| 5.943 |

Embodiment 4

The polymorph of 8-chloro-N-[(2-chloro-5-methoxyphenyl)sulfonyl]-6-(trifluoromethyl)-imidazo[1,2-a]pyridine-2-carboxamide (Compound 1) designated Form TS in the Summary of the Invention and characterized by a room-temperature powder Cu(Kα1) X-ray diffraction pattern having at least the 2θ reflection positions

| 2θ |
|---|
| 28.913 |
| 26.942 |
| 25.672 |
| 24.451 |
| 23.316 |
| 22.429 |
| 20.325 |
| 19.053 |
| 18.603 |
| 12.871 |

Embodiment 5

The method described in the Summary of the Invention for preparing the polymorph Form A of Embodiment 1 comprising forming a slurry with a solvent of one or more solid forms of Compound 1 selected from the group of forms B, C, D, solvates, amorphous forms and mixtures thereof with Form A and maintaining the slurry while the solid forms of Compound 1 convert to polymorph Form A.

Embodiment 6

The method of Embodiment 5 wherein the solid form of Compound 1 comprises polymorph Form B.

Embodiment 7

The method of Embodiment 5 wherein the solid form of Compound 1 comprises polymorph Form C.

Embodiment 8

The method of Embodiment 5 wherein the solid form of Compound 1 comprises polymorph Form D.

Embodiment 9

The method of Embodiment 5 wherein the solid form of Compound 1 comprises polymorph Form TS.

Embodiment 10

The method of Embodiment 5 wherein the solid forms of Compound 1 comprises a mixture of polymorphs Form A and Form B.

Embodiment 11

The method of any one of Embodiments 5 through 10 wherein the slurry is heated to a temperature between 30° C. and the boiling point of the solvent and agitated.

Embodiment 11a

The method of any one of Embodiments 5 through 11 wherein the slurry is heated to a temperature between 55° C. and 100° C. and agitated.

Embodiment 11b

The method of any one of Embodiments 5 through 11a wherein the slurry is heated to a temperature between 65° C. and 95° C. and agitated.

Embodiment 12

The method of any one of Embodiments 5 through 10 wherein the slurry is agitated.

Embodiment 13

The method of any one of Embodiments 5 through 12 wherein the solvent comprises water, a $C_5$-$C_8$ alkane, a $C_1$-$C_4$ alkanol or a $C_3$-$C_4$ ketone.

Embodiment 14

The method of Embodiment 13 wherein the solvent comprises water, n-heptane, methanol or acetone.

Embodiment 15

The method of Embodiment 14 wherein the solvent comprises water, methanol or acetone.

Embodiment 16

The method of Embodiment 15 wherein the solvent comprises water or methanol.

Embodiment 17

The method of Embodiment 16 wherein the solvent comprises water.

Embodiment 18

The method described in the Summary of the Invention for preparing the polymorph Form A of Compound 1 comprising, (A) contacting 8-chloro-6-trifluoromethyl-imidazo[1,2-a]pyridine-2-carbonyl chloride or a salt thereof and 2-chloro-5-methoxybenzene sulfonamide in the presence of a first solvent to form a reaction mixture containing an intermediate solid form of Compound 1, (B) separating the intermediate solid form of Compound 1, and (C) contacting the intermediate solid form of Compound 1 with a second solvent optionally heated to a temperature between 30° C. and the boiling point of the second solvent to convert the intermediate solid form to the polymorph Form A of Compound 1.

Embodiment 19

The method of Embodiment 18 wherein 8-chloro-6-trifluoromethyl-imidazo[1,2-a]pyridine-2-carbonyl chloride is prepared by contacting 8-chloro-6-(trifluoromethyl)imidazo[1,2-a]pyridine-2-carboxylic acid with a chlorinating agent.

Embodiment 20

The method of Embodiment 19 wherein the chlorinating agent is thionyl chloride, oxalyl chloride or phosgene.

Embodiment 21

The method of Embodiment 20 wherein the chlorinating agent is thionyl chloride.

Embodiment 21a

The method of any one of Embodiments 19 through 21 wherein the molar ratio of the chlorinating agent to 8-chloro-6-trifluoromethyl-imidazo[1,2-a]pyridine-2-carboxylic acid is in the range of about 1.2:1 to about 1.5:1.

Embodiment 22

The method of any one of Embodiments 19 through 21a wherein 8-chloro-6-trifluoromethyl-imidazo[1,2-a]pyridine-2-carbonyl chloride is prepared by chlorinating 8-chloro-6-trifluoromethyl-imidazo[1,2-a]pyridine-2-carboxylic acid in a chlorination solvent.

Embodiment 23

The method of Embodiment 22 wherein the chlorination solvent is toluene, xylenes, chlorobenzene, anisole, mesitylene or tetralin.

Embodiment 24

The method of Embodiment 23 wherein the chlorination solvent is toluene, xylenes or anisole.

Embodiment 25

The method of Embodiment 24 wherein the chlorination solvent is toluene.

Embodiment 26

The method of any one of Embodiments 19 through 25 wherein 8-chloro-6-(trifluoromethyl)imidazo[1,2-a]pyridine-2-carboxylic acid is contacted with a chlorinating agent in the presence of N,N-dimethylformamide or N-formylpiperidine.

Embodiment 27

The method of Embodiment 26 wherein 8-chloro-6-(trifluoromethyl)imidazo[1,2-a]pyridine-2-carboxylic acid is contacted with a chlorinating agent in the presence of N-formylpiperidine.

Embodiment 27a

The method of Embodiment 26 wherein 8-chloro-6-(trifluoromethyl)imidazo[1,2-a]pyridine-2-carboxylic acid is contacted with a chlorinating agent in the presence of N,N-dimethylformamide.

Embodiment 28

The method of any one of Embodiments 19 through 27a wherein 8-chloro-6-(trifluoromethyl)imidazo[1,2-a]pyridine-2-carboxylic acid is contacted with a chlorinating agent in the temperature range of 0 to 85° C.

Embodiment 29

The method of Embodiment 28 wherein 8-chloro-6-(trifluoromethyl)imidazo[1,2-a]pyridine-2-carboxylic acid is contacted with a thionyl chloride in the temperature range of 75 to 85° C.

Embodiment 30

The method of any one of Embodiments 19 through 29 wherein excess chlorinating agent is removed from the 8-chloro-6-trifluoromethyl-imidazo[1,2-a]pyridine-2-carbonyl chloride before it is contacted with 2-chloro-5-methoxybenzene sulfonamide.

Embodiment 31

The method of any one of Embodiments 18 through 30 wherein the 8-chloro-6-trifluoromethyl-imidazo[1,2-a]pyridine-2-carbonyl chloride in step (A) is in the form of an HCl salt.

Embodiment 32

The method of any one of Embodiments 22 through 31 wherein the 8-chloro-6-trifluoromethyl-imidazo[1,2-a]pyridine-2-carbonyl chloride in step (A) is in the form of a slurry in the chlorination solvent.

Embodiment 33

The method of any one of Embodiments 18 through 32 wherein the molar ratio of 8-chloro-6-trifluoromethyl-imidazo[1,2-a]pyridine-2-carboxylic acid and 2-chloro-5-methoxybenzene sulfonamide in step (A) is in the range of 1:1.1 to 1:1.

Embodiment 34

The method of any one of Embodiments 18 through 33 wherein in step (A) the 8-chloro-6-trifluoromethyl-imidazo[1,2-a]pyridine-2-carbonyl chloride and the 2-chloro-5-methoxybenzene sulfonamide are contacted in the presence of a base.

Embodiment 35

The method of Embodiment 34 wherein the base is a tertiary amine.

Embodiment 36

The method of Embodiment 35 wherein the base is tributylamine, triethylamine or diisopropylethylamine.

Embodiment 37

The method of Embodiment 36 wherein the base is tributylamine.

Embodiment 38

The method of any one of Embodiments 34 through 37 wherein the molar ratio of base to 2-chloro-5-methoxybenzene sulfonamide in step (A) is in the range of 2.8:1 to 3.5:1.

Embodiment 39

The method of any one of Embodiments 22 through 38 wherein the first solvent comprises a mixture of the chlorination solvent with at least one solvent selected from ethyl acetate, tetrahydrofuran, dichloromethane and dichloroethane with the chlorination solvent.

Embodiment 40

The method of Embodiment 39 wherein the first solvent comprises a mixture of the chlorination solvent with ethyl acetate.

Embodiment 40a

The method of Embodiment 40 wherein the first solvent comprises a mixture of toluene with ethyl acetate.

Embodiment 41

The method of any one of Embodiments 18 through 40a wherein in step (A) the 8-chloro-6-trifluoromethyl-imidazo[1,2-a]pyridine-2-carbonyl chloride and the 2-chloro-5-methoxybenzene sulfonamide are contacted in the temperature range of 0 to 25° C.

Embodiment 42

The method of Embodiment 41 wherein in step (A) the 8-chloro-6-trifluoromethyl-imidazo[1,2-a]pyridine-2-carbonyl chloride and the 2-chloro-5-methoxybenzene sulfonamide are contacted in the temperature range of 15 to 25° C.

Embodiment 43

The method of any one of Embodiments 39 through 42 wherein when the reaction in step (A) is complete, at most 1 equivalent of aqueous acid for every equivalent of the base is added to neutralize the reaction mixture.

Embodiment 44

The method of Embodiment 43 wherein the aqueous acid is hydrochloric acid.

Embodiment 45

The method of Embodiments 43 or 44 wherein after addition of aqueous acid, the reaction mixture is heated in the range of 50 to 60° C. for in the range of one to two hours to form the intermediate solid form of Compound 1.

Embodiment 46

The method of any one of Embodiments 43 through 45 wherein after the reaction mixture is heated in the presence of aqueous acid, the reaction mixture is cooled to a temperature in the range of 5 to 15° C.

Embodiment 47

The method of any one of Embodiments 18 through 46 wherein in step (B) the reaction mixture is filtered to separate the intermediate solid form of Compound 1.

Embodiment 48

The method of Embodiment 47 wherein the intermediate solid form of Compound 1 is a solvate.

Embodiment 48a

The method of Embodiment 48 wherein the intermediate solid form of Compound 1 is a toluene solvate.

Embodiment 48b

The method of Embodiment 47 wherein the intermediate solid form of Compound 1 is an unsolvated polymorph or mixture of polymorphs.

Embodiment 49

The method of any one of Embodiments 18 through 48b wherein the intermediate solid form of Compound 1 separated in step (B) is contacted with a second solvent in step (C) to convert the intermediate solid form of Compound 1 to polymorph Form A.

Embodiment 50

The method of any one of Embodiments 18 through 49 wherein the temperature in step (C) is between 30° C. and the boiling point of the second solvent.

Embodiment 51

The method of Embodiment 50 wherein the temperature in step (C) is at least 30° C.

Embodiment 51a

The method of Embodiment 50 wherein the temperature in step (C) is at least 55° C.

Embodiment 52

The method of Embodiment 50 wherein the temperature in step (C) is at most the boiling point of the second solvent.

Embodiment 53

The method of any one of Embodiments 18 through 52 wherein the second solvent comprises water, methanol, acetone or n-heptane.

Embodiment 54

The method of Embodiment 53 wherein the second solvent comprises water or methanol.

Embodiment 55

The method of Embodiment 54 wherein the second solvent comprises water.

Embodiment 56

The method of any one of Embodiments 18 through 55 wherein the second solvent is water and the temperature of step (C) is in the range of 90 to 100° C.

Embodiment 57

The method of any one of Embodiments 18 through 54 wherein the second solvent is methanol and the temperature of step (C) is in the range of 55 to 65° C.

Embodiment 58

The method of any one of Embodiments 18 through 57 wherein when the conversion in step (C) is complete, the second solvent is cooled and polymorph Form A is separated from the second solvent by filtration.

Embodiments of this invention, including Embodiments 1-58 above as well as any other embodiments described herein, can be combined in any manner.

Compound 1 is 8-chloro-N-[(2-chloro-5-methoxyphenyl)sulfonyl]-6-(trifluoromethyl)-imidazo[1,2-a]pyridine-2-carboxamide and has the following molecular structure:

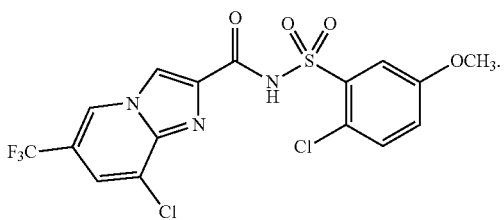

1

The solid state of Compound 1 has now been discovered to be preparable in more than one solid form. These solid forms include an amorphous solid form, in which there is no long-range order in the positions of molecules (e.g., foams and glasses). These solid forms also include crystalline forms, in which constituent molecules are arranged in an orderly repeating pattern extending in all three spatial dimensions. The term "polymorph" refers to a particular crystalline form of a chemical compound that can exist in more than one crystal structure (e.g. lattice type) in the solid state. The term "packing polymorphs" refers to particular crystalline forms of a compound having different crystal packing. Crystalline forms of Compound 1 in this invention relate to embodiments which include a single polymorph (i.e. single crystalline form) and to embodiments which include a mixture of polymorphs (i.e. different crystalline forms). Polymorphs can differ in such chemical, physical and biological properties as crystal shape, density, hardness, color, chemical stability, melting point, hygroscopicity, suspensibility, solubility, dissolution rate and biological availability. One skilled in the art will appreciate that a polymorph of Compound 1 can exhibit beneficial effects (e.g., suitability for preparation of useful formulations, stability, improved biological performance) relative to another polymorph or a mixture of polymorphs of Compound 1. Differences with respect to chemical stability, filterability, solubility, hygroscopicity, melting point, solid density and flowability can have a significant effect on the development of production methods and formulations, and efficacy of nematode control. Preparation and isolation of particular polymorphs of Compound 1 have now been achieved.

One crystalline polymorph form of Compound 1, designated as polymorph Form TS, is a 1:1 (molar ratio) toluene solvate. Polymorph Form TS can be characterized by X-ray powder diffraction, single crystal X-ray structure analysis and Differential Scanning Calorimetry.

The powder X-ray diffraction pattern of polymorph Form TS of Compound 1 is shown in FIG. 1. The corresponding 2θ values are tabulated in Table 8 of Characterization Example 5. Polymorph Form TS of Compound 1 can be identified by a room-temperature powder Cu(Kα1) X-ray diffraction pattern having at least the 2θ reflection positions (in degrees)

| 2θ |
|---|
| 28.913 |
| 26.942 |
| 25.672 |
| 24.451 |
| 23.316 |
| 22.429 |
| 20.325 |
| 19.053 |
| 18.603 |
| 12.871 |

Single crystal X-ray diffraction can also be used to characterize polymorph Form TS. A description of single crystal X-ray diffraction of polymorph Form TS is provided in Characterization Example 10. Crystals of polymorph Form TS have a triclinic unit cell and typically exhibit a needle-like morphology.

Polymorph Form TS of Compound 1 can also be characterized by Differential Scanning Calorimetry. DSC indicates the melting point of polymorph Form TS is about 217° C. The details of a DSC experiment are provided in Characterization Example 11.

Polymorph Form TS can be prepared directly during the preparation of Compound 1 from its starting materials in the presence of toluene solvent as described in Preparation Example 1. Polymorph Form TS can also be prepared by slow evaporation of a saturated solution of Compound 1 in toluene. Polymorph Form TS can be converted into other polymorph forms or mixtures of forms as described in Preparation Examples 2 through 4.

A second crystalline polymorph form of Compound 1 is designated as polymorph Form A. This solid form is unsolvated. Polymorph Form A can be characterized by X-ray powder diffraction, single crystal X-ray structure analysis and Differential Scanning Calorimetry (DSC).

The powder X-ray diffraction pattern of polymorph Form A of Compound 1 is shown in FIG. 1. The corresponding 2θ values are tabulated in Table 4 of Characterization Example 1. Polymorph Form A of Compound 1 can be identified by a room-temperature powder Cu(Kα1) X-ray diffraction pattern having at least the 2θ reflection positions (in degrees)

| 2θ |
|---|
| 30.367 |
| 29.131 |
| 27.995 |
| 27.611 |

| 2θ |
|---|
| 26.49 |
| 25.973 |
| 25.604 |
| 24.285 |
| 23.582 |
| 19.789 |

Single crystal X-ray diffraction can also be used to characterize polymorph Form A. A description of single crystal X-ray diffraction of polymorph Form A is provided in Characterization Example 6. Crystals of polymorph Form A have a triclinic unit cell and typically exhibit a irregular block morphology.

Polymorph Form A of Compound 1 can also be characterized by Differential Scanning Calorimetry. DSC indicates the melting point of polymorph Form A is about 219° C. The details of a DSC experiment are provided in Characterization Example 11. Polymorph Form A is physically and chemically stable in its pure solid form (shown in Characterization Example 13).

Pure Polymorph Form A can be prepared by desolvating the toluene solvate (Form TS) via heating in a solvent like water or methanol as described in Preparation Examples 3 and 4. Polymorph Form A of Compound 1 can also be prepared by heating a mixture of polymorph Forms A and B at or near the boiling point of a solvent and then cooling back to room temperature or lower as described in Preparation Example 5. Methanol, water, acetone or n-heptane are particularly useful solvents for this method.

Another crystalline polymorph form of Compound 1 is designated as Polymorph Form B. This solid form is unsolvated. Polymorph Form B can be characterized by X-ray powder diffraction, single crystal X-ray structure analysis and Differential Scanning Calorimetry.

Single crystal X-ray diffraction can be used to characterize polymorph Form B. A description of single crystal X-ray diffraction of polymorph Form B is provided in Characterization Example 7. Crystals of polymorph Form B have a triclinic unit cell and typically exhibit a prism morphology.

A simulated powder pattern was calculated from the atomic coordinates and cell parameters determined from the single crystal structure for polymorph Form B of Compound 1 and is shown in FIG. 1. The corresponding 2θ values of the powder X-ray diffraction pattern of polymorph Form B are tabulated in Table 5 of Characterization Example 2. Polymorph Form B of Compound 1 can be identified by a –100° C. simulated powder Cu(Kα1) X-ray diffraction pattern having at least the 2θ reflection positions (in degrees)

| 2θ |
|---|
| 28.242 |
| 25.978 |
| 25.06 |
| 24.583 |
| 23.082 |
| 20.999 |
| 18.981 |
| 18.12 |
| 17.219 |
| 7.998 |

Polymorph Form B of Compound 1 can also be characterized by Differential Scanning Calorimetry. DSC indicates the melting point of polymorph Form B is about 218° C. The details of a DSC experiment are provided in Characterization Example 11.

Polymorph Form B can be obtained as a mixture with polymorph Form A by desolvation of the toluene solvate (Form TS) as described in Preparation Example 2. Polymorph Form B can be prepared by heating the mixture of polymorph Forms A and B in dichloromethane as described in Preparation Example 5. Polymorph Form B of Compound 1 can also be prepared by thermal gradient sublimation at 160° C.

Another crystalline polymorph form of Compound 1 is designated as polymorph Form C. This solid form is unsolvated. Polymorph Form C can be characterized by X-ray powder diffraction and single crystal X-ray structure analysis.

Single crystal X-ray diffraction can be used to characterize polymorph Form C. A description of single crystal X-ray diffraction of polymorph Form C at –100° C. is provided in Characterization Example 8 and at 23° C. in Characterization Example 14. Crystals of polymorph Form C have a triclinic unit cell and typically exhibit a triangular plate morphology.

A simulated powder pattern was calculated from the atomic coordinates and cell parameters determined from the single crystal structure for polymorph Form C at –100° C. of Compound 1 and is shown in FIG. 1. The corresponding 2θ values of the –100° C. simulated powder Cu(Kα1) X-ray diffraction pattern of polymorph Form C are tabulated in Table 6 of Characterization Example 3. The corresponding 2θ values of the room temperature simulated powder Cu(Kα1) X-ray diffraction pattern of polymorph Form C are tabulated in Table 22 of Characterization Example 15.

Polymorph Form C of Compound 1 can be prepared by thermal gradient sublimation at 160° C.

Another crystalline polymorph form of Compound 1 is designated as polymorph Form D. This solid form is unsolvated. Polymorph Form D can be characterized by X-ray powder diffraction, single crystal X-ray structure analysis and Differential Scanning Calorimetry.

Single crystal X-ray diffraction can be used to characterize polymorph Form D. A description of single crystal X-ray diffraction of polymorph Form D is provided in Characterization Example 9. Crystals of polymorph Form D have a triclinic unit cell and typically exhibit an irregular block morphology.

A simulated powder pattern was calculated from the atomic coordinates and cell parameters determined from the single crystal structure for polymorph Form D of Compound 1 and is shown in FIG. 1. The corresponding 2θ values of the powder X-ray diffraction pattern of polymorph Form D are tabulated in Table 7 of Characterization Example 4. Polymorph Form D of Compound 1 can be identified by a –100° C. simulated powder Cu(Kα1) X-ray diffraction pattern having at least the 2θ reflection positions (in degrees)

| 2θ |
|---|
| 27.323 |
| 25.581 |
| 23.958 |
| 22.459 |
| 20.68 |
| 18.398 |
| 17.821 |
| 14.558 |
| 12.182 |
| 5.943 |

Polymorph Form D of Compound 1 can also be characterized by Differential Scanning Calorimetry. DSC indicates the melting point of polymorph Form D is about 218° C. The details of a DSC experiment are provided in Characterization Example 11.

Pure polymorph Form D can be prepared by heating the mixture of polymorph Forms A and B in acetonitrile or acetic acid as described in Preparation Examples 5 and 6.

Compound 1 can also exist as an amorphous solid. The powder X-ray diffraction pattern (pXRD) for the amorphous form of Compound 1 shows a broad reflection pattern across the two-theta angle lacking distinct reflection signals and thus is readily distinguished from the pXRD patterns of crystalline forms of Compound 1. The amorphous solid form can be prepared by standard methods known in the art, such as evaporation to dryness of solutions containing Compound 1, by quick cooling of melted Compound 1, by spray drying a solution of Compound 1 or by freeze-drying a frozen solution containing Compound 1.

Compound 1 can be prepared by a variety of methods. One method involves coupling the starting acid 8-chloro-6-(trifluoromethyl)imidazo[1,2-a]pyridine-2-carboxylic acid and 2-chloro-5-methoxybenzenesulfonamide with any number of amide bond forming coupling reagents. An especially useful method utilizes 1-(3-dimethyl-aminopropyl)-3-ethyl-carbodiimide hydrochloride and is described in Synthesis Example 1 in World Patent Publication WO 2010/129500. Another method utilizes the mixed anhydride of the starting carboxylic acid as a method of promoting easy amid bond formation with the sulfonamide. Some of the most useful reagents used to make the mixed anhydride of the starting carboxylic acid are ethyl chloroformate and isobutyl chloroformate. Another method to prepare Compound 1 involves the formation of an ester of the starting acid and reacting it with the sodium salt of the sulfonamide. Useful esters of the starting acid are the methyl- or ethyl-ester. The sodium salt of the sulfonamide can be prepared by reaction with sodium hydride. Compound 1 can also be prepared from the acid chloride of the starting carboxylic acid and coupling with the sulfonamide as described in Preparation Example 1.

The preparation of polymorph Form A of Compound 1 can be accomplished by a process wherein Compound 1 is prepared from its starting materials (Preparation Example 1) to initially yield an intermediate solid form of Compound 1. The intermediate solid form initially isolated can be a mixture of polymorph forms, a polymorph form other than Form A or a solvate of Compound 1. The intermediate solid form of Compound 1 can be converted into pure polymorph Form A by a variety of methods (Preparation Examples 2 through 5 and Characterization Example 19).

An especially useful method to prepare the polymorph Form A of Compound 1 is a process wherein the intermediate solid form of Compound 1 is a toluene solvate (Polymorph Form TS). Polymorph Form TS is prepared directly from precursor starting materials as shown in Scheme 1. The method involves treating a compound of Formula 2 (8-chloro-6-(trifluoromethyl)imidazo[1,2-a]pyridine-2-carboxylic acid) with a chlorinating agent in the presence of a chlorinating solvent (toluene) to make the acid chloride of Compound 3. The acid chloride Compound 3 is then treated with a compound of Formula 4 (2-chloro-5-methoxybenzenesulfonamide) in the presence of base to form a salt of Compound 1. When the reaction is complete the mixture is treated with aqueous acid to neutralize any excess base and ensure formation of the neutral acyl sulfonamide product. The aqueous slurry is warmed and stirred to dissolve salts and encourage the product to crystallize out of solution. The product crystallizes as the toluene solvate of Compound 1 (Form TS) and is separated by solid-liquid separation (e.g. filtration) and either dried to form the pure solvate or processed further to form polymorph Form A.

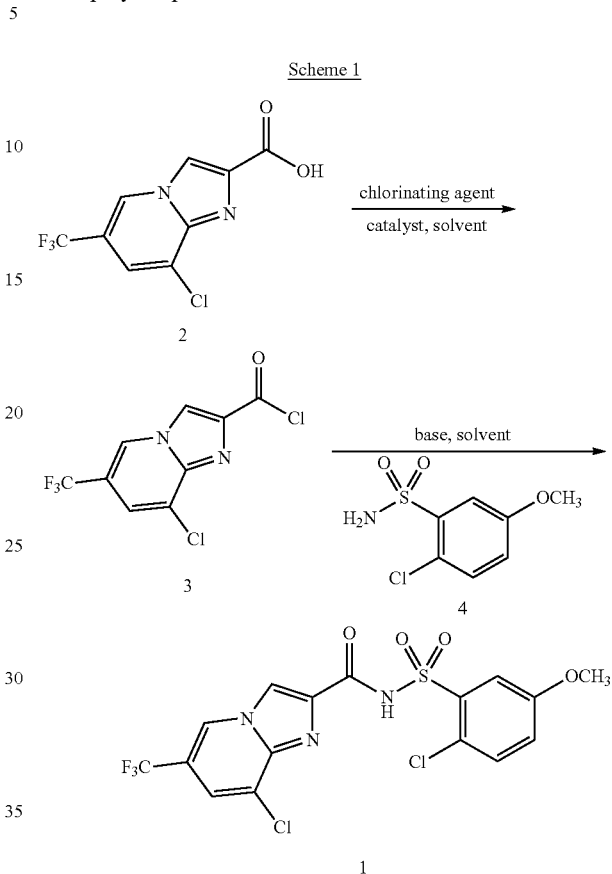

Scheme 1

The reaction corresponding to the first part of Scheme 1 is typically run using 1 to 2 molar equivalents of the chlorinating agent relative to Compound 2. More typically the molar ratio of the chlorinating agent to the compound of Formula 2 is in the range of about 1.2:1 to about 1.5:1. A larger ratio of chlorinating agent to Compound 2 is needed if Compound 2 contains some residual water. Chlorinating agents that are useful for this transformation include thionyl chloride, oxalyl chloride or phosgene. Thionyl chloride is especially useful. The formation of the acid chloride is usually catalyzed by the addition of a formamide in the range of 1 to 10 weight percent relative to Compound 2. Useful catalysts for acid chloride formation include N,N-dimethylformamide and N-formylpiperidine. Solvents useful for the chlorination in Scheme 1 (chlorination solvent) are any solvents that are inert to the chlorination reagent. Solvents that are especially useful are toluene, xylenes, chlorobenzene, anisole, mesitylene and tetralin. Toluene is an especially useful solvent. The formation of the acid chloride (Compound 3) is usually done in a temperature range appropriate for the chlorination reagent usually in the range of 0 to 85° C. or near the boiling point of the chlorinating reagent. The lower temperatures are appropriate for oxalyl chloride or phosgene. A temperature in the range of 75 to 85° C. is useful for thionyl chloride. The progress of the reaction may be monitored by the formation of the methyl ester of Compound 2. An aliquot of the reaction mixture is treated with methanol and is analyzed by HPLC to determine the ratio of unreacted Compound 2 and the ester from reaction of Compound 3 with methanol. Reaction times are typically in the range of 2 to 3 hours. Finally, to separate the acid chloride from the chlorinating agent, the reaction mixture is heated to the boiling point of the reaction mixture to remove excess chlorinating agent (thionyl chloride) and reduce the amount of solvent. The reaction mass is concentrated to about one-half volume and the resultant slurry (Compound 3 in chlorination solvent) is cooled to room temperature. When thionyl chloride is the chlorinating agent and toluene is the chlorination solvent then the resultant slurry is the hydrochloride salt of Compound 3 in toluene.

The second part of Scheme 1 involves the reaction of the Compound of Formula 3 and the sulfonamide of Formula 4 to form the acyl sulfonamide Compound 1. The molar ratio of reactants is usually in the range of 1 to 1.1 equivalents of Compound 4 to 1 equivalent of Compound 2 with a ratio of 1.05 equivalents of Compound 4 to 1 equivalent of Compound 2 being especially useful. The coupling reaction is run in the presence of a base to neutralize the equivalent of hydrogen chloride released. The quantity of base used is usually in the range of 2.5 to 4 equivalents relative to the sulfonamide, with a range of 2.8 to 3.5 being especially useful. The base is used to neutralize the equivalent of HCl from the acid chloride salt starting material (the nitrogen containing heterocycle in Compound 3 forms a hydrochloride salt in strong acidic conditions) and the equivalent of HCl generated in the reaction of the acid chloride and sulfonamide. The base also removes a proton from the acidic acylsulfonamide functional group in the product to form a salt of the product. A variety of tertiary amines can be used as bases for this coupling reaction. Examples are tributylamine, triethylamine, and diisopropylethylamine. Solvents useful for the second part of Scheme 1 are polar aprotic solvents that provide some solubility for the sulfonamide and Compound 1. Solvents that are useful include ethyl acetate, tetrahydrofuran, dichloromethane and dichloroethane. Ethyl acetate is especially useful. The slurry of acid chloride from part A is usually diluted with ethyl acetate in a ratio of about 1 volume of toluene slurry to 1 to 2 volumes of ethyl acetate. The "first solvent" of the process to prepare polymorph Form A of Compound 1 (step (A)) is a mixture of the chlorination solvent and the solvent added for solubility in the coupling reaction (e.g. ethyl acetate). The reaction mixture (Compound 3 in the solvent mixture) is cooled to a temperature in the range of 0 to 15° C. and treated with the Compound 4. The tertiary amine base is then added dropwise and the reaction mixture allowed to warm to room temperature. The reaction is stirred for a time in the range of 2 to 18 hours. The reaction is again monitored by treating an aliquot of the reaction mixture with methanol and observing the relative ratios of methyl ester of Compound 2, Compound 4 and Compound 1.

Upon completion of the reaction, the reaction mixture is usually diluted with water to dissolve salts and reduce the solubility of the product, thus promoting the crystallization of product of high purity. Aqueous acid is then added to the reaction mixture to form a salt of any excess tertiary amine that was not already in the hydrochloride salt form. This acidification is necessary to release the product Compound 1 in its neutral form from the tertiary amine salt that forms with the acidic acylsulfonamide functional group in the product. Typically at least about 1 molar equivalent of acid is added for every equivalent of tertiary amine base in excess of the number of equivalents of acid chloride used in the reaction. More than 1 equivalent of acid for every equivalent of tertiary amine base used in the reaction can be added to ensure an acidic environment, although to minimize cost and waste disposal, typically not more than about 0.5 equivalent of excess acid is added. Other water-soluble acids can be used in place of hydrochloric acid. An example of another suitable water-soluble acid is sulfuric acid. For multi protic acids the molar equivalents of acids may have to be adjusted according to the number of available protons. When the addition of the acid is complete, the reaction mixture is usually heated in the range of 50 to 60° C. and stirred in the range of 1 to 2 hours. This procedure promotes formation of larger size crystals to facilitate filtration. The reaction slurry is then cooled to a temperature in the range of 5 to 15° C. and filtered. The wet solid is washed several times with water, to remove traces of salts and excess acid. The wet solid is then also washed several times with toluene to displace any remaining water and ethyl acetate from the solid product. This crude wet solid is a 1:1 (molar ratio) solvate of Compound 1 and toluene (polymorph Form TS).

The toluene solvate (Form TS) of the product is formed from toluene solvent used in the first part of the process that was carried into the second part of the process to prepare Compound 1. If the chlorination is performed with a solvent other than toluene the resultant intermediate solid form of Compound 1 will not be isolated as a toluene solvate. The crude product Compound 1 can be isolated as a solvate of any solvent that is part of the "first solvent" mixture used in the coupling process, if it forms a strong solvate. Alternatively, when the solvents used in the preparation of Compound 1 do not have a tendency to form solvates (e.g. o-xylene) then the intermediate solid form of Compound 1 product can be isolated as an unsolvated polymorph or mixture of polymorphs.

Compound 1 in the form of a solvate, unsolvated polymorph or mixture of polymorphs is initially "separated" from the reaction mixture by filtration to yield a wet solid or wet cake. The separated solid form of Compound 1 can then be further "isolated" by drying or removing the last traces of solvent adhering to the external surface of the solid. The separated wet solid or isolated dry solid can then be further converted to other polymorph forms. The isolated solid can also be characterized by a variety of analytical methods.

The crude wet solid polymorph Form TS can be used as is for further conversion as described in Preparation Example 3. Polymorph Form TS can be desolvated and converted to polymorph Form A by forming a slurry in water and distilling at about 95-96° C. in an apparatus that allows for the removal of toluene into the distillate by azeotropic distillation, e.g. using a Dean-Stark trap. The mixture is heated for 3 to 5 hours and water collected in the Dean-Stark trap is returned to the reaction to maintain constant reaction volume while toluene is removed from the slurry. The reaction is cooled to ambient temperature, filtered and dried under vacuum (8-15 kPa absolute pressure) at 55° C. for one hour. The resultant product is pure polymorph Form A as determined by pXRD. Variations of this procedure resulting in the same conversion of polymorph Form TS to Form A are described in Preparation Example 4. Both water and methanol and mixtures of water and methanol can act as the solvent for the desolvation procedure by distillation, e.g. with the Dean-Stark apparatus. The desolvation/polymorph conversion reaction can be accomplished at a temperature between about 30° C. and the boiling point of the solvent. The desolvation/polymorph conversion reaction is especially efficient at a temperature between about 55° C. and the boiling point of the solvent (the boiling point of the solvent varies depending on the solvent or solvent mixture used) as shown in Table 2 of Preparation Example 4. The consistent result is pure polymorph Form A indicating that it is the most stable polymorph form in the range of studied reaction conditions.

The crude wet solid of polymorph Form TS can also be desolvated by drying in a vacuum oven at about 90° C. (8-15 kPa absolute pressure) for about 4 days to give a mixture of polymorph Forms A and B as described in Preparation Example 2. The mixture of polymorph Forms A and B that results from the desolvation of polymorph Form TS can then be further converted into other polymorph forms as described in Preparation Example 5. A sample of polymorph Forms A and B, originally derived from desolvation of Form TS, is suspended in a solvent and heated and stirred for a time period and then cooled and isolated by filtering and drying in a vacuum oven. A variety of solvents can be used in this conversion procedure and the particular polymorph form that results depends on the solvent used. The results are summarized in Table 3 of Preparation Example 5. A variety of solvents give pure polymorph Form A. Heating under agitation at 95-100° C. for 3 hours in water or n-heptane results in polymorph Form A. Heating under agitation at 60° C. for 3 hours in methanol also results in polymorph Form A. The starting polymorph mixture dissolved in some of the solvents upon warming and therefore those solvent's solutions were cooled to or below ambient temperature to encourage crystallization. The crystal form conversion in these solvents resulted in a variety of polymorph forms. Acetone (also water, methanol and n-heptane) resulted in polymorph Form A, dichloromethane resulted in polymorph Form B and both acetonitrile and acetic acid resulted in polymorph Form D.

The relative stability of pure polymorphs and mixtures of polymorphs of Compound 1 were studied in water heated to 95° C. or methanol heated to 55° C. in Characterization Example 12. In all cases the starting polymorph or mixtures of polymorphs converted to Form A. These experiments indicate that Form A is the most thermodynamically stable polymorph form under the conditions studied. The data in Characterization Example 12 shows that polymorph Form B and polymorph Form D can act as intermediates to prepare polymorph Form A. Polymorph Form TS is also demonstrated to be an intermediate to prepare polymorph Form A in Preparation Examples 3 and 4.

Seed crystals were not used in the above described polymorph conversions, however, seed crystals can be used to promote conversion and/or increase the rate of conversion of one polymorph into another. The polymorph conversion reactions are often agitated by a variety of methods even if not explicitly stated. The form of agitation can be from shaking the reaction vessel or by stirring with a magnetic or mechanical stirrer. The polymorph conversion reactions can also be agitated by the boiling action of the solvent.

Without further elaboration, it is believed that one skilled in the art using the preceding description can utilize the present invention. The following Examples are, therefore, to be construed as merely illustrative, and not limiting of the disclosure in any way whatsoever. Abbreviations used in the examples are as follows: rpm is revolutions per minute, pXRD is powder X-ray diffraction, wt % is percent by weight measured by HPLC (using a calibration standard), a % is percent by area measured by HPLC at a wavelength of 230 nm, DSC is differential scanning calorimetry, TGA is thermal gravimetric analysis and KFT is Karl-Fischer titration.

Analytical methods used in the preparation examples are described below or in the Characterization Examples.

Powder X-Ray Diffraction (p-XRD)

Powder X-ray diffraction was used to identify the crystalline phases of various samples of Compound 1. Data were obtained with a Philips X'PERT automated powder diffractometer, Model 3040. The radiation produced by a copper anode X-ray source includes Cu-K(alpha1), Cu-K(alpha2) and Cu-K(beta). The diffractometer was equipped with a nickel filter that removes the Cu-K(beta) radiation leaving Cu-K(alpha1) and Cu-K(alpha2) in the raw data. The peaks originating from Cu-K(alpha 2) are removed during the find peaks routine in the Jade Software (MDI/Jade software version 9.1) leaving the listed maxima from Cu-K(alpha1). The wavelength for Cu-K(alpha1) or Cu(Kα1) radiation listed in International Tables for X-ray Crystallography is 0.154056 nm. The listed 2θ X-ray maxima are for Cu-K(alpha1) radiation which is the strongest radiation produced by a copper anode X-ray source and is sometimes simply abbreviated as Cu-K(alpha) or Cu-Ku.

Thermo-Gravimetric Analysis (TGA)

Thermo-gravimetric Analysis was performed on a Thermal Analysis Q5000 equipment to determine the relative weight loss of a sample as a function of temperature. Test samples (2-6 mg) were accurately weighed into sample pans (platinum, 100 μL). The samples were heated from starting temperature (25° C.) to final temperature (250 or 300° C.) at a heating rate of 10° C./min under a nitrogen flow of 25 mL/min. The TGA scans were analyzed and plotted using Thermal Analysis Advantage thermal analysis software.

High Performance Liquid Chromatography (HPLC)

HPLC was used to determine the purity of Compound 1 and intermediates. An Agilent 1100/1200 series HPLC system with DAD/UV detector and reverse-phase column (Agilent Zorbax® SB C18 (4.6×150) mm, 3.5 μm, Part No. 863953-902) was used. Flow rate was 1 mL/min, run time 25 min, injection volume 3.0 μL, and the column oven temperature was 40° C. A mobile phase gradient according to Table 1 was used wherein mobile phase A was 0.075% by volume orthophosphoric acid and mobile Phase B was acetonitrile (HPLC grade). Mobile phase A was prepared by thoroughly mixing 0.75 mL of orthophosphoric acid (AR grade) with 1000 mL of deionized water (Milli-Q grade) and filtering through a membrane filter (0.45 μm pore size). Standards were prepared by weighing 30.0 mg of the standard into a 100 mL standard volumetric flask, dissolving and diluting with the diluent. Samples were prepared by weighing 30.0 mg of the sample into a 100 mL standard volumetric flask, dissolving and diluting with the diluent. For analysis, the HPLC system and column were equilibrated with initial mobile phase. In sequence, a blank sample, a standard sample and the test sample were run. The retention time for Compound 1 was about 14.8 min. Peaks appearing in the blank sample were not integrated, all other peaks were integrated and a % purity reported from the sample chromatogram. For wt % determination the concentration of test sample was calibrated against the standard sample.

TABLE 1

Mobile Phase Gradient Table

| Time (min) | Volume Fraction of Mobile Phase A (%) | Volume Fraction of Mobile Phase B (%) |
|---|---|---|
| 0 | 80 | 20 |
| 15 | 30 | 70 |
| 19 | 10 | 90 |
| 25 | 10 | 90 |

Proton-Nuclear Magnetic Resonance ($^1$H-NMR)

Proton-NMR analysis was performed on a Bruker Advance 300/400 instrument. The operational frequency was 400 MHz, spectral frequency range 0-16 ppm, delay time 2 seconds, pulse width of 12 μs, minimum number of scans was 8. Samples were prepared by weighing about 0.01 g of samples or reference standards, adding 0.6 mL of DMSO-$d_6$ to dissolve the contents and transferring into NMR tubes. Deuterated DMSO (DMSO-$d_6$) was from Cambridge Isotope Laboratory.

Water Content

Water content analysis was performed by Karl-Fischer titration (KFT).

Preparation Example 1

Synthesis of Toluene Solvate Form of Compound 1 (Form TS)

Step A: Preparation of 8-chloro-6-(trifluoromethyl) imidazo[1,2-a]pyridine-2-carbonyl chloride To a 3000 mL three-neck round bottom flask equipped with an overhead stirrer, thermo pocket, addition funnel and nitrogen tube was charged toluene (1000 mL), N-formyl piperidine (3.54 g, 0.031 mol) and thionyl chloride (67 g, 0.559 moles) at 23° C. under nitrogen atmosphere. The resultant reaction mass was heated to 82° C. and to this 8-chloro-6-(trifluoromethyl)imidazo[1,2-a]pyridine-2-carboxylic acid (100 g, 0.373 moles) (prepared as in WO 2010/129500) was charged lot wise (5 lots) over a period of 60 min. The walls of the reactor were rinsed with 500 mL toluene. After addition, the resultant reaction mass was stirred at 90° C. for 75 min and the progress of the reaction was monitored by HPLC. For this, 0.5 mL of the reaction mass was diluted with 3 mL of methanol and the formation of acid chloride was analyzed indirectly by detecting its corresponding methyl ester by HPLC). After 2 hours, HPLC analysis indicated about 0.35 a % of unreacted 8-chloro-6-(trifluoromethyl)imidazo[1,2-a]pyridine-2-carboxylic acid and about 99.0 a % of 8-chloro-6-(trifluoromethyl)imidazo[1,2-a]pyridine-2-carboxylic acid methyl ester. The resultant reaction mass was further heated to 140° C. (oil bath temperature) and distilled at about 109° C. (mass temperature) and 105-107° C. (vapor temperature) at atmospheric pressure over a period of 2.5 hours to remove toluene (about 600 mL) and excess thionyl chloride present in the reaction mass. After distillation, the reaction mass was gradually cooled to 30° C. over a period of 60 min. The concentration of 8-chloro-6-(trifluoromethyl)imidazo[1,2-a]pyridine-2-carboxylic acid was about 0.07 a % and the concentration of 8-chloro-6-(trifluoromethyl)imidazo[1,2-a]pyridine-2-carboxylic acid methyl ester about 99.2 a % as measured by HPLC at 230 nm.

Step B: Preparation of 8-chloro-N-[(2-chloro-5-methoxyphenyl)sulfonyl]-6-(trifluoromethyl)-imidazo[1,2-a]pyridine-2-carboxamide (Compound 1)

The resultant acid chloride solution from Step A was cooled to 0° C. over a period of 30 min and to this, ethyl acetate (400 mL) was charged under a nitrogen atmosphere at 0° C. The resultant reaction mass was stirred at 0° C. for 5 min and to this 2-chloro-5-methoxybenzenesulfonamide (90 g, 0.391 moles) (prepared as in WO 2010/129500) was charged.

To the resultant reaction mass tributylamine (242 g, 1.305 moles) was added dropwise over a period of 60 min using an addition funnel. A temperature increase of 8° C. was observed during the addition. After the addition, the resultant reaction mass was stirred at 10° C. for 30 min and the temperature was gradually raised to 25° C. The progress of the reaction was monitored. For this, 0.5 mL the reaction mass was diluted with 3 mL of methanol and analyzed by HPLC analysis at 230 nm. After about 15 min at 25° C., the concentration of 8-chloro-6-(trifluoromethyl)imidazo[1,2-a]pyridine-2-carboxylic acid methyl ester was about 4.30 a %, 8-chloro-6-(trifluoromethyl)imidazo[1,2-a]pyridine-2-carboxylic acid about 1.81 a %, unreacted 2-chloro-5-methoxybenzenesulfonamide was about 2.86 a % and Compound 1 was about 86.5 a %. The resultant reaction mass was stirred overnight at 25° C. and the progress of the reaction was monitored by HPLC at 230 nm. After 15 hours at 25° C., the concentration of 8-chloro-6-(trifluoromethyl)imidazo[1,2-a]pyridine-2-carboxylic acid methyl ester was about 0.84 a %, 8-chloro-6-(trifluoromethyl)imidazo[1,2-a]pyridine-2-carboxylic acid about 1.72 a %, unreacted 2-chloro-5-methoxybenzenesulfonamide about 2.20 a % and Compound 1 about 91.9 a %.

The reaction mass was stirred at 25° C. and to this, water (360 mL) was charged at 25° C. over a period of 60 min. To the resultant reaction mixture, a solution of HCl (32 wt %, 191 g) in 200 mL water was added over a period of 45 min. During the HCl addition, the reaction mass became a clear solution initially and then gradually became a hazy liquid during the end of the addition. A temperature increase of 9° C. was observed during this addition. After the addition, the resultant reaction mass was heated to 55° C., stirred for 60 min, gradually cooled to 5° C., then stirred at 5° C. for 30 min and filtered. The wet cake was washed with water (3 times with 3100 mL) and vacuum-dried on a Büchner funnel. The vacuum-dried material was analyzed for the chloride content which indicated no significant amount of chloride salts present. The wet cake was washed with toluene (2×400 mL) and vacuum-dried on a Büchner funnel for about 12 hours. The crude product was obtained as 185 grams of an off-white solid. The toluene and ethyl acetate content in the product were 17.3 wt % and 0.855 wt %, respectively. The water content was 0.84 wt %. The HPLC purity of the crude product (wet sample) was 99.8 a % and 80.0 wt %. The yield based on HPLC wt % analysis was 85%.

$^1$H-NMR was consistent with Compound 1 [(DMSO-$d_6$) δ 3.86 (s, 3H), 7.30 (d, 1H), 7.57 (dd, 1H), 7.64 (d, 1H), 7.96 (d, 1H), 8.84 (s, 1H), 9.34 (d, 1H)] containing toluene. The molar ratio of toluene and Compound 1 was about 1.06 indicating a 1:1 toluene solvate. The pXRD diffraction pattern was consistent with the toluene solvate (Form TS) of Compound 1. The crude wet solid was used for form conversion studies.

Preparation Example 2

Preparation of Mixed Forms A and B of Compound 1

The toluene solvate of Compound 1 was prepared as described in Preparation Example 1 and was desolvated by drying in a vacuum oven (8-15 kPa absolute pressure) at 90° C. for 4 days. The toluene content in the product was 0.11 wt % and the water content was 0.09 wt %.

$^1$H-NMR was consistent with Compound 1 [(DMSO-$d_6$) δ 3.86 (s, 3H), 7.30 (d, 1H), 7.57 (dd, 1H), 7.64 (d, 1H), 7.96 (d, 1H), 8.84 (s, 1H), 9.34 (d, 1H)]. The purity by HPLC was 99.9 a % and 99.0 wt %. The DSC thermogram showed two endotherms with peak temperatures of 211.1° C. and 219.1° C. The pXRD pattern confirms that the material was crystalline and corresponded to a mixture of crystals of Form A and Form B.

Preparation Example 3

Conversion of the Toluene-Solvate of Compound 1 to Form A

To a 500 mL three-neck round-bottom flask equipped with overhead stirrer, oil bath, a Dean-Stark apparatus and temperature probe was charged 25 g of Compound 1 wet cake prepared according to Preparation Example 1 (toluene content=17.3 wt %) and water (75 mL) at 25° C. The resultant reaction mass was heated to 95° C. (reaction mass temperature) and maintained at 95-96° C. over a period of 5 hours while stirring at about 850 rpm. The water collected from the Dean-Stark apparatus was recycled to maintain about constant reaction volume while toluene was removed from the reaction mass. After about 3 hours no further distillation of toluene was observed. A slurry sample was taken from the reaction mass under agitation. The toluene and ethyl acetate content of the slurry was determined by GC analysis as 56 ppm and 17 ppm, respectively. About 10 mL of the sample was taken from the reaction mixture, cooled to 25° C., filtered and vacuum-dried on a Büchner funnel for 15 min. The wet cake showed about 429 ppm of toluene and 36 ppm of ethyl acetate. The wet cake was dried in a vacuum oven at 55° C. (8-15 kPa absolute pressure) for about 1 hour and analyzed by DSC and pXRD. Both DSC and pXRD data was consistent with Form A of Compound 1.

Since the portion of the sample from the reaction mass indicated the conversion to Form A, the entire reaction mass was filtered, dried in a vacuum oven (8-15 kPa absolute pressure) at 55° C. for 1 hour. The dried product was analyzed by pXRD and DSC. Both DSC and pXRD data was consistent with Form A of Compound 1.

Preparation Example 4

Additional Polymorph Conversion Studies of the Toluene-Solvate (Form TS) of Compound 1

Form-conversion experiments according to Preparative Example 3 were conducted with water, methanol and the mixture thereof as the suspension medium. The experimental conditions and apparatus used were as described in Preparative Example 3 unless otherwise noted. In each experiment 25 g of the wet cake of Compound 1 prepared according to Preparation Example 1 (toluene content=17.3 wt %) were used as starting material. The experimental conditions are summarized in Table 2. The conditions of Preparative Example 3 are included for reference. The suspensions were subjected to azeotropic distillation under reflux conditions to remove the toluene using the Dean-Stark apparatus. After 3 to 5 hours no more toluene was visibly removed and the resultant slurries were filtered, dried in a vacuum oven (8-15 kPa absolute pressure) at 55° C. for 1 hour and analyzed by DSC and pXRD. The DSC and pXRD data of all the examples listed in Table 2 were consistent with Form A of Compound 1.

TABLE 2

Experimental Conditions of Polymorph Conversion Studies and Resulting Form

| Example | Amount of Compound 1 (g) | Starting Polymorph Form | Volume of Water (mL) | Volume of Methanol (mL) | Slurry Temperature (° C.) | Polymorph Form Obtained |
|---------|--------------------------|-------------------------|----------------------|-------------------------|---------------------------|-------------------------|
| 3       | 25                       | TS                      | 75                   | —                       | 95-96                     | A                       |
| 4a      | 25                       | TS                      | 125                  | —                       | 95-96                     | A                       |
| 4b      | 25                       | TS                      | 175                  | —                       | 95-96                     | A                       |
| 4c      | 25                       | TS                      | 125                  | —                       | 95-96                     | A                       |
| 4d      | 25                       | TS                      | 100                  | 25                      | 95-96                     | A                       |
| 4e      | 25                       | TS                      | —                    | 100                     | 63                        | A                       |
| 4f      | 25                       | TS                      | 125                  | —                       | 85-87                     | A                       |
| 4g      | 25                       | TS                      | 125                  | —                       | 85-87                     | A                       |

Preparation Example 5

Solvent Screening to Prepare Various Crystal Forms of Compound 1

A set of solvents was evaluated for the preparation of various crystal forms including solvate forms of Compound 1. The starting material of Compound 1 was prepared according to Preparation Example 2. Aliquots of Compound 1 thus prepared were either dissolved or slurried in the selection of solvents listed in Table 3 and treated according to the following descriptions. The resulting dry materials were analyzed by $^1$H-NMR, pXRD, DSC and TGA. The endothermic DSC events and resulting crystal forms are also reported in Table 3.

In Example 5a, 1 g of Compound 1 was dissolved in 6.5 mL of acetone at 56° C. The solution was slowly cooled to about 5° C. over a period of 1 h. The resulting crystals were filtered, suction dried for 1 h and dried in a vacuum oven at 65° C. and 8 kPa absolute pressure for 12 h. Analysis by pXRD, DSC, TGA and $^1$H-NMR of the resulting material indicated Form A.

In Example 5b, 1 g of Compound 1 was slurried in 10 mL of methanol, refluxed for 3 h, filtered, cooled to about 25° C., suction dried for 1 h and dried in a vacuum oven at 70° C. and 8 kPa absolute pressure for 12 h. Analysis by pXRD, DSC, TGA and $^1$H-NMR of the resulting material indicated Form A.

In Example 5c, 1 g of Compound 1 was slurried in 10 mL of deionized water, refluxed for 3 h, cooled to about 25° C., filtered, suction dried for 1 h and dried in a vacuum oven at 70° C. and 8 kPa absolute pressure for 12 h. Analysis by pXRD, DSC, TGA and $^1$H-NMR of the resulting material indicated Form A.

In Example 5d, 1 g of Compound 1 was slurried in 10 mL of n-heptane, refluxed for 3 h, cooled to about 25° C., filtered, suction dried for 1 h and dried in a vacuum oven at 70° C. and 8 kPa absolute pressure for 12 h. Analysis by pXRD, DSC, TGA and $^1$H-NMR of the resulting material indicated Form A.

In Example 5e, 1 g of Compound 1 was dissolved in 14 mL of ethyl acetate at 65° C. The solution was cooled to 5° C. over a period of 1 h. The resulting crystals were filtered, suction dried for 1 h and dried in a vacuum oven at 65° C. and 8 kPa absolute pressure for 12 h. Analysis by pXRD, DSC, TGA and $^1$H-NMR of the resulting material indicated a solvate form containing ethyl acetate.

In Example 5f, 1 g of Compound 1 was refluxed in 10 mL of iso-propanol for 3 h, cooled to about 25° C., filtered, suction dried for 1 h and dried in a vacuum oven at 65° C. and 8 kPa absolute pressure for 12 h. Analysis by pXRD, DSC, TGA and $^1$H-NMR of the resulting material indicated a solvate form containing iso-propanol.

In Example 5g, 1 g of Compound 1 was refluxed in 10 mL of methyl tert-butyl ether for 3 h, cooled to about 25° C., filtered, suction dried for 1 h and dried in a vacuum oven at 65° C. and 8 kPa absolute pressure for 12 h. Analysis by pXRD, DSC, TGA and $^1$H-NMR of the resulting material indicated a solvate form containing methyl tert-butyl ether.

In Example 5h, 1 g of Compound 1 was dissolved in 12 mL of acetonitrile at 65° C. The solution was slowly cooled to 5° C. over a period of 4 h. The resulting crystals were filtered, suction dried for 1 h and dried in a vacuum oven at 65° C. and 8 kPa absolute pressure for 12 h. Analysis by pXRD, DSC, TGA and $^1$H-NMR of the resulting material indicated Form D.

In Example 5i, 1 g of Compound 1 was dissolved in 12 mL of tetrahydrofuran at 65° C. The solution was slowly cooled to 25° C. over a period of 4 h. The resulting crystals were filtered, suction dried for 1 h and dried in a vacuum oven at 65° C. and 8 kPa absolute pressure for 12 h. Analysis by pXRD, DSC, TGA and $^1$H-NMR of the resulting material indicated solvate form containing tetrahydrofuran.

In Example 5j, 1 g of Compound 1 was slurried in 12 mL of ethanol, refluxed for 3 h, cooled to about 25° C., filtered, suction dried for 1 h and dried in a vacuum oven at 70° C. and 8 kPa absolute pressure for 12 h. Analysis by pXRD, DSC, TGA and $^1$H-NMR of the resulting material indicated solvate form containing ethanol.

In Example 5k, 1 g of Compound 1 was slurried in 10 mL of decalin, heated at 120° C. for 3 h, cooled to about 25° C., filtered, suction dried for 1 h and dried in a vacuum oven at 90° C. and 8 kPa absolute pressure for 12 h. Analysis by pXRD, DSC, TGA and $^1$H-NMR of the resulting material indicated solvate form containing decalin.

In Example 5l, 1 g of Compound 1 was dissolved in 12.5 mL of methyl iso-butyl ketone at 65° C. The solution was cooled to about 25° C. over a period of 3 h. The resulting crystals were filtered, suction dried for 1 h and dried in a vacuum oven at 90° C. and 8 kPa absolute pressure for 12 h. Analysis by pXRD, DSC, TGA and $^1$H-NMR of the resulting material indicated solvate form containing methyl iso-butyl ketone.

In Example 5m, 1 g of Compound 1 was dissolved in 6 mL of mesitylene at 120° C. The resulting solution was slowly cooled to about 25° C. over a period of 4 h. The resulting crystals were filtered, suction dried for 1 h and dried in a vacuum oven at 90° C. and 8 kPa absolute pressure for 12 h. Analysis by pXRD, DSC, TGA and $^1$H-NMR of the resulting material indicated a mixture of Forms A and B.

In Example 5n, 1 g of Compound 1 was dissolved in 17 mL of toluene at 90° C. The resulting solution was slowly cooled to about 25° C. over a period of 4 h. The resulting crystals were filtered, suction dried for 1 h and dried in a vacuum oven at 90° C. and 8 kPa absolute pressure for 12 h. Analysis by pXRD, DSC, TGA and $^1$H-NMR of the resulting material indicated a solvate form containing toluene. The residual toluene was remaining in the product even after additional 12 hr drying under the above drying conditions.

In Example 5o, 1 g of Compound 1 was dissolved in 15 mL of dichloromethane at 25° C. The resulting solution was slowly cooled to about 5° C. and maintained at 5° C. for 30 min. The resulting crystals were filtered, suction dried for 1 h and dried in a vacuum oven at 65° C. and 8 kPa absolute pressure for 12 h. Analysis by pXRD, DSC, TGA and $^1$H-NMR of the resulting material indicated Form B.

In Example 5p, 1 g of Compound 1 was slurried in 10 mL of tetralin at 120° C. for 3 h, slowly cooled to about 25° C., filtered, suction dried for 1 h and dried in a vacuum oven at 90° C. and 8 kPa absolute pressure for 12 h. Analysis by pXRD, DSC, TGA and $^1$H-NMR of the resulting material indicated a mixture of Forms A and B.

In Example 5q, 1 g of Compound 1 was dissolved in 9 mL of 1,4-dioxane at 65° C. The resulting solution was slowly cooled to about 25° C. over 4 h and maintained at 25° C. for 12 h. The resulting crystals were filtered, suction dried for 1 h and dried in a vacuum oven at 70° C. and 8 kPa absolute pressure for 12 h. Analysis by pXRD, DSC, TGA and $^1$H-NMR of the resulting material indicated a solvate form containing 1,4-dioxane.

In Example 5r, 1 g of Compound 1 was dissolved in 7 mL of acetic acid at 80° C. The resulting solution was slowly cooled to about 25° C. over 4 h and maintained at 25° C. for 12 h. The resulting crystals were filtered, suction dried for 1 h and dried in a vacuum oven at 70° C. and 8 kPa absolute pressure for 12 h. Analysis by pXRD, DSC, TGA and $^1$H-NMR of the resulting material indicated Form D.

In Example 5s, 1 g of Compound 1 was dissolved in 7 mL of iso-propyl acetate at 70° C. The resulting solution was slowly cooled to about 25° C. over 4 h and maintained at 25° C. for 12 h. The resulting crystals were filtered, suction dried for 1 h and dried in a vacuum oven at 70° C. and 8 kPa absolute pressure for 12 h. Analysis by pXRD, DSC, TGA and $^1$H-NMR of the resulting material indicated a solvate form containing iso-propyl acetate.

In Example 5t, 1 g of Compound 1 was slurried in 10 mL of o-xylene at 100° C., cooled to about 25° C., filtered, suction dried for 1 h and dried in a vacuum oven at 90° C. and 8 kPa absolute pressure for 12 h. Analysis by pXRD, DSC, TGA and $^1$H-NMR of the resulting material indicated a mixture of Forms A and B.

TABLE 3

Crystal Form Conversion Studies Using Various Solvents

| Ex. No. | Solvent | Polymorph Form Obtained | DSC Endotherm 1 (° C.) | DSC Endotherm 2 (° C.) |
|---|---|---|---|---|
| 5a | acetone | A | 210.9 | 218.9 |
| 5b | methanol | A | 209.9 | 218.7 |
| 5c | water | A | 212.1 | 218.7 |
| 5d | n-heptane | A | 212.8 | 219.1 |
| 5e | ethyl acetate | Solvate | 210.8 | 218.6 |
| 5f | iso-propanol | Solvate | 211.4 | 218.3 |
| 5g | methyl tert-butyl ether | Solvate | 210.3 | 218.4 |
| 5h | acetonitrile | D | 212.8 | 219.4 |
| 5i | Tetrahydrofuran | Solvate | 210.5 | 218.6 |
| 5j | ethanol | Solvate | 208.2 | 218.7 |
| 5k | decalin | Solvate | 211.1 | 218.3 |
| 5l | methyl iso-butyl ketone | Solvate | 211.6 | 218.9 |
| 5m | mesitylene | A + B | 211.8 | 218.4 |
| 5n | toluene | Solvate | 210.6 | 218.8 |
| 5o | dichloromethane | B | 210.5 | 218.5 |
| 5p | tetralin | A + B | 212.9 | 219.0 |

TABLE 3-continued

Crystal Form Conversion Studies Using Various Solvents

| Ex. No. | Solvent | Polymorph Form Obtained | DSC Endotherm 1 (° C.) | DSC Endotherm 2 (° C.) |
|---|---|---|---|---|
| 5q | 1,4-dioxane | Solvate | 210.8 | 218.9 |
| 5r | acetic acid | D | 213.1 | 219.5 |
| 5s | iso-propyl acetate | Solvate | 211.6 | 218.9 |
| 5t | o-xylene | A + B | 212.0 | 218.6 |

Preparation Example 6

Preparation of Polymorph Form D of Compound 1

Polymorph Form D of Compound 1 was prepared by heating Compound 1 prepared according to Preparation Example 2 with acetonitrile at 65° C. for 5 minutes. The clear solution obtained was gradually cooled to 5° C. over 4 hours and maintained at that temperature for 12 hours without disturbance. The crystals formed were filtered and dried at 65° C. in a vacuum oven (8 kPa absolute pressure) for 12 hours. The isolated solid was found to have a unique pXRD diffraction pattern indicating a distinct crystal form (polymorph Form D).

Form D was also prepared according the above procedure using acetic acid as the solvent as evidenced by displaying the same pXRD pattern. Both the sample crystallized from acetonitrile and acetic acid were also analyzed by single crystal XRD as described in the Characterization Examples below.

Preparation Example 7

Stability of a Mixture of Crystal Forms A and B in a Liquid Formulation

The mixture of polymorphs Form A and Form B of Compound 1 was prepared as described in Preparation Example 2. The presence of both polymorph forms was confirmed by pXRD.

A suspension concentrate Formulation X containing Compound 1 of mixed polymorph Forms A and B was prepared. The composition of Formulation X is given in the table below. All ingredients were combined in the order of ingredients listed in the table to yield a total amount of 6.5 grams. The mixture of combined ingredients was milled with an attritor mill in a 30 ml size flask equipped with a variable-speed overhead impeller using 14.3 grams of 0.8 to 1.0 mm sized glass beads. The flask content was agitated at room temperature for 5 min at 4000 rpm followed by 13 min at 6000 rpm. The resulting formulation was evaluated under a light microscope (Leica, model DM LS) at 400 to 1000-fold magnification to evaluate the homogeneity, size and shape of the particles of Compound 1 in the formulation. The particles were found to be of irregular shape and in the narrow range of about 3 to 10 μm. The sample was left standing for about 15 hours at room temperature and then reexamined under the microscope; it was found that larger cubical crystals in the size range between about 5 to 30 μm had formed. Also, clusters of dentritic crystals of a length between about 50 to 200 μm had formed. Such changes in crystal size and morphology constitutes an undesirable formulation instability which may result in undesired effects such as the active compound sedimenting out or the larger crystals not providing the full extend of bioefficacy owing to their reduced specific surface area.

The formulation sample, after standing for a total of 18 hours at room temperature, was re-milled for 45 min at 6000 rpm using the same equipment and conditions as described above. The observation under the microscope showed that the particles of Compound 1 were well dispersed in the size range of about 3 to 10 nm. The sample was split and stored for 14 days at room temperature and at 54° C., respectively. The reexamination of the two stored samples under the microscope showed no signs of crystal growth or change in morphology for either storage temperature indicating good particle size stability in the formulation. The concentration of Compound 1 in the samples stored at room temperature and 54° C. were determined by HPLC as 49.7 wt % and 51.2 wt %, respectively, indicating good chemical stability in the formulation.

To determine the crystal form of Compound 1 in the formulation sample that had been re-milled after crystal growth, Compound 1 was separated from the formulation as follows. An aliquot of the formulation (0.72 grams) was centrifuged in a 1.5 ml centrifuge tube for 6 cycles of 30 min each. After each centrifugation the supernatant was removed, replaced with deionized water and the tube content was thoroughly mixed. After the final centrifugation cycle the supernatant was discarded and the solids were dried at 40° C. for about 70 hours. Analysis by pXRD and DSC of the resulting material indicated pure polymorph Form A.

Formulation Example X

| Ingredient | Concentration (wt %) |
|---|---|
| water | 40.15 |
| silicones | 0.3 |
| xanthan gum | 0.2 |
| attapulgite clay | 0.5 |
| biocide | 0.05 |
| propylene glycol | 1.5 |
| glycerol | 3.0 |
| methylmethacrylate ethoxylated copolymer | 3.0 |
| ethylene oxide/propylene oxide block copolymer and ethoxylated alcohol | 2.0 |
| polymorph Forms A and B of Compound 1 | 49.3 |

Preparation Example 8

Preparation and Isolation of 8-chloro-6-(trifluoromethyl)imidazo[1,2-a]pyridine-2-carbonyl chloride To a 250 mL four neck round bottom flask, was charged toluene (50 mL), N-formyl piperidine (0.177 g, 1.6 mmol) and thionyl chloride (3.37 g, 27.8 mmol) at 23-25° C. under a nitrogen atmosphere. The resultant reaction mass was heated to 82° C. over a period of 20 min and to this 8-chloro-6-(trifluoromethyl)imidazo[1,2-a]pyridine-2-carboxylic acid (5.0 g, 18.6 mmol) was added portion wise over a period of 25 min. Additional toluene (25 mL) was also added. During the addition of the acid, the reaction mass changed from a slurry to a pale green solution liberating HCl gas. The resultant mass was heated to 90° C. and stirred for 90 min and the progress of the reaction was monitored by HPLC (0.5 mL of the reaction mass was diluted with 3 mL of methanol and analyzed for the formation of acid chloride as its corresponding methyl ester). After 90 min, HPLC analysis (230 nm) indicated the unreacted acid 0.32 A % and the methyl ester 99.24 A %. The resultant reaction mass was distilled at ~109° C.

(mass temperature) at atmospheric pressure over a period of 30 min to remove the toluene-thionyl chloride mixture (~50 mL). During the distillation the reaction mass turned dark brown. The reaction mass was gradually cooled to 30° C. over a period of 30 mins and a sample was analyzed by HPLC. The HPLC (at 230 nm) analysis indicated the unreacted acid ~0.33% and the formation of methyl ester ~99.12%. The title acid chloride was completely dried at 50° C. for 30 min under vacuum with a stream of nitrogen flow, to remove residual toluene and analyzed by HPLC and $^1$H NMR. The title acid chloride was isolated as a grey solid (6.5 g). HPLC purity (230 nm) of 95.60% AP (as methyl ester).

$^1$H-NMR (CDCl$_3$) δ 7.57 (s, 1H), 8.53 (s, 1H), 8.56 (s, 1H).
$^1$H-NMR (DMSO-d$_6$) δ 7.90 (s, 1H), 8.68 (s, 1H), 9.30 (s, 1H).

Characterization Example 1

X-Ray Powder Diffraction for Compound 1 Polymorph Form A

Powder X-ray diffraction was used to identify the crystalline phases of various samples of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu-K(alpha) (45 kV, 40 mA). Data were collected at room temperature from 3 to 50 degrees 2-theta using a continuous scan with an equivalent step size of 0.02 degrees and a count time of 320 seconds per step in theta-theta geometry. Samples were ground with an agate mortar and pestle as needed and prepared on low background amorphous silica specimen holders as a thin layer of powdered material. MDI/Jade software version 9.1 is used with the International Committee for Diffraction Data database PDF4+2008 for phase identification. Cu-K(alpha1) X-ray diffraction maxima for Form A of Compound 1 were calculated using the MDI/Jade "Find Peaks" routine and are listed Table 4.

TABLE 4

| 2θ X-ray Maxima (in degrees) for Polymorph Form A of Compound 1 |
| --- |
| 2θ |
| 11.651 |
| 12.854 |
| 13.705 |
| 14.056 |
| 15.426 |
| 18.286 |
| 18.836 |
| 19.789 |
| 21.026 |
| 21.543 |
| 23.097 |
| 23.582 |
| 24.285 |
| 24.584 |
| 24.954 |
| 25.604 |
| 25.973 |
| 26.490 |
| 27.308 |
| 27.611 |
| 27.995 |
| 29.131 |
| 29.764 |
| 30.367 |
| 30.652 |

TABLE 4-continued

| 2θ X-ray Maxima (in degrees) for Polymorph Form A of Compound 1 |
| --- |
| 2θ |
| 31.905 |
| 32.657 |
| 33.042 |
| 34.629 |
| 35.028 |
| 35.614 |
| 35.982 |
| 36.967 |
| 37.703 |
| 37.956 |
| 38.607 |
| 38.992 |
| 39.875 |
| 40.443 |
| 41.632 |
| 42.451 |
| 42.935 |
| 43.538 |
| 44.089 |
| 44.740 |
| 45.926 |
| 46.644 |
| 47.279 |
| 47.813 |
| 48.167 |
| 48.648 |
| 49.118 |
| 49.502 |

Characterization Example 2

Simulated X-Ray Powder Diffraction Pattern for Compound 1 Polymorph Form B

A simulated powder pattern was calculated from the atomic coordinates and cell parameters determined from the single crystal structure for polymorph Form B of Compound 1. This is based on data collected at −100° C. The X-ray pattern was calculated using the Cambridge Mercury program with Cu wavelength (0.154056 nm), 3 to 50 degrees 2-theta and a step size of 0.02 degrees. Peak positions were selected from the calculated pattern using the MDI/Jade software version 9. Cu-K(alpha1) X-ray diffraction maxima for Form B of Compound 1 were calculated using the MDI/Jade "Find Peaks" routine and are listed Table 5.

TABLE 5

| 2θ X-ray Maxima (in degrees) for Polymorph Form B of Compound 1 |
| --- |
| 2θ |
| 7.998 |
| 8.362 |
| 9.460 |
| 10.417 |
| 10.938 |
| 11.997 |
| 12.339 |
| 12.738 |
| 13.083 |
| 14.020 |
| 14.443 |
| 15.259 |
| 15.778 |
| 16.038 |
| 16.341 |

TABLE 5-continued

2θ X-ray Maxima (in degrees)
for Polymorph Form B of Compound 1

| 2θ |
|---|
| 16.603 |
| 17.219 |
| 18.120 |
| 18.683 |
| 18.981 |
| 19.502 |
| 20.320 |
| 20.999 |
| 21.880 |
| 22.718 |
| 23.082 |
| 23.341 |
| 23.979 |
| 24.583 |
| 24.822 |
| 25.060 |
| 25.978 |
| 26.519 |
| 27.283 |
| 27.581 |
| 28.242 |
| 28.642 |
| 29.139 |
| 29.657 |
| 30.177 |
| 30.520 |
| 30.921 |
| 31.479 |
| 31.958 |
| 32.382 |
| 32.758 |
| 32.961 |
| 33.342 |
| 33.943 |
| 34.400 |
| 34.683 |
| 35.161 |
| 35.358 |
| 36.040 |
| 36.463 |
| 37.442 |
| 37.903 |
| 38.340 |
| 38.537 |
| 39.340 |
| 39.742 |
| 39.942 |
| 40.241 |
| 41.001 |
| 42.559 |
| 42.782 |
| 43.139 |
| 43.478 |
| 44.259 |
| 45.199 |
| 45.438 |
| 46.102 |
| 46.399 |
| 47.100 |
| 48.120 |
| 49.097 |

Characterization Example 3

Simulated X-Ray Powder Diffraction Pattern for Compound 1 Polymorph Form C

A simulated powder pattern was calculated from the atomic coordinates and cell parameters determined from the single crystal structure for polymorph Form C of Compound 1. This is based on data collected at −100° C. The X-ray pattern was calculated using the Cambridge Mercury program with Cu wavelength (0.154056 nm), 3 to 50 degrees 2-theta and a step size of 0.02 degrees. Peak positions were selected from the calculated pattern using the MDI/Jade software version 9. Cu-K(alpha1) X-ray diffraction maxima for Form C of Compound 1 were calculated using the MDI/Jade "Find Peaks" routine and are listed Table 6.

TABLE 6

2θ X-ray Maxima (in degrees)
for Polymorph Form C of Compound 1

| 2θ |
|---|
| 6.181 |
| 7.222 |
| 7.603 |
| 8.363 |
| 8.657 |
| 9.377 |
| 11.860 |
| 12.421 |
| 13.041 |
| 13.583 |
| 14.479 |
| 15.041 |
| 15.442 |
| 15.777 |
| 16.423 |
| 16.859 |
| 17.360 |
| 17.697 |
| 18.340 |
| 18.583 |
| 19.098 |
| 19.420 |
| 19.899 |
| 20.360 |
| 20.760 |
| 21.161 |
| 21.585 |
| 22.120 |
| 22.420 |
| 22.996 |
| 23.542 |
| 23.880 |
| 24.379 |
| 24.701 |
| 25.181 |
| 25.622 |
| 25.837 |
| 26.300 |
| 26.557 |
| 27.160 |
| 27.520 |
| 28.180 |
| 28.661 |
| 29.281 |
| 29.579 |
| 30.001 |
| 30.502 |
| 30.761 |
| 31.279 |
| 31.878 |
| 32.499 |
| 33.061 |
| 33.479 |
| 33.737 |
| 34.418 |
| 34.662 |
| 35.541 |
| 35.961 |
| 36.239 |
| 36.618 |
| 36.920 |
| 37.480 |
| 37.719 |
| 38.239 |
| 38.457 |
| 38.956 |

TABLE 6-continued

2θ X-ray Maxima (in degrees)
for Polymorph Form C of Compound 1

| 2θ |
|---|
| 39.378 |
| 39.601 |
| 40.360 |
| 41.059 |
| 41.640 |
| 41.861 |
| 42.080 |
| 42.662 |
| 43.141 |
| 44.44 |
| 44.899 |
| 45.141 |
| 46.300 |
| 47.319 |
| 47.639 |
| 48.239 |
| 48.825 |

Characterization Example 4

Simulated X-Ray Powder Diffraction Pattern for Compound 1 Polymorph Form D

A simulated powder pattern was calculated from the atomic coordinates and cell parameters determined from the single crystal structure for polymorph Form D of Compound 1. This is based on data collected at −100° C. The X-ray pattern was calculated using the Cambridge Mercury program with Cu wavelength (0.154056 nm), 3 to 50 degrees 2-theta and a step size of 0.02 degrees. Peak positions were selected from the calculated pattern using the MDI/Jade software version 9. Cu-K(alpha1) X-ray diffraction maxima for Form D of Compound 1 were calculated using the MDI/Jade "Find Peaks" routine and are listed Table 7.

TABLE 7

2θ X-ray Maxima (in degrees)
for Polymorph Form D of Compound. 1

| 2θ |
|---|
| 5.981 |
| 10.342 |
| 11.641 |
| 12.263 |
| 12.520 |
| 14.598 |
| 14.840 |
| 15.378 |
| 15.620 |
| 16.160 |
| 17.821 |
| 18.001 |
| 18.478 |
| 19.320 |
| 20.778 |
| 21.281 |
| 22.583 |
| 23.320 |
| 24.099 |
| 24.679 |
| 25.121 |
| 25.279 |
| 25.682 |
| 26.120 |
| 26.922 |
| 27.497 |

TABLE 7-continued

2θ X-ray Maxima (in degrees)
for Polymorph Form D of Compound. 1

| 2θ |
|---|
| 28.460 |
| 28.717 |
| 28.921 |
| 29.162 |
| 29.516 |
| 29.801 |
| 29.943 |
| 30.143 |
| 31.219 |
| 31.600 |
| 32.343 |
| 32.658 |
| 33.060 |
| 33.442 |
| 34.420 |
| 35.421 |
| 36.683 |
| 37.023 |
| 37.383 |
| 37.858 |
| 39.200 |
| 39.521 |
| 40.160 |
| 40.461 |
| 41.160 |
| 41.556 |
| 42.641 |
| 43.620 |
| 46.103 |
| 46.420 |
| 47.980 |
| 48.797 |

Characterization Example 5

X-Ray Powder Diffraction Pattern for Compound 1 Polymorph Form TS

Powder X-ray diffraction was used to characterize the toluene solvate polymorph form (Polymorph Form TS) of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu-K(alpha) (45 kV, 40 mA). Data were collected at room temperature from 3 to 50 degrees 2-theta using a continuous scan with an equivalent step size of 0.02 degrees and a count time of 320 seconds per step in theta-theta geometry. Samples were lightly ground with an agate mortar and pestle as needed and prepared on low background silicon specimen holders as a thin layer of powdered material. MDI/Jade software version 9.1 was used with the International Committee for Diffraction Data database PDF4+2008 for phase identification. Cu-K(alpha1) X-ray diffraction maxima for Form TS of Compound 1 were calculated using the MDT/Jade "Find Peaks" routine and are listed Table 8.

TABLE 8

2θ X-ray Maxima (in degrees)
for Polymorph Form TS of Compound 1

| 2θ |
|---|
| 6.889 |
| 8.608 |
| 9.997 |

TABLE 8-continued

2θ X-ray Maxima (in degrees)
for Polymorph Form TS of Compound 1

| 2θ |
|---|
| 11.433 |
| 12.871 |
| 13.606 |
| 14.508 |
| 14.908 |
| 15.728 |
| 16.481 |
| 16.998 |
| 17.433 |
| 18.603 |
| 19.053 |
| 20.325 |
| 21.643 |
| 22.429 |
| 23.316 |
| 24.451 |
| 25.672 |
| 26.942 |
| 27.945 |
| 28.913 |
| 30.951 |
| 32.222 |
| 32.671 |
| 33.561 |
| 33.994 |
| 34.528 |
| 36.114 |
| 36.906 |
| 37.452 |
| 38.323 |
| 39.057 |
| 40.711 |
| 41.548 |
| 42.015 |
| 43.869 |
| 45.173 |
| 46.092 |
| 47.514 |
| 48.148 |

Characterization Example 6

Single Crystal X-Ray Diffraction for Polymorph Form A of Compound 1

Suitable single crystals for polymorph Form A were grown from slow evaporation of methanol. A colorless irregular block with approximate dimensions of 0.10×0.10×0.04 mm was chosen for data collection and mounted on a polymer loop. Single crystal data was collected using a Bruker Platform goniometer with an Apex-II detector. The diffractometer was equipped with an incident beam monochromator using Mo-Kα radiation ($\lambda$=0.71073 Å) and a monocap collimator. The crystals were cooled in a −100° C. nitrogen flow during data collection.

The data were indexed and integrated using the Apex-II suite of programs including Sainplus and SADABS. The triclinic cell parameters were determined to be: a=8.483(3) Å, b=10.004(3) Å, c=11.638(4) Å, alpha=86.690(5)°, beta=87.984(5)°, gamma=65.114(4)°, volume=894.4(5) Å$^3$. The space group was determined to be P-1. The molecular weight was 468.23 g/mol giving a calculated density of 1.739 g/cm$^3$, and μ(Mo)=0.54 mm$^{-1}$ for Z=2. Data reduction led to 3684 unique data from a two-theta range=3.50 to 53.12°. Structure solution and refinements were performed using the Shelxtl program suite with refinement based on F$^2$ with scattering factors from Int. Tab. Vol C Tables 4.2.6.8 and 6.1.1.4.

The final refinement statistics include a data/parameter ratio=13.90, goodness-of-fit on F$^2$=1.02, R indices[I>4sigma (I)]R1=0.0506, wR2=0.0977, R indices (all data) R1=0.0951, wR2=0.1141, max difference peak and hole=0.310 and −0.379 e/Å$^3$. The atomic fractional coordinates (×10$^4$) and equivalent isotropic displacement parameters are listed in Tables 9 and 10. U (eq) is defined as one third of the trace of the orthogonalized Uij tensor. The estimated standard deviations are shown in parentheses.

TABLE 9

Atomic Coordinates (×10$^4$) and Equivalent Isotropic Displacement Parameters (A$^2$ × 10$^3$) for Compound 1 Polymorph Form A

| Atom | x | y | z | U(eq) |
|---|---|---|---|---|
| Cl(1) | −561(1) | −1094(1) | 6924(1) | 43(1) |
| Cl(2) | 2856(2) | 1915(1) | 10437(1) | 62(1) |
| S(1) | 4552(1) | 2760(1) | 8088(1) | 32(1) |
| F(1) | −6506(2) | 2428(2) | 4590(2) | 44(1) |
| F(2) | −5576(3) | 3508(2) | 3277(2) | 49(1) |
| F(3) | −4749(3) | 1156(2) | 3306(2) | 54(1) |
| O(1) | 1474(3) | 4766(2) | 6746(2) | 37(1) |
| O(2) | 5691(3) | 1379(3) | 8579(2) | 49(1) |
| O(3) | 5180(3) | 3493(3) | 7231(2) | 45(1) |
| N(1) | 2988(3) | 2445(3) | 7517(2) | 30(1) |
| N(2) | 403(3) | 1635(3) | 6768(2) | 30(1) |
| N(4) | −1720(3) | 2916(3) | 5502(2) | 26(1) |
| C(1) | 1618(4) | 3510(4) | 6917(3) | 29(1) |
| C(2) | 373(4) | 2995(3) | 6476(3) | 27(1) |
| C(3) | −911(4) | 3799(4) | 5719(3) | 28(1) |
| C(5) | −891(4) | 1609(3) | 6177(3) | 27(1) |
| C(6) | −1524(4) | 513(3) | 6103(3) | 30(1) |
| C(7) | −2841(4) | 743(4) | 5388(3) | 32(1) |
| C(8) | −3613(4) | 2086(4) | 4711(3) | 29(1) |
| C(9) | −3054(4) | 3157(4) | 4776(3) | 30(1) |
| C(10) | −5083(4) | 2298(4) | 3966(3) | 36(1) |
| C(11) | 3454(4) | 4034(3) | 9144(3) | 26(1) |
| C(12) | 2725(4) | 3667(4) | 10134(3) | 36(1) |
| C(13) | 1858(5) | 4738(5) | 10897(3) | 51(1) |
| C(14) | 1684(5) | 6159(5) | 10692(4) | 56(1) |
| C(15) | 2388(4) | 6525(4) | 9708(4) | 44(1) |
| C(16) | 3282(4) | 5461(3) | 8930(3) | 33(1) |
| O(4) | 2424(7) | 7917(6) | 9159(6) | 46(2) |
| C(17) | 1161(9) | 9199(8) | 9661(7) | 50(2) |
| O(4') | 2039(6) | 7914(5) | 9778(5) | 39(2) |
| C(17') | 2358(9) | 8429(8) | 8874(6) | 40(2) |

TABLE 10

Hydrogen Coordinates (×10$^4$) and Isotropic Displacement Parameters (A$^2$ × 10$^3$) for Compound 1 Polymorph Form A

| Atom | x | y | z | U(eq) |
|---|---|---|---|---|
| H(3A) | −1180 | 4749 | 5415 | 34 |
| H(7A) | −3248 | 18 | 5337 | 38 |
| H(9A) | −3563 | 4037 | 4338 | 36 |
| H(13A) | 1379 | 4498 | 11565 | 61 |
| H(14A) | 1090 | 6873 | 11219 | 67 |
| H(16A) | 3765 | 5705 | 8266 | 39 |
| H(1) | 3010(40) | 1620(40) | 7630(30) | 26(9) |
| H(17A) | 1226 | 10061 | 9297 | 75 |
| H(17B) | 1380 | 9161 | 10469 | 75 |
| H(17C) | 23 | 9242 | 9556 | 75 |
| H(17D) | 2567 | 9456 | 8956 | 61 |
| H(17E) | 2461 | 8300 | 8144 | 61 |
| H(17F) | 4095 | 7877 | 8916 | 61 |

Characterization Example 7

Single Crystal X-Ray Diffraction for Polymorph Form B of Compound 1

Suitable single crystals of polymorph Form B of Compound 1 were grown from thermal gradient sublimation at 160° C. A colorless prism with approximate dimensions of 0.40×0.26×0.13 mm was chosen for data collection and mounted on a polymer loop. Single crystal data was collected using a Bruker Platform goniometer with an Apex-II detector. The diffractometer is equipped with an incident beam monochromator using Mo-Kα radiation ($\lambda$=0.71073 Å) and a monocap collimator. The crystals were cooled in a −100° C. nitrogen flow during data collection.

The data were indexed and integrated using the Apex-II suite of programs including Sainplus and SADABS. The triclinic cell parameters were determined to be: a=11.6429 (17) Å, b=12.0937(17) Å, c=14.859(2) Å, alpha=109.171 (2)°, beta=92.359(2)°, gamma=106.342(2)°, volume=1875.6 (5) Å$^3$. The space group was determined to be P-1. The molecular weight was 468.23 g/mol giving a calculated density of 1.658 g/cm$^3$, and μ(Mo)=0.52 mm$^{-1}$ for Z=4. Data reduction led to 8320 unique data from a two-theta range=2.94 to 54.50°. Structure solution and refinements were performed using the Shelxtl program suite with refinement based on F$^2$ with scattering factors from Int. Tab. Vol C Tables 4.2.6.8 and 6.1.1.4. The final refinement statistics include a data/parameter ratio=13.80, goodness-of-fit on F$^2$=1.06, R indices[1>4sigma(I)]R1=0.0446, wR2=0.1012, R indices (all data) R1=0.0732, wR2=0.1120, max difference peak and hole=0.354 and −0.453 e/Å$^3$. The atomic fractional coordinates (×10$^4$) and equivalent isotropic displacement parameters are listed in Tables 11 and 12. U (eq) is defined as one third of the trace of the orthogonalized Uij tensor. The estimated standard deviations are shown in parentheses.

TABLE 11

Atomic Coordinates (×10$^4$) and Equivalent Isotropic Displacement Parameters (A$^2$ × 10$^3$) for Compound 1 Polymorph Form B

| Atom | x | y | z | U(eq) |
|---|---|---|---|---|
| Cl(1) | 9215(1) | 2511(1) | 5201(1) | 40(1) |
| Cl(2) | 12637(1) | 398(1) | 6790(1) | 43(1) |
| Cl(21) | 9857(1) | 8175(1) | 2427(1) | 56(1) |
| Cl(22) | 7769(1) | 1721(1) | 1632(1) | 46(1) |
| S(1) | 14843(1) | 2991(1) | 7570(1) | 27(1) |
| S(21) | 5885(1) | 3011(1) | 2823(1) | 29(1) |
| F(1) | 11222(2) | 5634(2) | 2620(1) | 51(1) |
| F(2) | 9386(2) | 5058(2) | 2883(1) | 47(1) |
| F(3) | 10074(2) | 3794(2) | 1859(1) | 50(1) |
| F(21) | 9708(2) | 8703(2) | −1033(2) | 50(1) |
| F(22) | 8228(2) | 9345(2) | −592(1) | 51(1) |
| F(23) | 7908(2) | 7651(2) | −1780(1) | 50(1) |
| O(1) | 15222(2) | 3594(2) | 5823(1) | 32(1) |
| O(2) | 15978(2) | 3936(2) | 7792(1) | 33(1) |
| O(3) | 14209(2) | 2833(2) | 8341(1) | 35(1) |
| O(4) | 17604(2) | 649(2) | 6058(2) | 40(1) |
| O(21) | 4965(2) | 3179(2) | 983(1) | 33(1) |
| O(22) | 4817(2) | 3289(2) | 3094(2) | 37(1) |
| O(23) | 6841(2) | 3215(2) | 3546(1) | 36(1) |
| O(24) | 2664(2) | −1058(2) | 1334(1) | 41(1) |
| N(1) | 13905(2) | 3245(2) | 6861(2) | 28(1) |
| N(2) | 12055(2) | 3283(2) | 5595(2) | 27(1) |
| N(4) | 12302(2) | 4104(2) | 4441(2) | 26(1) |
| N(21) | 6521(3) | 3877(2) | 2211(2) | 30(1) |
| N(22) | 7666(3) | 5770(2) | 1618(2) | 29(1) |
| N(24) | 7309(2) | 5998(2) | 203(2) | 26(1) |
| C(1) | 14219(3) | 3510(2) | 6049(2) | 25(1) |
| C(2) | 13250(3) | 3662(3) | 5486(2) | 25(1) |
| C(3) | 13421(3) | 4156(3) | 4779(2) | 27(1) |

TABLE 11-continued

Atomic Coordinates (×10$^4$) and Equivalent Isotropic Displacement Parameters (A$^2$ × 10$^3$) for Compound 1 Polymorph Form B

| Atom | x | y | z | U(eq) |
|---|---|---|---|---|
| C(5) | 11482(3) | 3544(2) | 4942(2) | 26(1) |
| C(6) | 10240(3) | 3303(3) | 4650(2) | 29(1) |
| C(7) | 9881(3) | 3673(3) | 3946(2) | 32(1) |
| C(8) | 10766(3) | 4306(3) | 3503(2) | 30(1) |
| C(9) | 11950(3) | 4518(3) | 3741(2) | 29(1) |
| C(10) | 10365(3) | 4704(3) | 2724(2) | 35(1) |
| C(11) | 15046(3) | 1589(2) | 6871(2) | 26(1) |
| C(12) | 14097(3) | 475(3) | 6557(2) | 32(1) |
| C(13) | 14335(3) | −598(3) | 6047(2) | 34(1) |
| C(14) | 15493(3) | −580(3) | 5873(2) | 34(1) |
| C(15) | 16435(3) | 522(3) | 6182(2) | 30(1) |
| C(16) | 16193(3) | 1609(3) | 6679(2) | 29(1) |
| C(17) | 17922(4) | −453(3) | 5647(3) | 46(1) |
| C(21) | 5955(3) | 3886(2) | 1383(2) | 28(1) |
| C(22) | 6678(3) | 4840(2) | 1042(2) | 26(1) |
| C(23) | 6447(3) | 4944(3) | 175(2) | 28(1) |
| C(25) | 8026(3) | 6471(3) | 1101(2) | 28(1) |
| C(26) | 8967(3) | 7601(3) | 1327(2) | 34(1) |
| C(27) | 9146(3) | 8181(3) | 676(2) | 36(1) |
| C(28) | 8374(3) | 7646(3) | −225(2) | 31(1) |
| C(29) | 7485(3) | 6573(3) | −461(2) | 28(1) |
| C(30) | 8560(3) | 8321(3) | −914(2) | 36(1) |
| C(31) | 5448(3) | 1474(2) | 2009(2) | 26(1) |
| C(32) | 6258(3) | 918(3) | 1535(2) | 30(1) |
| C(33) | 5848(3) | −318(3) | 975(2) | 36(1) |
| C(34) | 4655(3) | −1007(3) | 883(2) | 34(1) |
| C(35) | 3848(3) | −459(3) | 1359(2) | 30(1) |
| C(36) | 4245(3) | 794(3) | 1904(2) | 29(1) |
| C(37) | 2241(4) | −2352(3) | 810(3) | 52(1) |

TABLE 12

Hydrogen Coordinates (×10$^4$) and Isotropic Displacement Parameters (A$^2$ × 10$^3$) for Compound 1 Polymorph Form B

| Atom | x | y | z | U(eq) |
|---|---|---|---|---|
| H(1) | 13230(30) | 3160(20) | 6978(18) | 10(7) |
| H(3) | 14080(30) | 4460(30) | 4550(20) | 24(8) |
| H(7) | 9040(30) | 3560(30) | 3780(20) | 44(10) |
| H(9) | 12600(20) | 4960(20) | 3477(18) | 16(7) |
| H(13) | 13680(30) | −1300(30) | 5870(20) | 28(8) |
| H(14) | 15620(30) | −1310(30) | 5560(20) | 50(10) |
| H(16) | 16810(30) | 2340(30) | 6860(20) | 29(8) |
| H(17) | 18850(40) | −150(30) | 5690(20) | 47(10) |
| H(17A) | 17470(30) | −980(30) | 5000(30) | 47(10) |
| H(17B) | 17690(30) | −990(30) | 6000(30) | 49(10) |
| H(21) | 7250(30) | 4290(30) | 2360(20) | 50(11) |
| H(23) | 5860(30) | 4480(20) | −310(20) | 21(7) |
| H(27) | 9760(30) | 8870(30) | 810(20) | 45(10) |
| H(29) | 6950(30) | 6140(30) | −1030(20) | 36(9) |
| H(33) | 6400(30) | −650(30) | 670(20) | 43(10) |
| H(34) | 4340(30) | −1920(30) | 500(20) | 46(9) |
| H(36) | 3700(30) | 1180(30) | 2210(20) | 32(8) |
| H(37) | 1360(40) | −2660(30) | 890(30) | 60(12) |
| H(37A) | 2670(30) | −2750(30) | 1070(30) | 50(11) |
| H(37B) | 2260(40) | −2520(40) | 100(30) | 75(13) |

Characterization Example 8

Single Crystal X-Ray Diffraction for Polymorph Form C of Compound 1

Suitable single crystals of polymorph Form C of Compound 1 were grown from thermal gradient sublimation at 160° C. A colorless triangular plate with approximate dimensions of 0.13×0.13×0.06 mm was chosen for data collection and mounted on a polymer loop. Single crystal data was collected using a Bruker Platform goniometer with an Apex- II detector. The diffractometer was equipped with an incident beam monochromator using Mo-Kα radiation (λ=0.71073 Å) and a monocap collimator. The crystals were cooled in a −100° C. nitrogen flow during data collection.

The data were indexed and integrated using the Apex-II suite of programs including Sainplus and SADABS. The triclinic cell parameters were determined to be: a=11.816(4) Å, b=15.036(5) Å, c=21.625(8) Å, alpha=92.255(6)°, beta=92.597(5)°, gamma=107.947(5)°, volume=3646(2) Å$^3$. The space group was determined to be P-1. The molecular weight was 468.23 g/mol giving a calculated density of 1.706 g/cm$^{-1}$, and μ(Mo)=0.53 mm$^{-1}$ for Z=8. Data reduction led to 11680 unique data from a two-theta range=3.62 to 48.48°. Structure solution and refinements were performed using the Shelxtl program suite with refinement based on F$^2$ with scattering factors from Int. Tab. Vol C Tables 4.2.6.8 and 6.1.1.4. The final refinement statistics include a data/parameter ratio=11.13, goodness-of-fit on F$^2$=0.97, R indices[I>4sigma(I)]R1=0.0595, wR2=0.1201, R indices (all data) R1=0.1454, wR2=0.1546, max difference peak and hole=0.890 and −0.357 e/Å$^3$. The atomic fractional coordinates (×10$^4$) and equivalent isotropic displacement parameters are listed in Tables 13 and 14. U (eq) is defined as one third of the trace of the orthogonalized Uij tensor. The estimated standard deviations are shown in parentheses.

TABLE 13

Atomic Coordinates (×10$^4$) and Equivalent Isotropic Displacement Parameters (A$^2$ × 10$^3$) for Compound 1 Polymorph Form C

| Atom | x | y | z | U(eq) |
|---|---|---|---|---|
| Cl(1) | 6400(1) | 6726(1) | 286(1) | 44(1) |
| Cl(2) | 8884(2) | 9826(1) | 2927(1) | 60(1) |
| Cl(21) | 4766(2) | 4474(1) | 1777(1) | 64(1) |
| Cl(22) | 3672(1) | 5663(1) | −310(1) | 47(1) |
| Cl(41) | −1571(2) | 8384(1) | 4287(1) | 51(1) |
| Cl(42) | −2104(1) | 5101(1) | 2310(1) | 50(1) |
| Cl(61) | −2362(1) | 7296(1) | 2514(1) | 44(1) |
| Cl(62) | 1367(1) | 9154(1) | 5072(1) | 44(1) |
| S(1) | 6067(1) | 9674(1) | 2720(1) | 36(1) |
| S(21) | 2573(2) | 7356(1) | 33(1) | 40(1) |
| S(41) | 750(1) | 5488(1) | 2654(1) | 35(1) |
| S(61) | 2152(1) | 7311(1) | 4686(1) | 36(1) |
| F(1) | 6635(4) | 9361(3) | −1935(2) | 67(1) |
| F(2) | 7359(4) | 8227(4) | −1897(2) | 94(2) |
| F(3) | 5493(4) | 7950(3) | −2006(2) | 76(1) |
| F(21) | 5541(3) | 6625(3) | 4390(2) | 62(1) |
| F(22) | 4429(4) | 5213(3) | 4307(2) | 70(1) |
| F(23) | 6251(3) | 5541(3) | 4114(2) | 62(1) |
| F(41) | −2215(4) | 7759(3) | 6688(2) | 74(1) |
| F(42) | −3901(4) | 6885(3) | 6346(2) | 69(1) |
| F(43) | −2665(3) | 6280(3) | 6762(2) | 59(1) |
| F(61) | −721(3) | 8196(3) | 192(2) | 66(1) |
| F(62) | 749(3) | 9422(3) | 416(2) | 56(1) |
| F(63) | −1022(3) | 9418(3) | 586(2) | 64(1) |
| O(1) | 6083(4) | 10736(3) | 1590(2) | 42(1) |
| O(2) | 6210(3) | 8915(3) | 3055(2) | 38(1) |
| O(3) | 4969(4) | 9858(3) | 2708(2) | 45(1) |
| O(4) | 7499(5) | 13124(3) | 3513(2) | 67(2) |
| O(21) | 3416(4) | 8404(3) | 1265(2) | 42(1) |
| O(22) | 1805(3) | 7893(3) | 142(2) | 48(1) |
| O(23) | 3604(4) | 7755(3) | −300(2) | 50(1) |
| O(24) | −1363(4) | 5143(3) | −928(2) | 44(1) |
| O(41) | 56(3) | 4553(3) | 3832(2) | 35(1) |
| O(42) | 780(4) | 6183(3) | 2224(2) | 40(1) |
| O(43) | 1826(3) | 5342(3) | 2871(2) | 41(1) |
| O(44) | 186(4) | 2227(3) | 1824(2) | 57(1) |
| O(61) | 3329(4) | 8208(3) | 3584(2) | 36(1) |
| O(62) | 2817(4) | 6711(3) | 4507(2) | 42(1) |
| O(63) | 1163(4) | 6960(3) | 5056(2) | 43(1) |
| O(64) | 6113(3) | 8915(3) | 5767(2) | 39(1) |
| N(1) | 6349(4) | 9441(3) | 2002(2) | 34(1) |
| N(2) | 6290(4) | 8632(3) | 838(2) | 30(1) |
| N(4) | 6322(4) | 9259(3) | −80(2) | 32(1) |
| N(21) | 2965(5) | 7016(4) | 698(2) | 44(1) |
| N(22) | 4007(4) | 6278(3) | 1604(2) | 32(1) |
| N(24) | 4376(4) | 6743(3) | 2608(2) | 31(1) |
| N(41) | 77(4) | 5774(3) | 3242(2) | 31(1) |
| N(42) | −936(4) | 6537(3) | 4124(2) | 30(1) |
| N(44) | −1560(4) | 6033(3) | 5037(2) | 30(1) |
| N(61) | 1602(4) | 7655(3) | 4062(2) | 31(1) |
| N(62) | 310(4) | 7796(3) | 2988(2) | 31(1) |
| N(64) | 1005(4) | 8472(3) | 2118(2) | 31(1) |
| C(1) | 6214(5) | 9972(4) | 1521(3) | 32(2) |
| C(2) | 6259(5) | 9528(4) | 907(3) | 32(2) |
| C(3) | 6282(5) | 9940(4) | 356(3) | 32(2) |
| C(5) | 6318(5) | 8484(4) | 238(3) | 27(1) |
| C(6) | 6379(5) | 7676(4) | −107(3) | 33(2) |
| C(7) | 6438(5) | 7708(5) | −735(3) | 39(2) |
| C(8) | 6424(5) | 8527(4) | −1034(3) | 33(2) |
| C(9) | 6356(5) | 9295(5) | −712(3) | 37(2) |
| C(10) | 6495(6) | 8534(6) | −1718(3) | 49(2) |
| C(11) | 7193(6) | 10723(4) | 2970(3) | 37(2) |
| C(12) | 8367(6) | 10756(5) | 3083(3) | 43(2) |
| C(13) | 9183(7) | 11568(5) | 3341(3) | 57(2) |
| C(14) | 8865(7) | 12324(6) | 3481(3) | 57(2) |
| C(15) | 7713(8) | 12321(4) | 3363(3) | 50(2) |
| C(16) | 6822(6) | 11500(5) | 3092(3) | 43(2) |
| C(17) | 6329(6) | 13094(5) | 3426(3) | 53(2) |
| C(21) | 3414(5) | 7600(5) | 1228(3) | 36(2) |
| C(22) | 3792(5) | 7111(4) | 1715(3) | 29(1) |
| C(23) | 4033(5) | 7411(4) | 2331(3) | 32(2) |
| C(25) | 4359(5) | 6064(4) | 2150(3) | 31(2) |
| C(26) | 4720(5) | 5308(4) | 2339(3) | 37(2) |
| C(27) | 5029(5) | 5238(4) | 2929(3) | 41(2) |
| C(28) | 5002(5) | 5950(4) | 3385(3) | 36(2) |
| C(29) | 4684(5) | 6676(4) | 3223(3) | 33(2) |
| C(30) | 5306(6) | 5831(5) | 4046(3) | 47(2) |
| C(31) | 1724(5) | 6269(4) | −327(2) | 31(2) |
| C(32) | 2190(5) | 5557(4) | −485(3) | 32(2) |
| C(33) | 1468(5) | 4728(4) | −763(3) | 35(2) |
| C(34) | 287(6) | 4623(5) | −906(3) | 39(2) |
| C(35) | −183(5) | 5331(4) | −768(3) | 32(2) |
| C(36) | 520(5) | 6151(4) | −474(3) | 35(2) |
| C(37) | −1866(5) | 5879(5) | −836(3) | 46(2) |
| C(41) | −203(5) | 5260(5) | 3757(3) | 30(1) |
| C(42) | −807(5) | 5681(4) | 4205(3) | 28(1) |
| C(43) | −1190(5) | 5346(5) | 4760(3) | 29(1) |
| C(45) | −1403(5) | 6733(4) | 4634(3) | 28(1) |
| C(46) | −1717(5) | 7546(4) | 4813(3) | 34(2) |
| C(47) | −2170(5) | 7599(4) | 5372(3) | 35(2) |
| C(48) | −2279(5) | 6860(4) | 5776(3) | 33(2) |
| C(49) | −1989(5) | 6085(5) | 5617(3) | 37(2) |
| C(50) | −2770(6) | 6933(5) | 6392(3) | 46(2) |
| C(51) | −230(5) | 4393(4) | 2346(2) | 30(2) |
| C(52) | −1440(5) | 4251(4) | 2185(3) | 34(2) |
| C(53) | −2098(6) | 3397(5) | 1914(3) | 41(2) |
| C(54) | −1611(6) | 2699(5) | 1789(3) | 45(2) |
| C(55) | −419(6) | 2850(4) | 1936(3) | 40(2) |
| C(56) | 264(5) | 3695(4) | 2224(3) | 35(2) |
| C(57) | −450(7) | 1370(5) | 1493(4) | 73(2) |
| C(61) | 2255(6) | 8011(4) | 3571(3) | 28(1) |
| C(62) | 1538(5) | 8145(4) | 3029(3) | 31(2) |
| C(63) | 1978(5) | 8563(4) | 2509(3) | 31(2) |
| C(65) | 10(5) | 8010(4) | 2430(3) | 25(1) |
| C(66) | −1125(5) | 7837(4) | 2120(3) | 28(1) |
| C(67) | −1205(5) | 8116(4) | 1546(3) | 32(2) |
| C(68) | −167(5) | 8584(4) | 1243(3) | 36(2) |
| C(69) | 919(5) | 8758(5) | 1529(3) | 37(2) |
| C(70) | −276(6) | 8904(5) | 615(3) | 45(2) |
| C(71) | 3137(5) | 8336(4) | 5069(2) | 28(1) |
| C(72) | 2789(5) | 9102(4) | 5244(3) | 30(2) |
| C(73) | 3582(5) | 9836(4) | 5586(2) | 31(2) |
| C(74) | 4710(5) | 9801(4) | 5765(2) | 32(2) |
| C(75) | 5043(5) | 9037(4) | 5603(3) | 29(1) |
| C(76) | 4259(5) | 8300(4) | 5236(2) | 29(1) |
| C(77) | 6895(5) | 9597(4) | 6204(3) | 42(2) |

TABLE 14

Hydrogen Coordinates (×10⁴) and Isotropic Displacement Parameters ($A^2 \times 10^3$) for Compound 1 Polymorph Form C

| Atom | x | y | z | U(eq) |
|---|---|---|---|---|
| H(1A) | 6596 | 8954 | 1925 | 41 |
| H(21A) | 2885 | 6417 | 723 | 53 |
| H(41A) | −119 | 6292 | 3227 | 38 |
| H(61A) | 840 | 7608 | 4042 | 37 |
| H(3A) | 6273 | 10558 | 288 | 38 |
| H(7A) | 6489 | 7179 | −972 | 47 |
| H(9A) | 6332 | 9839 | −915 | 44 |
| H(13A) | 9988 | 11587 | 3421 | 69 |
| H(14A) | 9441 | 12871 | 3665 | 68 |
| H(16A) | 6023 | 11489 | 3001 | 52 |
| H(17A) | 6235 | 13679 | 3596 | 80 |
| H(17B) | 5822 | 12566 | 3637 | 80 |
| H(17C) | 6096 | 13018 | 2981 | 80 |
| H(23A) | 3970 | 7974 | 2520 | 39 |
| H(27A) | 5268 | 4718 | 3049 | 49 |
| H(29A) | 4668 | 7148 | 3524 | 40 |
| H(33A) | 1782 | 4231 | −856 | 42 |
| H(34A) | −212 | 4052 | −1102 | 47 |
| H(36A) | 192 | 6637 | −370 | 42 |
| H(37A) | −2714 | 5656 | −970 | 69 |
| H(37B) | −1455 | 6407 | −1078 | 69 |
| H(37C) | −1777 | 6081 | −395 | 69 |
| H(43A) | −1198 | 4764 | 4919 | 35 |
| H(47A) | −2412 | 8124 | 5492 | 42 |
| H(49A) | −2076 | 5595 | 5893 | 44 |
| H(53A) | −2921 | 3286 | 1809 | 49 |
| H(54A) | −2092 | 2115 | 1602 | 54 |
| H(56A) | 1081 | 3793 | 2337 | 42 |
| H(57A) | 87 | 996 | 1427 | 110 |
| H(57B) | −764 | 1502 | 1091 | 110 |
| H(57C) | −1112 | 1021 | 1732 | 110 |
| H(63A) | 2791 | 8857 | 2433 | 37 |
| H(67A) | −1967 | 7999 | 1338 | 39 |
| H(69A) | 1615 | 9074 | 1327 | 45 |
| H(73A) | 3359 | 10372 | 5700 | 37 |
| H(74A) | 5253 | 10312 | 6002 | 38 |
| H(76A) | 4497 | 7778 | 5103 | 35 |
| H(77A) | 7548 | 9370 | 6350 | 64 |
| H(77B) | 6449 | 9698 | 6557 | 64 |
| H(77C) | 7222 | 10188 | 6004 | 64 |

Characterization Example 9

Single Crystal X-Ray Diffraction for Polymorph Form D of Compound 1

Suitable single crystals of polymorph Form D of Compound 1 were grown by slow evaporation of a saturated solution of Compound 1 in acetonitrile. A colorless irregular block with approximate dimensions of 0.50×0.50×0.33 mm was chosen for data collection and mounted on a polymer loop. Single crystal data was collected using a Bruker Platform goniometer with an Apex-II detector. The diffractometer was equipped with an incident beam monochromator using Mo-Kα radiation (λ=0.71073 Å) and a monocap collimator. The crystals were cooled in a −100° C. nitrogen flow during data collection.

The data were indexed and integrated using the Apex-II suite of programs including Sainplus and SADABS. The triclinic cell parameters were determined to be: a=7.223(3) Å, b=8.676(4) Å, c=14.905(6) Å, alpha=92.207(6)°, beta=97.182(7)°, gamma=99.385(6)°, volume=912.6(7) Å³. The space group was determined to be P-1. The molecular weight was 468.23 g/mol giving a calculated density of 1.704 g/cm³, and μ(Mo)=0.53 mm⁻¹ for Z=2. Data reduction led to 4449 unique data from a two-theta range=4.76 to 56.88°. Structure solution and refinements were performed using the Shelxtl program suite with refinement based on $F^2$ with scattering factors from Int. Tab. Vol C Tables 4.2.6.8 and 6.1.1.4. The final refinement statistics include a data/parameter ratio=16.66, goodness-of-fit on $F^2$=1.00, R indices[I>4sigma (I)]R1=0.0466, wR2=0.1221, R indices (all data) R1=0.0718, wR2=0.1362, max difference peak and hole=0.379 and −0.394 e/Å³. The atomic fractional coordinates (×10⁴) and equivalent isotropic displacement parameters are listed in Tables 15 and 16. U (eq) is defined as one third of the trace of the orthogonalized Uij tensor. The estimated standard deviations are shown in parentheses.

TABLE 15

Atomic Coordinates (×10⁴) and Equivalent Isotropic Displacement Parameters ($A^2 \times 10^3$) for Compound 1 Polymorph Form D

| Atom | x | y | z | U(eq) |
|---|---|---|---|---|
| O(4) | 1339(3) | −2648(2) | 3615(1) | 49(1) |
| S(1) | 4949(1) | 2693(1) | 3312(1) | 36(1) |
| Cl(1) | 12928(1) | 5241(1) | 1308(1) | 43(1) |
| F(1) | 13968(2) | 1644(2) | −1576(1) | 48(1) |
| O(1) | 4162(2) | 1171(2) | 1398(1) | 41(1) |
| N(1) | 6173(3) | 2856(3) | 2440(2) | 36(1) |
| C(1) | 5682(3) | 2018(3) | 1619(2) | 32(1) |
| Cl(2) | 8842(1) | 1369(1) | 4055(1) | 48(1) |
| F(2) | 12443(2) | 3251(2) | −2282(1) | 51(1) |
| O(2) | 6042(3) | 3790(2) | 3997(1) | 46(1) |
| C(2) | 7200(3) | 2233(3) | 1034(2) | 32(1) |
| N(2) | 8877(3) | 3242(2) | 1299(1) | 32(1) |
| F(3) | 11181(2) | 816(2) | −2290(1) | 52(1) |
| O(3) | 3039(3) | 2824(2) | 2997(1) | 44(1) |
| C(3) | 7183(4) | 1454(3) | 216(2) | 39(1) |
| N(4) | 8915(3) | 1993(2) | −47(1) | 33(1) |
| C(5) | 9893(3) | 3085(3) | 634(2) | 31(1) |
| C(6) | 11726(3) | 3857(3) | 493(2) | 32(1) |
| C(7) | 12457(3) | 3499(3) | −271(2) | 34(1) |
| C(8) | 11386(3) | 2355(3) | −936(2) | 33(1) |
| C(9) | 9639(4) | 1613(3) | −825(2) | 37(1) |
| C(10) | 12227(4) | 2016(3) | −1778(2) | 39(1) |
| C(11) | 4973(3) | 739(3) | 3610(2) | 32(1) |
| C(12) | 6625(3) | 176(3) | 3922(2) | 35(1) |
| C(13) | 6522(4) | −1388(3) | 4108(2) | 39(1) |
| C(14) | 4776(4) | −2387(3) | 4004(2) | 40(1) |
| C(15) | 3129(4) | −1807(3) | 3719(2) | 36(1) |
| C(16) | 3234(3) | −244(3) | 3513(2) | 34(1) |
| C(17) | 1087(5) | −4247(3) | 3840(2) | 52(1) |

TABLE 16

Hydrogen Coordinates (×10⁴) and Isotropic Displacement Parameters ($A^2 \times 10^3$) for Compound 1 Polymorph Form D

| Atom | x | y | z | U(eq) |
|---|---|---|---|---|
| H(1) | 7050(40) | 3210(30) | 2544(18) | 24(8) |
| H(3A) | 6187 | 704 | −101 | 47 |
| H(7A) | 13680 | 4010 | −364 | 41 |
| H(9A) | 8933 | 854 | −1269 | 44 |
| H(13A) | 7646 | −1781 | 4308 | 47 |
| H(14A) | 4714 | −3459 | 4128 | 48 |
| H(16A) | 2113 | 148 | 3306 | 41 |
| H(17A) | −266 | −4648 | 3827 | 79 |
| H(17B) | 1746 | −4324 | 4449 | 79 |
| H(17C) | 1608 | −4866 | 3401 | 79 |

Characterization Example 10

Single Crystal X-Ray Diffraction for Polymorph Form TS of Compound 1

Suitable single crystals for the toluene solvate of Compound 1 (designated polymorph Form TS) were grown by slow evaporation of a saturated solution of Compound 1 in toluene. A colorless needle with approximate dimensions of 0.48×0.13×0.04 mm was chosen for data collection and mounted on a polymer loop. Single crystal data were collected using a Bruker Platform goniometer with an Apex-II detector. The diffractometer is equipped with an incident beam monochromator using Mo-Kα radiation (λ=0.71073 Å) and a monocap collimator. The crystals were cooled in a −100° C. nitrogen flow during data collection.

The data were indexed and integrated using the Apex-II suite of programs including Sainplus and SADABS. The triclinic cell parameters were determined to be: a=12.547(6) Å, b=15.165(7) Å, c=15.311(7) Å, alpha=100.594(9)°, beta=109.609(8)°, gamma=110.924(8)°, volume=2405.8 (19) Å$^3$. The space group was determined to be P-1. The molecular weight was 560.36 g/mol giving a calculated density of 1.547 g/cm$^3$, and μ(Mo)=0.42 mm$^{-1}$ for Z=4. Data reduction led to 10653 unique data from a two-theta range=3.48 to 54.44°. Structure solution and refinements were performed using the Shelxtl program suite with refinement based on F$^2$ with scattering factors from Int. Tab. Vol C Tables 4.2.6.8 and 6.1.1.4. The final refinement statistics include a data/parameter ratio=16.31, goodness-of-fit on F$^2$=1.02, R indices[I>4sigma(I)]R1=0.0727, wR2=0.1676, R indices (all data) R1=0.1546, wR2=0.2053, max difference peak and hole=0.641 and −0.637 e/Å$^3$. The atomic fractional coordinates (×10$^4$) and equivalent isotropic displacement parameters are listed in Tables 17 and 18. U (eq) is defined as one third of the trace of the orthogonalized Uij tensor. The estimated standard deviations are shown in parentheses.

TABLE 17

Atomic Coordinates (×10$^4$) and Equivalent Isotropic Displacement Parameters (A$^2$ × 10$^3$) for Compound 1 Polymorph Form TS

| Atom | x | y | z | U(eq) |
|---|---|---|---|---|
| Cl(1) | 4975(1) | 1411(1) | 2566(1) | 53(1) |
| Cl(2) | 114(1) | 2917(1) | 505(1) | 58(1) |
| Cl(21) | 1524(1) | 1282(1) | −13(1) | 50(1) |
| Cl(22) | 7874(1) | 3395(1) | 3083(1) | 58(1) |
| S(1) | 2877(1) | 4894(1) | 1388(1) | 36(1) |
| S(21) | 7216(1) | 5258(1) | 3748(1) | 34(1) |
| F(1) | 5308(3) | 2050(2) | 6851(2) | 60(1) |
| F(2) | 4357(3) | 588(2) | 5748(2) | 63(1) |
| F(3) | 6348(3) | 1455(3) | 6287(3) | 76(1) |
| F(21) | 845(3) | 1366(3) | −3764(2) | 65(1) |
| F(22) | 1629(3) | 350(2) | −3557(2) | 66(1) |
| F(23) | 2696(3) | 1749(3) | −3651(2) | 62(1) |
| O(1) | 3274(3) | 5092(2) | 3429(2) | 40(1) |
| O(2) | 2613(3) | 4373(3) | 407(2) | 47(1) |
| O(3) | 3920(3) | 5885(2) | 1903(3) | 43(1) |
| O(4) | 816(3) | 7018(2) | 2121(3) | 48(1) |
| O(21) | 7020(3) | 5485(2) | 1840(2) | 39(1) |
| O(22) | 6914(3) | 4706(2) | 4361(2) | 44(1) |
| O(23) | 7210(3) | 6215(2) | 3903(2) | 44(1) |
| O(24) | 11876(3) | 7562(3) | 4794(3) | 55(1) |
| N(1) | 3126(3) | 4153(3) | 2015(3) | 32(1) |
| N(2) | 4142(3) | 3090(3) | 3025(3) | 29(1) |
| N(4) | 4399(3) | 3041(3) | 4535(3) | 29(1) |
| N(21) | 6163(3) | 4503(3) | 2618(3) | 31(1) |
| N(22) | 4119(3) | 3178(3) | 791(3) | 30(1) |
| N(24) | 4031(3) | 3083(3) | −711(3) | 29(1) |
| C(1) | 3403(4) | 4405(3) | 3013(3) | 32(1) |
| C(2) | 3831(4) | 3765(3) | 3480(3) | 26(1) |
| C(3) | 3987(4) | 3756(3) | 4406(3) | 32(1) |
| C(5) | 4478(4) | 2654(3) | 3673(3) | 31(1) |
| C(6) | 4878(4) | 1896(3) | 3625(4) | 35(1) |
| C(7) | 5145(4) | 1551(3) | 4389(4) | 37(1) |
| C(8) | 5029(4) | 1963(4) | 5241(4) | 36(1) |
| C(9) | 4669(4) | 2709(3) | 5319(3) | 33(1) |
| C(10) | 5267(5) | 1535(4) | 6039(4) | 44(1) |
| C(11) | 1509(4) | 4968(3) | 1392(3) | 33(1) |

TABLE 17-continued

Atomic Coordinates (×10$^4$) and Equivalent Isotropic Displacement Parameters (A$^2$ × 10$^3$) for Compound 1 Polymorph Form TS

| Atom | x | y | z | U(eq) |
|---|---|---|---|---|
| C(12) | 332(4) | 4134(3) | 990(4) | 38(1) |
| C(13) | −702(4) | 4273(4) | 971(4) | 43(1) |
| C(14) | −582(4) | 5230(4) | 1334(4) | 42(1) |
| C(15) | 579(4) | 6052(4) | 1731(4) | 36(1) |
| C(16) | 1633(4) | 5922(3) | 1773(4) | 36(1) |
| C(17) | −250(5) | 7204(4) | 2029(4) | 51(1) |
| C(21) | 6202(4) | 4726(3) | 1797(3) | 29(1) |
| C(22) | 5168(4) | 3956(3) | 854(3) | 29(1) |
| C(23) | 5127(4) | 3920(3) | −56(3) | 31(1) |
| C(25) | 3447(4) | 2664(3) | −157(3) | 28(1) |
| C(26) | 2271(4) | 1776(3) | −689(3) | 33(1) |
| C(27) | 1791(4) | 1348(3) | −1674(3) | 34(1) |
| C(28) | 2456(4) | 1803(3) | −2195(3) | 31(1) |
| C(29) | 3547(4) | 2656(3) | −1715(3) | 32(1) |
| C(30) | 1912(5) | 1324(4) | −3276(4) | 42(1) |
| C(31) | 8710(4) | 5430(3) | 3815(3) | 31(1) |
| C(32) | 8999(4) | 4644(4) | 3571(4) | 39(1) |
| C(33) | 10224(5) | 4854(4) | 3700(4) | 45(1) |
| C(34) | 11158(5) | 5834(4) | 4098(4) | 45(1) |
| C(35) | 10883(4) | 6621(4) | 4372(4) | 42(1) |
| C(36) | 9649(4) | 6417(4) | 4213(3) | 35(1) |
| C(37) | 11653(5) | 8372(4) | 5147(6) | 77(2) |
| C(40) | 582(7) | 2435(6) | 3159(6) | 104(3) |
| C(41) | 1006(5) | 1600(5) | 3079(5) | 72(2) |
| C(42) | 1132(6) | 1203(5) | 2253(5) | 66(2) |
| C(43) | 1515(6) | 476(6) | 2168(6) | 76(2) |
| C(44) | 1832(6) | 105(5) | 2992(8) | 104(3) |
| C(45) | 1677(6) | 548(6) | 3814(6) | 78(2) |
| C(46) | 1282(6) | 1266(6) | 3819(5) | 80(2) |
| C(50) | 6001(8) | 1857(6) | −648(9) | 144(5) |
| C(51) | 4910(12) | 1078(9) | −849(11) | 159(5) |
| C(52) | 4059(10) | 307(7) | −1675(6) | 98(3) |
| C(53) | 2955(10) | −523(8) | −1811(8) | 124(3) |
| C(54) | 2697(11) | −556(9) | −1003(8) | 125(4) |
| C(55) | 3450(17) | 147(14) | −140(10) | 181(7) |
| C(56) | 4560(12) | 994(9) | −24(8) | 116(4) |

TABLE 18

Hydrogen Coordinates (×10$^4$) and Isotropic Displacement Parameters (A$^2$ × 10$^3$) for Compound 1 Polymorph Form TS

| Atom | x | y | z | U(eq) |
|---|---|---|---|---|
| H(1A) | 3082 | 3582 | 1708 | 39 |
| H(21A) | 5550 | 3933 | 2537 | 37 |
| H(3A) | 3841 | 4158 | 4862 | 39 |
| H(7A) | 5409 | 1037 | 4353 | 45 |
| H(9A) | 4608 | 2992 | 5897 | 40 |
| H(13A) | −1508 | 3706 | 706 | 52 |
| H(14A) | −1306 | 5314 | 1308 | 50 |
| H(16A) | 2444 | 6489 | 2065 | 44 |
| H(17A) | 37 | 7930 | 2289 | 76 |
| H(17B) | −658 | 6875 | 2403 | 76 |
| H(17C) | −858 | 6935 | 1331 | 76 |
| H(23A) | 5731 | 4379 | −201 | 37 |
| H(27A) | 1015 | 747 | −2022 | 41 |
| H(29A) | 3977 | 2960 | −2066 | 38 |
| H(33A) | 10419 | 4320 | 3513 | 54 |
| H(34A) | 11995 | 5973 | 4185 | 54 |
| H(36A) | 9448 | 6954 | 4376 | 42 |
| H(37A) | 12456 | 8992 | 5482 | 115 |
| H(37B) | 11291 | 8243 | 5613 | 115 |
| H(37C) | 11059 | 8445 | 4591 | 115 |
| H(40A) | 39 | 2329 | 3502 | 156 |
| H(40B) | 106 | 2417 | 2495 | 156 |
| H(40C) | 1329 | 3091 | 3529 | 156 |
| H(42A) | 942 | 1450 | 1723 | 79 |
| H(43A) | 1577 | 210 | 1585 | 92 |
| H(44A) | 2119 | −395 | 2977 | 125 |
| H(45A) | 1856 | 335 | 4370 | 94 |
| H(46A) | 1197 | 1545 | 4386 | 96 |

TABLE 18-continued

Hydrogen Coordinates (×10⁴) and Isotropic Displacement Parameters
($A^2 \times 10^3$) for Compound 1 Polymorph Form TS

| Atom | x | y | z | U(eq) |
|---|---|---|---|---|
| H(50A) | 5833 | 2242 | −1081 | 215 |
| H(50B) | 6582 | 1608 | −760 | 215 |
| H(50C) | 6388 | 2292 | 43 | 215 |
| H(52A) | 4208 | 312 | −2243 | 117 |
| H(53A) | 2410 | −1040 | −2438 | 149 |
| H(54A) | 1958 | −1102 | −1079 | 150 |
| H(55A) | 3271 | 104 | 410 | 217 |
| H(56A) | 5082 | 1514 | 603 | 140 |

Characterization Example 11

Differential Scanning Calorimetry Experiments

The DSC curve for pure polymorph Form A of Compound 1 was observed to exhibit a sharp endotherm with an onset temperature at 212° C. (signal maximum at 212.6° C.) immediately followed or overlapped by an exotherm with a signal maximum at 213° C. These endothermic-exothermic events were followed by a main melting endotherm at an onset temperature of 218° C. (signal maximum at 219° C., end point 225° C., heat of transition 63 J/g).

The DSC curve for polymorph Form B of Compound 1 was observed to exhibit a minor endotherm with an onset temperature of 205° C. (signal maximum at 208° C., heat of transition 4 J/g) and a sharp major endotherm with an onset temperature at 217.9° C. (signal maximum at 218° C., heat of transition 56 µg).

The DSC curve for polymorph Form D of Compound 1 was observed to exhibit a minor endotherm at an onset temperature of 211° C. (maximum at 212° C., heat of transition 10 J/g) and a sharp major endotherm at an onset temperature of 218° C. (maximum at 219° C., heat of transition 62 J/g).

The DSC curve for polymorph Form TS of Compound 1 (toluene solvate) was observed to exhibit four endotherms. Endotherm 1 was a broad endotherm with an onset temperature of 118° C. (signal maximum at 137° C., heat of transition 74 µg). Endotherm 2 had an onset temperature at 200° C. (signal maximum at 202° C., heat of transition 6 J/g). Endotherm 3 had an onset temperature at 207° C. (signal maximum at 208° C., heat of transition 3 µg). Endotherm 4 had an onset temperature at 216° C. (signal maximum at 217° C., heat of transition 42 J/g).

The DSC curve of mixtures of polymorph Forms A and B of Compound 1 prepared from polymorph Form TS according to Preparation Example 2 were observed to exhibit a minor endotherm with an onset temperature at 208° C. (signal maximum at 211° C., heat of transition 4.6 J/g) and a sharp major endotherm with an onset temperature at 218° C. (signal maximum at 219° C., heat of transition 58 J/g).

Characterization Example 12

Relative Stability Experiments

The relative stability of various crystal forms of Compound 1 were subjected to non-competitive and competitive inter-conversion experiments. For the non-competitive experiments, only a single starting crystal form was used to study the potential conversion to another more stable form. For the competitive experiments, two or more crystal forms were mixed together and studied for the potential conversion to a more stable form. The experimental conditions are described below and summarized in Table 19.

In Example 12a, Form A of Compound 1 (0.4 g) prepared according to Preparation Example 5c was refluxed in deionized water (4 mL) at about 95° C. for 3 hours. The slurry was cooled to 25-30° C., filtered, suction dried for 1 hour and dried in a vacuum oven at 70° C. and 8 kPa absolute pressure for 12 hours. Analysis by pXRD, DSC, TGA and ¹H-NMR of the resulting material indicated that the crystal form remained unchanged, i.e. Form A.

In Example 12b, Form B of Compound 1 (0.4 g) prepared according to Preparation Example 5f was refluxed in deionized water (4 mL) at about 95° C. for 3 hours. The slurry was cooled to 25-30° C., filtered, suction dried for 1 hour and dried in a vacuum oven at 70° C. and 8 kPa absolute pressure for 12 hours. Analysis by pXRD, DSC, TGA and ¹H-NMR of the resulting material indicated Form A.

In Example 12c, Form D of Compound 1 (0.4 g) prepared according to Preparation Example 5g was refluxed in deionized water (4 mL) at about 95° C. for 3 hours. The slurry was cooled to 25-30° C., filtered, suction dried for 1 hour and dried in a vacuum oven at 70° C. and 8 kPa absolute pressure for 12 hours. Analysis by pXRD, DSC, TGA and ¹H-NMR of the resulting material indicated Form A.

In Example 12d, Form TS of Compound 1 (1 g) prepared according to Preparation Example 1 was refluxed in deionized water (10 mL) at about 95° C. for 3 hours. The slurry was cooled to 25-30° C., filtered, suction dried for 1 hour and dried in a vacuum oven at 65° C. and 8 kPa absolute pressure for 12 hours. Analysis by pXRD, DSC, TGA and ¹H-NMR of the resulting material indicated Form A.

In Example 12e, Form A (0.6 g) and Form B (0.6 g) of Compound 1 prepared according to Preparation Examples 5c and 5f, respectively, were blended as solids and refluxed in deionized water (12 mL) at about 95° C. for 3 hours. The slurry was cooled to 25-30° C., filtered, suction dried for 1 hour and dried in a vacuum oven at 65° C. and 8 kPa absolute pressure for 12 hours. Analysis by pXRD, DSC, TGA and ¹H-NMR of the resulting material indicated Form A.

In Example 12f, Form B (0.6 g) and Form D (0.6 g) of Compound 1 prepared according to Preparation Examples 5f and 5g, respectively, were blended as solids and refluxed in deionized water (12 mL) at about 95° C. for 3 hours. The slurry was cooled to 25-30° C., filtered, suction dried for 1 hour and dried in a vacuum oven at 65° C. and 8 kPa absolute pressure for 12 hours. Analysis by pXRD, DSC and ¹H-NMR of the resulting material indicated Form A.

In Example 12g, Form A (0.6 g) and Form D (0.6 g) of Compound 1 prepared according to Preparation Examples 5c and 5g, respectively, were blended as solids and refluxed in deionized water (12 mL) at about 95° C. for 3 hours. The slurry was cooled to 25-30° C., filtered, suction dried for 1 hour and dried in a vacuum oven at 65° C. and 8 kPa absolute pressure for 12 hours. Analysis by pXRD, DSC and ¹H-NMR of the resulting material indicated Form A.

In Example 12h, Form A (0.25 g), Form B (0.25 g), Form D (0.25 g) and Form TS (0.25 g) of Compound 1 prepared according to Preparation Examples 5c, 5f, 5g, and 1, respectively, were blended as solids and refluxed in deionized water (10 mL) at about 95° C. for 3 hours. The slurry was cooled to 25-30° C., filtered, suction dried for 1 hour and dried in a vacuum oven at 65° C. and 8 kPa absolute pressure for 12 hours. Analysis by pXRD, DSC and ¹H-NMR of the resulting material indicated Form A.

In Example 12i, Form A (0.25 g), Form B (0.25 g), Form D (0.25 g) and mixed Forms A and B (0.25 g) of Compound 1 prepared according to Preparation Examples 5c, 5f, 5g and 2, respectively, were blended as solids and refluxed in deionized water (10 mL) at about 95° C. for 3 hours. The slurry was cooled to 25-30° C., filtered, suction dried for 1 hour and dried in a vacuum oven at 65° C. and 8 kPa absolute pressure for 12 hours. Analysis by pXRD, DSC and $^1$H-NMR of the resulting material indicated Form A.

In Example 12j, Form A (0.25 g), Form B (0.25 g), Form D (0.25 g) and mixed Forms A and B (0.25 g) of Compound 1 prepared according to Preparation Examples 5c, 5f, 5g and 2, respectively, were blended as solids and heated in methanol (10 mL) at about 55° C. for 3 hours. The slurry was cooled to 25-30° C., filtered, suction dried for 1 hour and dried in a vacuum oven at 55° C. and 1.3 kPa absolute pressure for 12 hours. Analysis by pXRD, DSC and $^1$H-NMR of the resulting material indicated Form A.

In Example 12k, Form A (0.9 g), Form B (0.9 g), Form D (0.9 g) of Compound 1 prepared according to Preparation Examples 5c, 5f, and 5g, respectively, were blended as solids and heated in deionized water (27 mL) at about 55° C. for 168 hours. The slurry was cooled to 25-30° C., filtered, suction dried for 1 hour and dried in a vacuum oven at 65° C. and 8 kPa absolute pressure for 12 hours. Analysis by pXRD, DSC and $^1$H-NMR of the resulting material indicated Form A.

In Example 12l, the mixed Forms A and B (2.0 g) of Compound 1 prepared according to Preparation Example 2 was added to a 100 mL three-neck round-bottom flask equipped with magnetic stirrer and temperature probe. Deionized water (40 mL) was added and the resulting slurry was stirred at 25° C. for about 168 hours. The slurry filtered, suction dried for 1 hour and dried in a vacuum oven at 65° C. and 8 kPa absolute pressure for 12 hours. Analysis by pXRD, DSC and $^1$H-NMR of the resulting material indicated Form A.

TABLE 19

Relative Stability Experiments for Various Crystal Forms of Compound 1

| Example | Starting Crystal Form | Solvent | Temperature (° C.); time (h) | Obtained Crystal Form |
|---|---|---|---|---|
| 12a | A | water | 95; 3 | A |
| 12b | B | water | 95; 3 | A |
| 12c | D | water | 95; 3 | A |
| 12d | TS | water | 95; 3 | A |
| 12e | A, B | water | 95; 3 | A |
| 12f | B, D | water | 95; 3 | A |
| 12g | A, D | water | 95; 3 | A |
| 12h | A, B, D, TS | water | 95; 3 | A |
| 12i | A, B, D, A + B | water | 95; 3 | A |
| 12j | A, B, D, A + B | methanol | 55; 3 | A |
| 12k | A, B, D | water | 55; 168 | A |
| 12l | A + B | water | 25; 168 | A |

Characterization Example 13

Stability Experiment for Polymorph Form A of Compound 1

The physical stability of Form A of Compound 1 was determined as follows. Compound 1 prepared according to Preparation Example 3 was analyzed by pXRD, DSC, HPLC and $^1$H-NMR and found to be of pure crystal Form A of 99.9% purity (by HPLC peak area at 230 nm detection wavelength). An aliquot of the sample (3.0 g) was placed in a primary polyethylene bag, the primary bag was flushed with nitrogen gas and sealed. The primary polyethylene bag was then placed in a secondary polyethylene bag which was again flushed with nitrogen gas and a silica gel sachet was placed between the inner and the outer bag. The double bagged material was then placed in a triple laminated aluminum pouch and placed in a stability chamber at 40° C. for 30 days. Analysis by HPLC and $^1$H-NMR of the resulting material indicated pure Form A of Compound 1 of 99.9% purity (by HPLC peak area at 230 nm). Analysis by pXRD and DSC indicated pure polymorph Form A. The results confirm both chemical stability of Compound 1 as well as the stability of polymorph Form A under the conditions studied.

Characterization Example 14

Single Crystal X-Ray Diffraction for Polymorph Form C of Compound 1

Suitable single crystals for polymorph Form C of Compound 1 were grown from thermal gradient sublimation at 250° C. A colorless irregular plate with approximate dimensions ~0.320×0.230×0.060 mm was chosen for data collection and mounted on a polymer loop. Single crystal data were collected using a Bruker Platform goniometer with an Apex-II detector. The diffractometer is equipped with an incident beam monochromator using MoKα radiation (λ=0.71073 Å) and a monocap collimator. The crystals were run at room temperature (23° C.).

The data were indexed and integrated using the Apex-II suite of programs including Sainplus and SADABS. The triclinic cell parameters were determined to be: a=14.835(7) Å, b=15.216(8) Å, c=18.790(10) Å, alpha=90.306(7)°, beta=93.619(7)°, gamma=113.045(7)°, volume=3893(3) Å$^3$. The space group was determined to be P-1. The molecular weight was 468.23 giving a calculated density of 1.598 g/cm$^3$, and µ(Mo)=0.50 mm$^{-1}$ for Z=8. Data reduction led to 12368 unique data from a two-theta range=2.18 to 48.66°. Structure solution and refinements were performed using the Shelxtl program suite with refinement based on F$^2$ with scattering factors from Int. Tab. Vol C Tables 4.2.6.8 and 6.1.1.4. The final refinement statistics include a data/parameter ratio=11.78, goodness-of-fit on F$^2$=1.29, R indices[I>4sigma (I)]R1=0.1124, wR2=0.2544, R indices (all data) R1=0.2440, wR2=0.2969, max difference peak and hole=0.656 and −0.435 e/Å$^3$. The asymmetric unit contains four molecules. The form undergoes a crystallographic phase change when the crystals were cooled. The same crystallite was cooled to −100° C. and the resulting unit cell parameters were triclinic, P-1, a=11.816(4) Å, b=15.036(5) Å, c=21.625(8) Å, alpha=92.255(6)°, beta=92.597(5)°, gamma=107.947(5)°, Vol=3646(2) Å$^3$, Z=8. The atomic fractional coordinates (×10$^4$) and equivalent isotropic displacement parameters are listed and U (eq) is defined as one third of the trace of the orthogonalized Uij tensor. The estimated standard deviations are shown in parentheses.

TABLE 20

Atomic Coordinates (×10$^4$) and Equivalent Isotropic Displacement Parameters (A$^2$ × 10$^3$) for Compound 1 Polymorph Form C at Room Temperature

| Atom | x | y | z | U(eq) |
|---|---|---|---|---|
| Cl(1) | 4670(3) | 13564(3) | 3673(3) | 108(1) |
| S(1) | 1417(2) | 8900(2) | 3990(2) | 65(1) |
| F(1) | 8439(7) | 14244(9) | 4765(8) | 181(6) |
| O(1) | 3384(5) | 8914(6) | 4286(4) | 63(2) |
| N(1) | 2497(6) | 9779(6) | 3957(5) | 63(3) |

TABLE 20-continued

Atomic Coordinates (×10⁴) and Equivalent Isotropic Displacement Parameters ($Å^2 \times 10^3$) for Compound 1 Polymorph Form C at Room Temperature

| Atom | x | y | z | U(eq) |
|---|---|---|---|---|
| C(1) | 3379(8) | 9633(10) | 4162(6) | 59(3) |
| Cl(2) | 1838(3) | 9382(3) | 2330(2) | 107(1) |
| F(2) | 8467(7) | 14127(8) | 3653(8) | 171(5) |
| O(2) | 1334(6) | 8480(6) | 4678(5) | 79(3) |
| N(2) | 4144(6) | 11407(7) | 3965(5) | 53(2) |
| C(2) | 4247(7) | 10565(8) | 4112(5) | 50(3) |
| F(3) | 8678(5) | 13101(7) | 4328(6) | 141(4) |
| O(3) | 740(5) | 9310(5) | 3776(5) | 81(3) |
| C(3) | 5184(8) | 10643(8) | 4262(6) | 56(3) |
| O(4) | 690(7) | 5473(7) | 3345(6) | 100(3) |
| N(4) | 5739(6) | 11615(7) | 4166(6) | 55(2) |
| C(5) | 5081(8) | 12039(8) | 4010(6) | 52(3) |
| C(6) | 5483(9) | 13038(9) | 3902(7) | 68(3) |
| C(7) | 6491(9) | 13545(9) | 3980(6) | 68(3) |
| C(8) | 7099(8) | 13062(10) | 4151(6) | 66(3) |
| C(9) | 6737(8) | 12148(9) | 4241(6) | 66(3) |
| C(10) | 8165(11) | 13633(14) | 4262(13) | 116(6) |
| C(11) | 1374(8) | 8024(9) | 3354(7) | 60(3) |
| C(12) | 1529(8) | 8254(9) | 2653(8) | 71(4) |
| C(13) | 1416(10) | 7550(13) | 2146(8) | 87(4) |
| C(14) | 1127(9) | 6643(13) | 2348(9) | 94(5) |
| C(15) | 987(8) | 6381(10) | 3064(8) | 71(4) |
| C(16) | 1098(7) | 7116(11) | 3557(7) | 65(4) |
| C(17) | 429(12) | 4715(11) | 2852(10) | 142(7) |
| Cl(21) | −386(3) | 768(3) | 557(2) | 113(1) |
| S(21) | 3458(3) | 4973(3) | 1524(2) | 84(1) |
| F(21) | −3470(7) | 1165(10) | −889(6) | 194(6) |
| O(21) | 1767(6) | 5507(7) | 1015(5) | 91(3) |
| N(21) | 2265(7) | 4326(8) | 1364(6) | 84(3) |
| C(21) | 1586(9) | 4665(12) | 1078(7) | 69(4) |
| Cl(22) | 2787(3) | 4447(3) | 3157(2) | 114(1) |
| F(22) | −3951(8) | 871(11) | 145(8) | 209(7) |
| O(22) | 3845(6) | 4303(6) | 1803(5) | 98(3) |
| N(22) | 514(8) | 2977(8) | 837(5) | 68(3) |
| C(22) | 634(9) | 3935(9) | 860(6) | 63(3) |
| F(23) | −3741(8) | 2247(9) | −295(7) | 177(5) |
| O(23) | 3798(7) | 5471(6) | 903(5) | 109(4) |
| C(23) | −188(11) | 4043(10) | 647(7) | 73(4) |
| O(24) | 4400(8) | 8393(8) | 2211(6) | 110(3) |
| N(24) | −892(8) | 3151(9) | 464(5) | 72(3) |
| C(25) | −401(9) | 2512(10) | 583(6) | 65(3) |
| C(26) | −967(11) | 1527(10) | 415(7) | 73(4) |
| C(27) | −1900(31) | 1273(11) | 160(7) | 91(5) |
| C(28) | −2371(11) | 1913(12) | 29(7) | 79(4) |
| C(29) | −1858(10) | 2823(12) | 186(7) | 76(4) |
| C(30) | −3393(14) | 1514(19) | −229(11) | 134(8) |
| C(31) | 3518(9) | 5823(10) | 2194(8) | 74(4) |
| C(32) | 3231(9) | 5579(9) | 2877(8) | 75(4) |
| C(33) | 3283(9) | 6314(12) | 3353(8) | 89(5) |
| C(34) | 3658(9) | 7281(12) | 3122(9) | 85(5) |
| C(35) | 3979(10) | 7468(12) | 2464(10) | 86(4) |
| C(36) | 3868(9) | 6762(11) | 1969(8) | 84(4) |
| C(37) | 4462(11) | 9140(11) | 2628(9) | 117(6) |
| Cl(41) | 12222(2) | 12142(3) | 2485(2) | 92(1) |
| S(41) | 13696(2) | 11329(3) | 5916(2) | 72(1) |
| F(41) | 8722(7) | 12391(8) | 2197(6) | 141(4) |
| O(41) | 11559(6) | 10827(6) | 5869(4) | 69(2) |
| N(41) | 12934(6) | 11403(7) | 5260(4) | 61(3) |
| C(41) | 11946(8) | 11132(8) | 5315(7) | 54(3) |
| Cl(42) | 14434(3) | 13607(3) | 5610(2) | 105(1) |
| F(42) | 8192(7) | 10930(8) | 2016(6) | 160(4) |
| O(42) | 13290(6) | 10410(6) | 6221(5) | 83(3) |
| N(42) | 11841(6) | 11547(6) | 4061(5) | 56(3) |
| C(42) | 11402(8) | 11256(7) | 4692(6) | 44(3) |
| F(43) | 7846(8) | 11502(9) | 2938(6) | 149(4) |
| O(43) | 14622(6) | 11639(7) | 5610(4) | 94(3) |
| C(43) | 10451(8) | 11113(7) | 4625(6) | 55(3) |
| O(44) | 13303(7) | 12294(8) | 8454(5) | 92(3) |
| N(44) | 10263(6) | 11316(6) | 3941(6) | 58(3) |
| C(45) | 11128(8) | 11594(8) | 3586(7) | 53(3) |
| C(46) | 11154(8) | 11825(8) | 2881(7) | 57(3) |
| C(47) | 10330(10) | 11825(9) | 2555(7) | 84(4) |
| C(48) | 9429(9) | 11571(9) | 2898(7) | 70(4) |
| C(49) | 9411(8) | 11318(8) | 3592(7) | 64(3) |
| C(50) | 8555(12) | 11585(14) | 2526(10) | 99(5) |
| C(51) | 13735(7) | 12186(9) | 6559(7) | 56(3) |
| C(52) | 14059(8) | 13152(10) | 6413(7) | 70(4) |
| C(53) | 14149(9) | 13814(9) | 6983(8) | 84(4) |
| C(54) | 13868(9) | 13451(11) | 7640(8) | 86(5) |
| C(55) | 13543(9) | 12513(12) | 7787(8) | 77(4) |
| C(56) | 13458(8) | 11865(9) | 7232(7) | 69(4) |
| C(57) | 12973(14) | 11357(13) | 8624(9) | 135(7) |
| Cl(61) | 2116(3) | 798(3) | 973(2) | 107(1) |
| S(61) | 1366(3) | 4063(3) | −1109(2) | 73(1) |
| F(61) | 5652(9) | 1888(11) | 2485(6) | 182(6) |
| O(61) | 3563(6) | 4694(6) | −937(5) | 75(3) |
| N(61) | 2059(7) | 3768(7) | −523(5) | 64(3) |
| C(61) | 3074(10) | 4077(10) | −558(7) | 68(4) |
| Cl(62) | 619(3) | 1748(3) | −1210(2) | 102(1) |
| F(62) | 6661(11) | 2798(12) | 1845(12) | 288(11) |
| O(62) | 1807(7) | 5075(6) | −1209(4) | 85(3) |
| N(62) | 2901(7) | 2719(8) | 234(5) | 62(3) |
| C(62) | 3502(10) | 3547(8) | −65(6) | 55(3) |
| F(63) | 6029(13) | 1417(15) | 1633(7) | 249(10) |
| O(63) | 414(6) | 3643(7) | −838(5) | 98(3) |
| C(63) | 4436(9) | 3767(9) | 128(7) | 59(3) |
| O(64) | 1969(7) | 4070(6) | −3699(5) | 90(3) |
| N(64) | 4456(7) | 3084(8) | 586(5) | 66(3) |
| C(65) | 3485(11) | 2471(10) | 625(7) | 69(4) |
| C(66) | 3312(10) | 1619(9) | 1020(7) | 74(4) |
| C(67) | 4065(12) | 1504(11) | 1415(7) | 83(4) |
| C(68) | 5007(12) | 2198(13) | 1416(8) | 88(4) |
| C(69) | 5229(10) | 2981(11) | 995(8) | 81(4) |
| C(70) | 5785(14) | 2080(20) | 1862(13) | 127(7) |
| C(71) | 1361(8) | 3412(10) | −1888(7) | 62(3) |
| C(72) | 1026(8) | 2440(9) | −1937(7) | 66(3) |
| C(73) | 977(9) | 1965(10) | −2579(8) | 77(4) |
| C(74) | 1292(8) | 2507(10) | −3180(8) | 69(4) |
| C(75) | 1620(9) | 3487(10) | −3138(7) | 67(4) |
| C(76) | 1667(8) | 3952(9) | −2495(8) | 69(4) |
| C(77) | 1778(12) | 3604(11) | −4407(7) | 116(6) |

TABLE 21

Hydrogen Coordinates (×10⁴) and Isotropic Displacement Parameters ($Å^2 \times 10^3$) for Compound 1 Polymorph Form C at Room Temperature

| Atom | x | y | z | U(eq) |
|---|---|---|---|---|
| H(1A) | 2536 | 10329 | 3817 | 75 |
| H(3A) | 5404 | 10169 | 4395 | 67 |
| H(7A) | 6759 | 14202 | 3919 | 82 |
| H(9A) | 7160 | 11845 | 4358 | 79 |
| H(13A) | 1538 | 7703 | 1673 | 105 |
| H(14A) | 1014 | 6166 | 2001 | 113 |
| H(16A) | 980 | 6973 | 4031 | 78 |
| H(17A) | 193 | 4123 | 3096 | 213 |
| H(17B) | 991 | 4765 | 2603 | 213 |
| H(17C) | −79 | 4732 | 2517 | 213 |
| H(21A) | 2053 | 3732 | 1467 | 101 |
| H(23A) | −272 | 4617 | 627 | 88 |
| H(27A) | −2268 | 627 | 61 | 110 |
| H(29A) | −2151 | 3258 | 109 | 91 |
| H(33A) | 3077 | 6176 | 3812 | 107 |
| H(34A) | 3678 | 7775 | 3425 | 102 |
| H(36A) | 4020 | 6904 | 1500 | 101 |
| H(37A) | 4909 | 9722 | 2440 | 175 |
| H(37B) | 4697 | 9070 | 3103 | 175 |
| H(37C) | 3825 | 9162 | 2638 | 175 |
| H(41A) | 13172 | 11620 | 4862 | 73 |
| H(43A) | 10006 | 10913 | 4977 | 66 |
| H(47A) | 10339 | 11997 | 2080 | 100 |
| H(49A) | 8838 | 11150 | 3829 | 76 |
| H(53A) | 14389 | 14468 | 6912 | 101 |

TABLE 21-continued

Hydrogen Coordinates (×10$^4$) and Isotropic Displacement Parameters (A$^2$ × 10$^3$) for Compound 1 Polymorph Form C at Room Temperature

| Atom | x | y | z | U(eq) |
|---|---|---|---|---|
| H(54A) | 13903 | 13879 | 8007 | 103 |
| H(56A) | 13213 | 11214 | 7315 | 83 |
| H(57A) | 12855 | 11299 | 9122 | 203 |
| H(57B) | 13458 | 11109 | 8527 | 203 |
| H(57C) | 12373 | 11002 | 8344 | 203 |
| H(61A) | 1786 | 3408 | −181 | 77 |
| H(63A) | 4972 | 4282 | −18 | 70 |
| H(67A) | 3943 | 961 | 1682 | 100 |
| H(69A) | 5871 | 3427 | 982 | 98 |
| H(73A) | 741 | 1302 | −2608 | 93 |
| H(74A) | 1280 | 2202 | −3613 | 83 |
| H(76A) | 1899 | 4615 | −2466 | 83 |
| H(77A) | 1957 | 4081 | −4763 | 173 |
| H(77B) | 1093 | 3203 | −4482 | 173 |
| H(77C) | 2159 | 3223 | −4439 | 173 |

Characterization Example 15

X-Ray Powder Diffraction Pattern for Compound 1 Polymorph Form C

Powder X-ray diffraction was used to characterize polymorph Form C of Compound 1. Data were obtained with a Philips X'PERT automated powder diffractometer, Model 3040. The diffractometer was equipped with automatic variable anti-scatter and divergence slits, X'Celerator RTMS detector, and Ni filter. The radiation was Cu-K(alpha) (45 kV, 40 mA). Data were collected at room temperature from 3 to 50 degrees 2-theta using a continuous scan with an equivalent step size of 0.02 degrees and a count time of 320 seconds per step in theta-theta geometry. Samples were lightly ground with an agate mortar and pestle as needed and prepared on low background silicon specimen holders as a thin layer of powdered material. MDI/Jade software version 9.1 was used with the International Committee for Diffraction Data database PDF4+2008 for phase identification. Cu-K(alpha1) X-ray diffraction maxima for Form C of Compound 1 were calculated using the MDI/Jade "Find Peaks" routine and are listed Table 22.

TABLE 22

2θ X-ray Maxima (in degrees) for Polymorph Form C of Compound 1

| 2θ |
|---|
| 7.691 |
| 7.991 |
| 11.133 |
| 12.587 |
| 13.305 |
| 13.757 |
| 15.463 |
| 16.683 |
| 17.198 |
| 18.035 |
| 18.636 |
| 18.939 |
| 19.389 |
| 19.889 |
| 20.312 |
| 20.476 |
| 20.909 |
| 21.797 |
| 22.214 |
| 23.299 |
| 23.547 |
| 24.103 |
| 24.269 |
| 24.438 |
| 25.371 |
| 25.674 |
| 25.956 |
| 26.409 |
| 27.395 |
| 28.498 |
| 28.728 |
| 29.808 |
| 30.149 |
| 30.634 |
| 31.272 |
| 31.619 |
| 32.056 |
| 32.898 |
| 33.594 |
| 33.813 |
| 36.6 |
| 37.389 |
| 38.054 |
| 38.442 |
| 38.651 |
| 40.661 |
| 40.86 |
| 41.721 |
| 42.498 |
| 45.142 |
| 45.99 |
| 46.229 |
| 48.188 |
| 49.561 |

Formulation/Utility

A solid form of Compound 1 will generally be used as a parasitic nematode control active ingredient in a composition, i.e. formulation, with at least one additional component selected from the group consisting of surfactants, solid diluents and liquid carriers (i.e. liquid fluids that carry the active and possibly other ingredients; also called liquid diluents). The formulation or composition ingredients are selected to be consistent with the physical properties of the active ingredient, mode of application and environmental factors such as soil type, moisture and temperature.

Useful formulations of nematocidal active ingredients generally include both liquid and solid compositions. Liquid compositions include solutions (e.g., emulsifiable concentrates), emulsions (including micro-emulsions), dispersions and suspensions, and combinations of these forms (e.g., suspo-emulsions). The term "suspension" particularly refers to a dispersion of particulates that has been stabilized by addition of a chemical additive to minimize or stop sedimentation of the active ingredient. In a dispersion or suspension of particulates (e.g., aqueous suspension concentrate and oil dispersion formulations), a liquid carrier forms a continuous liquid phase in which the particulates (e.g., of a solid form of Compound 1) are dispersed or suspended. In a composition that combines a suspension or dispersion of particulates with an emulsion containing a second (immiscible) liquid (e.g., a suspo-emulsion formulation), a liquid carrier forms a continuous liquid phase in which not only the particulates are suspended but also droplets (i.e. non-continuous liquid phase) of the second liquid are emulsified.

Dispersions and suspensions may be aqueous (i.e. containing mainly water as the liquid carrier) or non-aqueous (i.e., comprising water-immiscible organic compounds, commonly referred to as "oil", as the liquid carrier) according to the nature of the liquid carrier forming the continuous liquid phase. The general types of aqueous liquid compositions include soluble concentrates, suspension concentrates, capsule suspensions, concentrated emulsions, micro-emulsions and suspo-emulsions. Thus in suspo-emulsions the liquid carrier forming the continuous liquid phase is aqueous (i.e. contains water as its main constituent) and a water-immiscible liquid component is emulsified in the aqueous liquid carrier. The general types of non-aqueous liquid compositions include emulsifiable concentrates, micro-emulsifiable concentrates, dispersible concentrates and oil dispersions. Suspension concentrates contain particulates dispersed in a continuous liquid phase and exists as particulate dispersions on addition to water. Suspo-emulsions and oil dispersions form both particulate dispersions and emulsions that coexist on addition to water, where one or more of these phases may contain active ingredient. (In the present compositions, the particulate dispersions comprise a solid form of Compound 1.)

The general types of solid compositions include dusts, powders, granules, pellets, prills, pastilles, tablets, filled films (including seed coatings) and the like, which can be water-dispersible ("wettable") or water-soluble. Films and coatings formed from film-forming liquids are particularly useful for seed treatment, in addition to having applications in both liquid and solid formulation types in general. Active ingredients can be encapsulated (including micro-encapsulated) and further formed into a liquid suspension or dispersion or into a solid formulation, to protect the active ingredient or control or delay release of the active ingredient on application to the target. Alternatively, the entire formulation, including the active ingredient, can be encapsulated (or "overcoated"). Encapsulation can also control or delay release of the active ingredient. High-strength compositions can be prepared and used as intermediates for subsequent use in preparing lower strength liquid and solid formulations.

Sprayable formulations are typically extended in a suitable medium before spraying. Such liquid and solid formulations are formulated to be readily diluted in the spray medium, usually water. Spray volumes can range from about one to several thousand liters per hectare, but more typically are in the range from about ten to several hundred liters per hectare. Sprayable formulations can be tank mixed with water or another suitable medium for foliar treatment by aerial or ground application, or for application to the growing medium of the plant. Liquid and dry formulations can be metered directly into drip irrigation systems or metered into the furrow during planting. Liquid and solid formulations can be applied onto seeds of crops and other desirable vegetation as seed treatments before planting to protect developing roots and other subterranean plant parts and/or foliage through systemic uptake.

Although the solid forms of Compound 1 according to the present invention can be used to prepare liquid solutions, emulsifiable concentrates and emulsions by combining with a solvent dissolving the solid forms, the solid forms can only retain their identity in formulated compositions containing Compound 1 as a solid (e.g., particles). The nematocidal compositions of the present invention wherein the composition comprises at least one solid form of Compound 1 thus include liquid compositions containing Compound 1 as a solid (e.g., dispersions, suspensions, suspo-emulsions) and solid compositions of Compound 1.

Even though all polymorph forms and the amorphous solid form of Compound 1 can be used to prepare nematocidal compositions of the present invention, polymorph Form A is particularly useful for forming nematocidal compositions, especially liquid compositions, having excellent physical as well as chemical stability. Although all polymorph forms and the amorphous solid form of Compound 1 are relatively stable (metastable) when isolated and maintained near room temperature, they are nevertheless thermodynamically unstable relative to polymorph Form A. Therefore, they are inherently susceptible to conversion to polymorph Form A. Contact with moisture, subjection to higher temperatures or long time periods may promote conversion to a more stable crystal form. Contact with solvents generally also promotes conversion of crystal forms. Therefore liquid compositions comprising other polymorph forms, mixtures of polymorph forms or the amorphous solid form of Compound 1 are particularly vulnerable to spontaneous recrystallization to polymorph Form A (see Preparation Example 7). Because of minimal nucleation and slow growth, the polymorph Form A crystals formed will be relatively few and large. This can result in both decreased biological efficacy and increased settling of the active ingredient, because high biological activity and suspensibility depend upon small particle size of solid active ingredient dispersed in liquid compositions. Using polymorph Form A to prepare nematocidal compositions removes the risk of later recrystallization in the compositions. Also, a formulation containing a less stable crystal form than Form A may change its biological activity over the course of its shelf life as the ratio of crystal forms change. This is generally highly undesired as required use rates (amount of active ingredient per hectare) would change unpredictably. Accordingly, of note is a nematocidal composition of the invention comprising polymorph Form A of Compound 1.

Both liquid and solid formulations comprising at least one solid form of Compound 1 will typically contain effective amounts of active ingredient, solid diluent or liquid carrier, and surfactant within the following approximate ranges, which add up to 100 percent by weight. General ranges of amounts of active ingredient (i.e. a solid form of Compound 1 and optionally other active ingredients), diluent and surfactant components in the present composition comprising at least one solid form of Compound 1 are as follows:

| | Composition in Weight Percent | | |
|---|---|---|---|
| Formulation Type | Active Ingredient | Diluent | Surfactant |
| Water-Dispersible Granules, Tablets and Powders | 0.001-90 | 0-99.999 | 0-25 |
| Oil Dispersions, Aqueous Suspensions | 1-60 | 40-99 | 0-50 |
| Dusts | 1-25 | 70-99 | 0-5 |
| Granules and Pellets | 0.001-95 | 5-99.999 | 0-20 |
| High Strength Compositions | 90-99 | 0-10 | 0-10 |

Solid diluents include, for example, clays such as bentonite, montmorillonite, attapulgite and kaolin, gypsum, cellulose, titanium dioxide, zinc oxide, starch, dextrin, sugars (e.g., lactose, sucrose), silica, talc, mica, diatomaceous earth, urea, calcium carbonate, sodium carbonate and bicarbonate, and sodium sulfate. Typical solid diluents are described in Watkins et al., *Handbook of Insecticide Dust Diluents and Carriers,* 2nd Ed., Dorland Books, Caldwell, N.J.

Liquid diluents include, for example, water, N,N-dimethylalkanamides (e.g., N,N-dimethylformamide), limonene, dimethyl sulfoxide, N-alkylpyrrolidones (e.g., N-methylpyrrolidinone), ethylene glycol, triethylene glycol, propylene glycol, dipropylene glycol, polypropylene glycol, propylene carbonate, butylene carbonate, paraffins (e.g., white mineral oils, normal paraffins, isoparaffins), alkylbenzenes, alkylnaphthalenes, glycerine, glycerol triacetate, sorbitol, triacetin, aromatic hydrocarbons, dearomatized aliphatics, alkylbenzenes, alkylnaphthalenes, ketones such as cyclohexanone, 2-heptanone, isophorone and 4-hydroxy-4-methyl-2-pentanone, acetates such as isoamyl acetate, hexyl acetate, heptyl acetate, octyl acetate, nonyl acetate, tridecyl acetate and isobornyl acetate, other esters such as alkylated lactate esters, dibasic esters and γ-butyrolactone, and alcohols, which can be linear, branched, saturated or unsaturated, such as methanol, ethanol, n-propanol, isopropyl alcohol, n-butanol, isobutyl alcohol, n-hexanol, 2-ethylhexanol, n-octanol, decanol, isodecyl alcohol, isooctadecanol, cetyl alcohol, lauryl alcohol, tridecyl alcohol, oleyl alcohol, cyclohexanol, tetrahydrofurfuryl alcohol, diacetone alcohol and benzyl alcohol. Liquid diluents also include glycerol esters of saturated and unsaturated fatty acids (typically $C_6$-$C_{22}$), such as plant seed and fruit oils (e.g., oils of olive, castor, linseed, sesame, corn (maize), peanut, sunflower, grapeseed, safflower, cottonseed, soybean, rapeseed, coconut and palm kernel), animal-sourced fats (e.g., beef tallow, pork tallow, lard, cod liver oil, fish oil), and mixtures thereof. Liquid diluents also include alkylated fatty acids (e.g., methylated, ethylated, butylated) wherein the fatty acids may be obtained by hydrolysis of glycerol esters from plant and animal sources, and can be purified by distillation. Typical liquid diluents are described in Marsden, *Solvents Guide,* 2nd Ed., Interscience, New York, 1950.

The solid and liquid compositions of the present invention often include one or more surfactants. When added to a liquid, surfactants (also known as "surface-active agents") generally modify, most often reduce, the surface tension of the liquid. Depending on the nature of the hydrophilic and lipophilic groups in a surfactant molecule, surfactants can be useful as wetting agents, dispersants, emulsifiers or defoaming agents.

Surfactants can be classified as nonionic, anionic or cationic. Nonionic surfactants useful for the present compositions include, but are not limited to: alcohol alkoxylates such as alcohol alkoxylates based on natural and synthetic alcohols (which may be branched or linear) and prepared from the alcohols and ethylene oxide, propylene oxide, butylene oxide or mixtures thereof; amine ethoxylates, alkanolamides and ethoxylated alkanolamides; alkoxylated triglycerides such as ethoxylated soybean, castor and rapeseed oils; alkylphenol alkoxylates such as octylphenol ethoxylates, nonylphenol ethoxylates, dinonyl phenol ethoxylates and dodecyl phenol ethoxylates (prepared from the phenols and ethylene oxide, propylene oxide, butylene oxide or mixtures thereof); block polymers prepared from ethylene oxide or propylene oxide and reverse block polymers where the terminal blocks are prepared from propylene oxide; ethoxylated fatty acids; ethoxylated fatty esters and oils; ethoxylated methyl esters; ethoxylated tristyrylphenol (including those prepared from ethylene oxide, propylene oxide, butylene oxide or mixtures thereof); fatty acid esters, glycerol esters, lanolin-based derivatives, polyethoxylate esters such as polyethoxylated sorbitan fatty acid esters, polyethoxylated sorbitol fatty acid esters and polyethoxylated glycerol fatty acid esters; other sorbitan derivatives such as sorbitan esters; polymeric surfactants such as random copolymers, block copolymers, alkyd peg (polyethylene glycol) resins, graft or comb polymers and star polymers; polyethylene glycols (pegs); polyethylene glycol fatty acid esters; silicone-based surfactants; and sugar-derivatives such as sucrose esters, alkyl polyglycosides and alkyl polysaccharides.

Useful anionic surfactants include, but are not limited to: alkylaryl sulfonic acids and their salts; carboxylated alcohol or alkylphenol ethoxylates; diphenyl sulfonate derivatives; lignin and lignin derivatives such as lignosulfonates; maleic or succinic acids or their anhydrides; olefin sulfonates; phosphate esters such as phosphate esters of alcohol alkoxylates, phosphate esters of alkylphenol alkoxylates and phosphate esters of styryl phenol ethoxylates; protein-based surfactants; sarcosine derivatives; styryl phenol ether sulfate; sulfates and sulfonates of oils and fatty acids; sulfates and sulfonates of ethoxylated alkylphenols; sulfates of alcohols; sulfates of ethoxylated alcohols; sulfonates of amines and amides such as N,N-alkyltaurates; sulfonates of benzene, cumene, toluene, xylene, and dodecyl and tridecylbenzenes; sulfonates of condensed naphthalenes; sulfonates of naphthalene and alkyl naphthalene; sulfonates of fractionated petroleum; sulfosuccinamates; and sulfosuccinates and their derivatives such as dialkyl sulfosuccinate salts.

Useful cationic surfactants include, but are not limited to: amides and ethoxylated amides; amines such as N-alkyl propanediamines, tripropylenetriamines and dipropylenetetramines, and ethoxylated amines, ethoxylated diamines and propoxylated amines (prepared from the amines and ethylene oxide, propylene oxide, butylene oxide or mixtures thereof); amine salts such as amine acetates and diamine salts; quaternary ammonium salts such as simple quaternary salts, ethoxylated quaternary salts and diquaternary salts; and amine oxides such as alkyldimethylamine oxides and bis-(2-hydroxyethyl)-alkylamine oxides.

Also useful for the present compositions are mixtures of nonionic and anionic surfactants or mixtures of nonionic and cationic surfactants. Nonionic, anionic and cationic surfactants and their recommended uses are disclosed in a variety of published references including *McCutcheon's Emulsifiers and Detergents*, annual American and International Editions published by McCutcheon's Division, The Manufacturing Confectioner Publishing Co.; Sisely and Wood, *Encyclopedia of Surface Active Agents*, Chemical Publ. Co., Inc., New York, 1964; and A. S. Davidson and B. Milwidsky, *Synthetic Detergents*, Seventh Edition, John Wiley and Sons, New York, 1987.

Compositions of this invention may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic or pseudoplastic thickeners), in-container microbial growth (antimicrobials), product freezing (antifreezes), color (dyes/pigment dispersions), wash-off (film formers or sticking agents), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in *McCutcheon's Volume 2: Functional Materials*, annual International and North American editions published by McCutcheon's Division, The Manufacturing Confectioner Publishing Co.; and PCT Publication WO 03/024222.

The solid forms of Compound 1 and any other active ingredients are typically incorporated into the present compositions by dissolving the active ingredient in a solvent or by grinding in a liquid or dry diluent. Solutions, including emulsifiable concentrates, can be prepared by simply mixing the ingredients. If the solvent of a liquid composition intended for use as an emulsifiable concentrate is water-immiscible, an emulsifier is typically added to emulsify the active-containing solvent upon dilution with water. Active ingredient slurries, with particle diameters of up to 2000 μm can be wet milled using media mills to obtain particles with average diameters below 3 μm. Aqueous slurries can be made into finished suspension concentrates (see, for example, U.S. Pat. No. 3,060,084) or further processed by spray-drying to form water-dispersible granules. Dry formulations usually require dry milling processes, which produce average particle diameters in the 2 to 10 μm range. Dusts and powders can be prepared by blending and grinding (such as with a hammer mill or fluid-energy mill). Granules and pellets can be prepared by spraying the active material upon preformed granular carriers or by agglomeration techniques. See Browning, "Agglomeration", *Chemical Engineering, Dec.* 4, 1967, pages 147-48; *Perry's Chemical Engineer's Handbook,* 4th Ed., McGraw-Hill, New York, 1963, pages 8-57 and following, and WO 91/13546. Pellets can be prepared as described in U.S. Pat. No. 4,172,714. Water-dispersible and water-soluble granules can be prepared as taught in U.S. Pat. No. 4,144,050, U.S. Pat. No. 3,920,442 and DE 3,246,493. Tablets can be prepared as taught in U.S. Pat. No. 5,180,587, U.S. Pat. No. 5,232,701 and U.S. Pat. No. 5,208,030. Films can be prepared as taught in GB 2,095,558 and U.S. Pat. No. 3,299,566.

For further information regarding the art of formulation, see T. S. Woods, "The Formulator's Toolbox—Product Forms for Modern Agriculture" in *Pesticide Chemistry and Bioscience. The Food-Environment Challenge*, T. Brooks and T. R. Roberts, Eds., Proceedings of the 9th International Congress on Pesticide Chemistry, The Royal Society of Chemistry, Cambridge, 1999, pp. 120-133. See also U.S. Pat. No. 3,235,361, Col. 6, line 16 through Col. 7, line 19 and Examples 10-41; U.S. Pat. No. 3,309,192, Col. 5, line 43 through Col. 7, line 62 and Examples 8, 12, 15, 39, 41, 52, 53, 58, 132, 138-140, 162-164, 166, 167 and 169-182; U.S. Pat. No. 2,891,855, Col. 3, line 66 through Col. 5, line 17 and Examples 1-4: Klingman, *Weed Control as a Science*, John Wiley and Sons, Inc., New York, 1961, pages 81-96; Hance et al., *Weed Control Handbook,* 8th Ed., Blackwell Scientific Publications, Oxford, 1989; and *Developments in formulation technology*, PJB Publications, Richmond, UK, 2000.

The following formulation examples are presented to further illustrate but not limit the disclosure in any way whatsoever. All percentages are given by weight and all formulations are prepared using conventional techniques. Without further elaboration, it is believed that one skilled in the art using the preceding descriptions and references can utilize the present invention to its fullest extent.

Formulation Example A

| High Strength Concentrate | |
|---|---|
| polymorph Form A of Compound 1 | 98.5% |
| silica aerogel | 0.5% |
| synthetic amorphous fine silica | 1.0% |

Formulation Example B

| Wettable Powder | |
|---|---|
| polymorph Forms A and B of Compound 1 | 65.0% |
| dodecylphenol polyethylene glycol ether | 2.0% |
| sodium ligninsulfonate | 4.0% |
| sodium silicoaluminate | 6.0% |
| montmorillonite (calcined) | 23.0% |

Formulation Example C

| Granule | |
|---|---|
| polymorph Form A of Compound 1 | 10.0% |
| attapulgite granules (low volatile matter, 0.71/0.30 mm; U.S.S. No. 25-50 sieves) | 90.0% |

Formulation Example D

| Extruded Pellet | |
|---|---|
| polymorph Form A of Compound 1 | 25.0% |
| anhydrous sodium sulfate | 10.0% |
| crude calcium ligninsulfonate | 5.0% |
| sodium alkylnaphthalenesulfonate | 1.0% |
| calcium/magnesium bentonite | 59.0% |

Formulation Example E

| Emulsifiable Concentrate | |
|---|---|
| polymorph Forms A and B of Compound 1 | 10.0% |
| polyoxyethylene sorbitol hexoleate | 20.0% |
| $C_6$-$C_{10}$ fatty acid methyl ester | 70.0% |

Formulation Example F

| Microemulsion | |
|---|---|
| polymorph Form A of Compound 1 | 5.0% |
| polyvinylpyrrolidone-vinyl acetate copolymer | 30.0% |
| alkylpolyglycoside | 30.0% |
| glyceryl monooleate | 15.0% |
| water | 20.0% |

Formulation Example G

| Seed Treatment | |
|---|---|
| polymorph Form A of Compound 1 | 20.00% |
| polyvinylpyrrolidone-vinyl acetate copolymer | 5.00% |
| montan acid wax | 5.00% |
| calcium ligninsulfonate | 1.00% |
| polyoxyethylene/polyoxypropylene block copolymers | 1.00% |

-continued

| Seed Treatment | |
|---|---|
| stearyl alcohol (POE 20) | 2.00% |
| polyorganosilane | 0.20% |
| colorant red dye | 0.05% |
| water | 65.75% |

Formulation Example H

| Fertilizer Stick | |
|---|---|
| polymorph Form A of Compound 1 | 2.50% |
| pyrrolidone-styrene copolymer | 4.80% |
| tristyrylphenyl 16-ethoxylate | 2.30% |
| talc | 0.80% |
| corn starch | 5.00% |
| Nitrophoska ® Permanent 15-9-15 slow-release fertilizer (BASF) | 36.00% |
| kaolin | 38.00% |
| water | 10.60% |

The solid forms of Compound 1 and their compositions are thus useful agronomically for protecting field crops from parasitic nematodes, and also nonagronomically for protecting other horticultural crops and plants from phytophagous parasitic nematodes. This utility includes protecting crops and other plants (i.e. both agronomic and nonagronomic) that contain genetic material introduced by genetic engineering (i.e. transgenic) or modified by mutagenesis to provide advantageous traits. Examples of such traits include tolerance to herbicides, resistance to phytophagous pests (e.g., insects, mites, aphids, spiders, nematodes, snails, plant-pathogenic fungi, bacteria and viruses), improved plant growth, increased tolerance of adverse growing conditions such as high or low temperatures, low or high soil moisture, and high salinity, increased flowering or fruiting, greater harvest yields, more rapid maturation, higher quality and/or nutritional value of the harvested product, or improved storage or process properties of the harvested products. Transgenic plants can be modified to express multiple traits. Examples of plants containing traits provided by genetic engineering or mutagenesis include varieties of corn, cotton, soybean and potato expressing an insecticidal Bacillus thuringiensis toxin such as YIELD GARD®, KNOCKOUT®, STARLINK®, BOLLGARD®, NuCOTN® and NEWLEAF®, and herbicide-tolerant varieties of corn, cotton, soybean and rapeseed such as ROUNDUP READY®, LIBERTY LINK®, IMI®, STS® and CLEARFIELD®, as well as crops expressing N-acetyltransferase (GAT) to provide resistance to glyphosate herbicide, or crops containing the HRA gene providing resistance to herbicides inhibiting acetolactate synthase (ALS). The solid forms of Compound 1 and their compositions may interact synergistically with traits introduced by genetic engineering or modified by mutagenesis, thus enhancing phenotypic expression or effectiveness of the traits or increasing the parasitic nematode control effectiveness of the present compounds and compositions. In particular, the solid forms of Compound 1 and their compositions may interact synergistically with the phenotypic expression of proteins or other natural products toxic to parasitic nematodes to provide greater-than-additive control of these pests.

Compositions of this invention can also optionally comprise plant nutrients, e.g., a fertilizer composition comprising at least one plant nutrient selected from nitrogen, phosphorus, potassium, sulfur, calcium, magnesium, iron, copper, boron, manganese, zinc, and molybdenum. Of note are compositions comprising at least one fertilizer composition comprising at least one plant nutrient selected from nitrogen, phosphorus, potassium, sulfur, calcium and magnesium. Compositions of the present invention which further comprise at least one plant nutrient can be in the form of liquids or solids. Of note are solid formulations in the form of granules, small sticks or tablets. Solid formulations comprising a fertilizer composition can be prepared by mixing the compound or composition of the present invention with the fertilizer composition together with formulating ingredients and then preparing the formulation by methods such as granulation or extrusion. Alternatively solid formulations can be prepared by spraying a solution or suspension of a compound or composition of the present invention in a volatile solvent onto a previous prepared fertilizer composition in the form of dimensionally stable mixtures, e.g., granules, small sticks or tablets, and then evaporating the solvent.

Solid forms of Compound 1 can exhibit activity against a wide spectrum of parasitic nematodes that live or grow inside or feed on plants (e.g., foliage, fruit, stems, roots or seeds) or animals and humans (e.g., vascular or digestive systems or other tissues) and therefore damage growing and stored agronomic crops, forestry, greenhouse crops, ornamentals and nursery crops, or afflict animal and human health. Crops of particular interest are fruiting vegetables such as solanaceous and cucurbit crops, plantation crops such as banana and coffee, root crops such as potatoes, onion and carrots, and field crops such as tobacco, peanut, cotton, sugarcane and soybean.

Solid forms of Compound 1 can have activity on members of both classes Adenophorea and Secernentea of the Phylum Nematoda, including economically important members of the orders Enoplida, Dorylaimida, Rhabditida, Strongylida, Ascarida, Oxyurida, Spirurida, Tylenchida and Aphelenchida, such as but not limited to economically important agricultural pests such as root-knot nematodes of the genus *Meloidogyne*, cyst nematodes of the genera *Heterodera* and *Globodlera*, lesion nematodes of the genus *Pratylenchus*, reniform nematodes of the genus *Rotylenchulus*, burrowing nematodes of the genus *Radopholus*, sting nematodes of the genus *Belonolaimus*, spiral nematodes of the genera *Helicotylenchus* and *Scutellonema*, citrus nematodes of the genus *Tyvlenchulus*, stubby root nematodes of the genera *Trichodorus* and *Paratrichodorus*, dagger nematodes of the genus *Xiphinema*, stunt nematodes of the genus *Tylenchorhynchus*, needle nematodes of the genera *Longidorus* and *Paralongidorus*, lance nematodes of the genus *Hoplolaimus*, ring nematodes of the family Criconematidae, stem nematodes of the genera *Ditylenchus* and *Anguina*, and foliar/stem nematodes of the genera *Aphelenchoides* and *Rhadinaphelenchus*; and animal and human health parasites (i.e. economically important roundworms such as *Strongylus vulgaris* in horses, *Toxocara canis* in dogs, *Haemonchus contortus* in sheep, *Dirofilaria immitis* in dogs, etc.).

Of note is use of solid forms of Compound 1 for controlling southern root-knot nematode (*Meloidogyne incognila*). Those skilled in the art will appreciate that solid forms of Compound 1 are not equally effective against all growth stages of all nematodes.

Solid forms of Compound 1 can also have activity on members of the Phylum Platyhelminthes, classes Cestoda (Tapeworms) and Trematoda (Flukes), including parasites (i.e. economically important flukes and tapeworms) afflicting animal and human health (e.g., *Anoplocephala perfoliata* in horses, *Fasciola hepatica* in ruminants, etc.).

Solid forms of Compound 1 can also be mixed with one or more other biologically active compounds or agents including insecticides, fungicides, nematocides, bactericides, acaricides, herbicides, herbicide safeners, growth regulators such as insect molting inhibitors and rooting stimulants, chemosterilants, semiochemicals, repellents, attractants, pheromones, feeding stimulants, other biologically active compounds or entomopathogenic bacteria, virus or fungi to form a multi-component pesticide giving an even broader spectrum of agronomic and nonagronomic utility. Thus the present invention also pertains to a composition comprising a solid form of Compound 1 and an effective amount of at least one additional biologically active compound or agent and can further comprise at least one of surfactants, solid diluents or liquid diluents. For mixtures of the present invention, the other biologically active compounds or agents can be formulated together with the solid forms of Compound 1, to form a premix, or the other biologically active compounds or agents can be formulated separately from the solid forms of Compound 1 and the two formulations combined together before application (e.g., in a spray tank) or, alternatively, applied in succession.

Examples of such biologically active compounds or agents with which solid forms of Compound 1 can be formulated are insecticides such as abamectin, acephate, acequinocyl, acetamiprid, acrinathrin, amidoflumet, amitraz, avermectin, azadirachtin, azinphos-methyl, bifenthrin, bifenazate, bistrifluoron, borate, buprofezin, cadusafos, carbaryl, carbofuran, cartap, carzol, chlorantraniliprole, chlorfenapyr, chlorfluazuron, chlorpyrifos, chlorpyrifos-methyl, chromafenozide, clofentezin, clothianidin, cyantraniliprole, cyflumetofen, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, diafenthiuron, diazinon, dieldrin, diflubenzuron, dimefluthrin, dimehypo, dimethoate, dinotefuran, diofenolan, emamectin, endosulfan, esfenvalerate, ethiprole, etofenprox, etoxazole, fenbutatin oxide, fenothiocarb, fenoxycarb, fenpropathrin, fenvalerate, fipronil, flonicamid, flubendiamide, flucythrinate, flufenerim, flufenoxuron, fluvalinate, tau-fluvalinate, fonophos, formetanate, fosthiazate, halofenozide, hexaflumuron, hexythiazox, hydramethylnon, imidacloprid, indoxacarb, insecticidal soaps, isofenphos, lufenuron, malathion, metaflumizone, metaldehyde, methamidophos, methidathion, methiodicarb, methomyl, methoprene, methoxychlor, metofluthrin, monocrotophos, methoxyfenozide, nitenpyram, nithiazine, novaluron, noviflumuron, oxamyl, parathion, parathion-methyl, permethrin, phorate, phosalone, phosmet, phosphamidon, pirimicarb, profenofos, profluthrin, propargite, protrifenbute, pymetrozine, pyrafluprole, pyrethrin, pyridaben, pyridalyl, pyrifluquinazon, pyriprole, pyriproxyfen, rotenone, ryanodine, spinetoram, spinosad, spirodiclofen, spiromesifen, spirotetramat, sulprofos, tebufenozide, tebufenpyrad, teflubenzuron, tefluthrin, terbufos, tetrachlorvinphos, tetramethrin, thiacloprid, thiamethoxam, thiodicarb, thiosultap-sodium, tolfenpyrad, tralomethrin, triazamate, trichlorfon, triflumuron, *Bacillus thuringiensis* delta-endotoxins, entomopathogenic bacteria, entomopathogenic viruses and entomopathogenic fungi.

Of note are insecticides such as abamectin, acetamiprid, acrinathrin, amitraz, avermectin, azadirachtin, bifenthrin, buprofezin, cadusafos, carbaryl, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

One embodiment of biological agents for mixing with solid forms of Compound 1 include entomopathogenic bacteria such as *Bacillus thuringiensis*, and the encapsulated delta-endotoxins of *Bacillus thuringiensis* such as MVP® and MVPII® bioinsecticides prepared by the CellCap® process (CellCap®, MVP® and MVPTII® are trademarks of Mycogen Corporation, Indianapolis, Ind., USA); entomopathogenic fungi such as green muscardine fungus; and entomopathogenic (both naturally occurring and genetically modified) viruses including baculovirus, nucleopolyhedro virus (NPV) such as *Helicoverpa zea* nucleopolyhedrovirus (HzNPV), *Anagrapha falcifera* nucleopolyhedrovirus (AfNPV); and granulosis virus (GV) such as *Cydia pomonella* granulosis virus (CpGV).

Of particular note is such a combination where the other invertebrate pest control active ingredient belongs to a different chemical class or has a different site of action than solid forms of Compound 1. In certain instances, a combination with at least one other invertebrate pest control active ingredient having a similar spectrum of control but a different site of action will be particularly advantageous for resistance management. Thus, a composition of the present invention can further comprise at least one additional invertebrate pest control active ingredient having a similar spectrum of control but belonging to a different chemical class or having a different site of action. These additional biologically active compounds or agents include, but are not limited to, sodium channel modulators such as bifenthrin, cypermethrin, cyhalothrin, lambda-cyhalothrin, cyfluthrin, beta-cyfluthrin, deltamethrin, dimefluthrin, esfenvalerate, fenvalerate, indoxacarb, metofluthrin, profluthrin, pyrethrin and tralomethrin; cholinesterase inhibitors such as chlorpyrifos, methomyl, oxamyl, thiodicarb and triazamate: neonicotinoids such as acetamiprid, clothianidin, dinotefuran, imidacloprid, nitenpyram, nithiazine, thiacloprid and thiamethoxam; insecticidal macrocyclic lactones such as spinetoram, spinosad, abamectin, avermectin and emamectin; GABA (γ-aminobutyric acid)-gated chloride channel antagonists such as avermectin or blockers such as ethiprole and fipronil; chitin synthesis inhibitors such as buprofezin, cyromazine, flufenoxuron, hexaflumuron, lufenuron, novaluron, noviflumuron and triflumuron; juvenile hormone mimics such as diofenolan, fenoxycarb, methoprene and pyriproxyfen; octopamine receptor ligands such as amitraz; molting inhibitors and ecdysone agonists such as azadirachtin, methoxyfenozide and tebufenozide; ryanodine receptor ligands such as ryanodine, anthranilic diamides such as chlorantraniliprole, cyantraniliprole and flubendiamide; nereistoxin analogs such as cartap; mitochondrial electron transport inhibitors such as chlorfenapyr, hydramethylnon and pyridaben; lipid biosynthesis inhibitors such as spirodiclofen and spiromesifen; cyclodiene insecticides such as dieldrin or endosulfan: pyrethroids; carbamates: insecticidal ureas; and biological agents including nucleopolyhedro viruses (NPV), members of *Bacillus thuringiensis*, encapsulated delta-endotoxins of *Bacillus thuringiensis*, and other naturally occurring or genetically modified insecticidal viruses.

Further examples of biologically active compounds or agents with which solid forms of Compound 1 can be formulated are: fungicides such as acibenzolar, aldimorph, amisulbrom, azaconazole, azoxystrobin, benalaxyl, benomyl, benthiavalicarb, benthiavalicarb-isopropyl, binomial, biphenyl, bitertanol, blasticidin-S, Bordeaux mixture (Tribasic copper sulfate), boscalid/nicobifen, bromuconazole, bupirimate, buthiobate, carboxin, carpropamid, captafol, captan, carbendazim, chloroneb, chlorothalonil, chlozolinate, clotrimazole, copper oxychloride, copper salts such as copper sulfate and copper hydroxide, cyazofamid, cyflunamid, cymoxanil, cyproconazole, cyprodinil, dichlofluanid, diclocymet, diclomezine, dicloran, diethofencarb, difenoconazole, dimethomorph, dimoxystrobin, diniconazole, diniconazole-M, dinocap, discostrobin, dithianon, dodemorph, dodine, econazole, etaconazole, edifenphos, epoxiconazole, ethaboxam, ethirimol, ethridiazole, famoxadone, fenamidone, fenarimol, fenbuconazole, fencaramid, fenfuram, fenhexamide, fenoxanil, fenpiclonil, fenpropidin, fenpropimorph, fentin acetate, fentin hydroxide, ferbam, ferfurazoate, ferimzone, fluazinam, fludioxonil, flumetover, fluopicolide, fluoxastrobin, fluquinconazole, fluquinconazole, flusilazole, flusulfamide, flutolanil, flutriafol, folpet, fosetyl-aluminum, fuberidazole, furalaxyl, furametapyr, hexaconazole, hymexazole, guazatine, imazalil, imibenconazole, iminoctadine, iodicarb, ipconazole, iprobenfos, iprodione, iprovalicarb, isoconazole, isoprothiolane, kasugamycin, kresoxim-methyl, mancozeb, mandipropamid, maneb, mapanipyrin, mefenoxam, mepronil, metalaxyl, metconazole, methasulfocarb, metiram, metominostrobinifenominostrobin, mepanipyrim, metrafenone, miconazole, myclobutanil, neo-asozin (ferric methanearsonate), nuarimol, octhilinone, ofurace, orysastrobin, oxadixyl, oxolinic acid, oxpoconazole, oxycarboxin, paclobutrazol, penconazole, pencycuron, penthiopyrad, perfurazoate, phosphonic acid, phthalide, picobenzamid, picoxystrobin, polyoxin, probenazole, prochloraz, procymidone, propamocarb, propamocarb-hydrochloride, propiconazole, propineb, proquinazid, prothioconazole, pyraclostrobin, pryazophos, pyrifenox, pyrimethanil, pyrifenox, pyrolnitrine, pyroquilon, quinconazole, quinoxyfen, quintozene, silthiofam, simeconazole, spiroxamine, streptomycin, sulfur, tebuconazole, techrazene, tecloftalam, tecnazene, tetraconazole, thiabendazole, thifluzamide, thiophanate, thiophanate-methyl, thiram, tiadinil, tolclofos-methyl, tolyfluanid, triadimefon, triadimenol, triarimol, triazoxide, tridemorph, trimoprhamide tricyclazole, trifloxystrobin, triforine, triticonazole, uniconazole, validamycin, vinclozolin, zineb, ziram, and zoxamide; nematocides such as aldicarb, imicyafos, oxamyl and fenamiphos; bactericides such as streptomycin; acaricides such as amitraz, chinomethionat, chlorobenzilate, cyhexatin, dicofol, dienochlor, etoxazole, fenazaquin, fenbutatin oxide, fenpropathrin, fenpyroximate, hexythiazox, propargite, pyridaben and tebufenpyrad.

In certain instances, combinations of solid forms of Compound 1 with other biologically active (particularly invertebrate pest control) compounds or agents (i.e. active ingredients) can result in a greater-than-additive (i.e. synergistic) effect. Reducing the quantity of active ingredients released in the environment while ensuring effective pest control is always desirable. When synergism with invertebrate pest control active ingredients occurs at application rates giving agronomically satisfactory levels of invertebrate pest control, such combinations can be advantageous for reducing crop production cost and decreasing environmental load.

Solid forms of Compound 1 and compositions thereof can be applied to plants genetically transformed to express proteins toxic to invertebrate pests (such as *Bacillus thuringiensis* delta-endotoxins). Such an application may provide a broader spectrum of plant protection and be advantageous for resistance management. The effect of the exogenously applied compounds of this invention may be synergistic with the expressed toxin proteins.

General references for these agricultural protectants (i.e. insecticides, fungicides, nematocides, acaricides, herbicides and biological agents) include The Pesticide Manual, 13th Edition, C. D. S. Tomlin, Ed., British Crop Protection Council, Farnham, Surrey, U.K., 2003 and The BioPesticide Manual, $2^{nd}$ Edition, L. G. Copping, Ed., British Crop Protection Council, Farnham, Surrey, U.K., 2001.

For embodiments where one or more of these various mixing partners are used, the weight ratio of these various mixing partners (in total) to a solid form of Compound 1 is typically between about 1:3000 and about 3000:1. Of note are weight ratios between about 1:300 and about 300:1 (for example ratios between about 1:30 and about 30:1). One skilled in the art can easily determine through simple experimentation the biologically effective amounts of active ingredients necessary for the desired spectrum of biological activity. It will be evident that including these additional components can expand the spectrum of parasitic nematodes controlled beyond the spectrum controlled by a solid form of Compound 1 alone.

Table A lists specific combinations of a solid form of Compound 1 with other invertebrate pest control agents illustrative of the mixtures, compositions and methods of the present invention and includes additional embodiments of weight ratio ranges for application rates. The first column of Table A lists the specific invertebrate control agents (e.g., "Abamectin" in the first line). The second column of Table A lists the mode of action (if known) or chemical class of the invertebrate pest control agents. The third column of Table A lists embodiment(s) of ranges of weight ratios for rates at which the invertebrate pest control agent can be applied relative to a solid form of Compound 1 (e.g., "50:1 to 1:50" of abamectin relative to a solid form of Compound 1 by weight). Thus, for example, the first line of Table A specifically discloses the combination of a solid form of Compound 1 with abamectin can be applied in a weight ratio between 50:1 to 1:50. The remaining lines of Table A are to be construed similarly.

TABLE A

| Invertebrate Pest Control Agent | Mode of Action or Chemical Class | Typical Weight Ratio |
|---|---|---|
| Abamectin | macrocyclic lactones | 50:1 to 1:50 |
| Acetamiprid | neonicotinoids | 150:1 to 1:200 |
| Amitraz | octopamine receptor ligands | 200:1 to 1:100 |
| Avermectin | macrocyclic lactones | 50:1 to 1:50 |
| Azadirachtin | ecdysone agonists | 100:1 to 1:120 |
| Beta-cyfluthrin | sodium channel modulators | 150:1 to 1:200 |
| Bifenthrin | sodium channel modulators | 100:1 to 1:10 |
| Buprofezin | chitin synthesis inhibitors | 500:1 to 1:50 |
| Cartap | nereistoxin analogs | 100:1 to 1:200 |
| Chlorantraniliprole | ryanodine receptor ligands | 100:1 to 1:120 |
| Chlorfenapyr | mitochondrial electron transport inhibitors | 300:1 to 1:200 |
| Chlorpyrifos | cholinesterase inhibitors | 500:1 to 1:200 |
| Clothianidin | neonicotinoids | 100:1 to 1:400 |
| Cyantraniliprole | ryanodine receptor ligands | 100:1 to 1:120 |
| Cyfluthrin | sodium channel modulators | 150:1 to 1:200 |
| Cyhalothrin | sodium channel modulators | 150:1 to 1:200 |
| Cypermethrin | sodium channel modulators | 150:1 to 1:200 |
| Cyromazine | chitin synthesis inhibitors | 400:1 to 1:50 |

TABLE A-continued

| Invertebrate Pest Control Agent | Mode of Action or Chemical Class | Typical Weight Ratio |
|---|---|---|
| Deltamethrin | sodium channel modulators | 50:1 to 1:400 |
| Dieldrin | cyclodiene insecticides | 200:1 to 1:100 |
| Dinotefuran | neonicotinoids | 150:1 to 1:200 |
| Diofenolan | molting inhibitor | 150:1 to 1:200 |
| Emamectin | macrocyclic lactones | 50:1 to 1:10 |
| Endosulfan | cyclodiene insecticides | 200:1 to 1:100 |
| Esfenvalerate | sodium channel modulators | 100:1 to 1:400 |
| Ethiprole | GABA-regulated chloride channel blockers | 200:1 to 1:100 |
| Fenothiocarb | | 150:1 to 1:200 |
| Fenoxycarb | juvenile hormone mimics | 500:1 to 1:100 |
| Fenvalerate | sodium channel modulators | 150:1 to 1:200 |
| Fipronil | GABA-regulated chloride channel blockers | 150:1 to 1:100 |
| Flonicamid | | 200:1 to 1:100 |
| Flubendiamide | ryanodine receptor ligands | 100:1 to 1:120 |
| Flufenoxuron | chitin synthesis inhibitors | 200:1 to 1:100 |
| Hexaflumuron | chitin synthesis inhibitors | 300:1 to 1:50 |
| Hydramethylnon | mitochondrial electron transport inhibitors | 150:1 to 1:250 |
| Imidacloprid | neonicotinoids | 1000:1 to 1:1000 |
| Indoxacarb | sodium channel modulators | 200:1 to 1:50 |
| Lambda-cyhalothrin | sodium channel modulators | 50:1 to 1:250 |
| Lufenuron | chitin synthesis inhibitors | 500:1 to 1:250 |
| Metaflumizone | | 200:1 to 1:200 |
| Methomyl | cholinesterase inhibitors | 500:1 to 1:100 |
| Methoprene | juvenile hormone mimics | 500:1 to 1:100 |
| Methoxyfenozide | ecdysone agonists | 50:1 to 1:50 |
| Nitenpyram | neonicotinoids | 150:1 to 1:200 |
| Nithiazine | neonicotinoids | 150:1 to 1:200 |
| Novaluron | chitin synthesis inhibitors | 500:1 to 1:150 |
| Oxamyl | cholinesterase inhibitors | 200:1 to 1:200 |
| Pymetrozine | | 200:1 to 1:100 |
| Pyrethrin | sodium channel modulators | 100:1 to 1:10 |
| Pyridaben | mitochondrial electron transport inhibitors | 200:1 to 1:100 |
| Pyridalyl | | 200:1 to 1:100 |
| Pyriproxyfen | juvenile hormone mimics | 500:1 to 1:100 |
| Ryanodine | ryanodine receptor ligands | 100:1 to 1:120 |
| Spinetoram | macrocyclic lactones | 150:1 to 1:100 |
| Spinosad | macrocyclic lactones | 500:1 to 1:10 |
| Spirodiclofen | lipid biosynthesis inhibitors | 200:1 to 1:200 |
| Spiromesifen | lipid biosynthesis inhibitors | 200:1 to 1:200 |
| Tebufenozide | ecdysone agonists | 500:1 to 1:250 |
| Thiacloprid | neonicotinoids | 100:1 to 1:200 |
| Thiamethoxam | neonicotinoids | 1250:1 to 1:1000 |
| Thiodicarb | cholinesterase inhibitors | 500:1 to 1:400 |
| Thiosultap-sodium | | 150:1 to 1:100 |
| Tralomethrin | sodium channel modulators | 150:1 to 1:200 |
| Triazamate | cholinesterase inhibitors | 250:1 to 1:100 |
| Triflumuron | chitin synthesis inhibitors | 200:1 to 1:100 |
| *Bacillus thuringiensis* | biological agents | 50:1 to 1:10 |
| *Bacillus thuringiensis* delta-endotoxin | biological agents | 50:1 to 1:10 |
| NPV (e.g., Gemstar) | biological agents | 50:1 to 1:10 |

Of note is the composition of the present invention wherein the at least one additional biologically active compound or agent is selected from the invertebrate pest control agents listed in Table A above.

The weight ratios of a solid form of Compound 1 to the additional invertebrate pest control agent typically are between 1000:1 and 1:1000, with one embodiment being between 500:1 and 1:500, another embodiment being between 250:1 and 1:200 and another embodiment being between 100:1 and 1:50.

Listed below in Table B are embodiments of specific compositions comprising a solid form of Compound 1 (polymorph Form A) and an additional invertebrate pest control agent.

TABLE B

| Mixture No. | Cmpd. 1 Form and | Invertebrate Pest Control Agent | Typical Mixture Ratios (by weight) | | | | | | | | |
|---|---|---|---|---|---|---|---|---|---|---|---|
| B-1 | A and | Abamectin | 100:1 | 10:1 | 5:1 | 2:1 | 1:1 | 1:2 | 1:5 | 1:10 | 1:100 |
| B-2 | A and | Acetamiprid | 100:1 | 10:1 | 5:1 | 2:1 | 1:1 | 1:2 | 1:5 | 1:10 | 1:100 |
| B-3 | A and | Amitraz | 100:1 | 10:1 | 5:1 | 2:1 | 1:1 | 1:2 | 1:5 | 1:10 | 1:100 |
| B-4 | A and | Avermectin | 100:1 | 10:1 | 5:1 | 2:1 | 1:1 | 1:2 | 1:5 | 1:10 | 1:100 |
| B-5 | A and | Azadirachtin | 100:1 | 10:1 | 5:1 | 2:1 | 1:1 | 1:2 | 1:5 | 1:10 | 1:100 |
| B-5a | A and | Bensultap | 100:1 | 10:1 | 5:1 | 2:1 | 1:1 | 1:2 | 1:5 | 1:10 | 1:100 |
| B-6 | A and | Beta-cyfluthrin | 100:1 | 10:1 | 5:1 | 2:1 | 1:1 | 1:2 | 1:5 | 1:10 | 1:100 |
| B-7 | A and | Bifenthrin | 100:1 | 10:1 | 5:1 | 2:1 | 1:1 | 1:2 | 1:5 | 1:10 | 1:100 |
| B-8 | A and | Buprofezin | 100:1 | 10:1 | 5:1 | 2:1 | 1:1 | 1:2 | 1:5 | 1:10 | 1:100 |
| B-9 | A and | Cartap | 100:1 | 10:1 | 5:1 | 2:1 | 1:1 | 1:2 | 1:5 | 1:10 | 1:100 |
| B-10 | A and | Chlorantraniliprole | 100:1 | 10:1 | 5:1 | 2:1 | 1:1 | 1:2 | 1:5 | 1:10 | 1:100 |
| B-11 | A and | Chlorfenapyr | 100:1 | 10:1 | 5:1 | 2:1 | 1:1 | 1:2 | 1:5 | 1:10 | 1:100 |
| B-12 | A and | Chlorpyrifos | 100:1 | 10:1 | 5:1 | 2:1 | 1:1 | 1:2 | 1:5 | 1:10 | 1:100 |
| B-13 | A and | Clothianidin | 100:1 | 10:1 | 5:1 | 2:1 | 1:1 | 1:2 | 1:5 | 1:10 | 1:100 |
| B-14 | A and | Cyantraniliprole | 100:1 | 10:1 | 5:1 | 2:1 | 1:1 | 1:2 | 1:5 | 1:10 | 1:100 |
| B-15 | A and | Cyfluthrin | 100:1 | 10:1 | 5:1 | 2:1 | 1:1 | 1:2 | 1:5 | 1:10 | 1:100 |
| B-16 | A and | Cyhalothrin | 100:1 | 10:1 | 5:1 | 2:1 | 1:1 | 1:2 | 1:5 | 1:10 | 1:100 |
| B-17 | A and | Cypermethrin | 100:1 | 10:1 | 5:1 | 2:1 | 1:1 | 1:2 | 1:5 | 1:10 | 1:100 |
| B-18 | A and | Cyromazine | 100:1 | 10:1 | 5:1 | 2:1 | 1:1 | 1:2 | 1:5 | 1:10 | 1:100 |
| B-19 | A and | Deltamethrin | 100:1 | 10:1 | 5:1 | 2:1 | 1:1 | 1:2 | 1:5 | 1:10 | 1:100 |
| B-20 | A and | Dieldrin | 100:1 | 10:1 | 5:1 | 2:1 | 1:1 | 1:2 | 1:5 | 1:10 | 1:100 |
| B-21 | A and | Dinotefuran | 100:1 | 10:1 | 5:1 | 2:1 | 1:1 | 1:2 | 1:5 | 1:10 | 1:100 |
| B-22 | A and | Diofenolan | 100:1 | 10:1 | 5:1 | 2:1 | 1:1 | 1:2 | 1:5 | 1:10 | 1:100 |
| B-23 | A and | Emamectin | 100:1 | 10:1 | 5:1 | 2:1 | 1:1 | 1:2 | 1:5 | 1:10 | 1:100 |
| B-24 | A and | Endosulfan | 100:1 | 10:1 | 5:1 | 2:1 | 1:1 | 1:2 | 1:5 | 1:10 | 1:100 |
| B-25 | A and | Esfenvalerate | 100:1 | 10:1 | 5:1 | 2:1 | 1:1 | 1:2 | 1:5 | 1:10 | 1:100 |
| B-26 | A and | Ethiprole | 100:1 | 10:1 | 5:1 | 2:1 | 1:1 | 1:2 | 1:5 | 1:10 | 1:100 |
| B-27 | A and | Fenothiocarb | 100:1 | 10:1 | 5:1 | 2:1 | 1:1 | 1:2 | 1:5 | 1:10 | 1:100 |
| B-28 | A and | Fenoxycarb | 100:1 | 10:1 | 5:1 | 2:1 | 1:1 | 1:2 | 1:5 | 1:10 | 1:100 |
| B-29 | A and | Fenvalerate | 100:1 | 10:1 | 5:1 | 2:1 | 1:1 | 1:2 | 1:5 | 1:10 | 1:100 |
| B-30 | A and | Fipronil | 100:1 | 10:1 | 5:1 | 2:1 | 1:1 | 1:2 | 1:5 | 1:10 | 1:100 |
| B-31 | A and | Flonicamid | 100:1 | 10:1 | 5:1 | 2:1 | 1:1 | 1:2 | 1:5 | 1:10 | 1:100 |
| B-32 | A and | Flubendiamide | 100:1 | 10:1 | 5:1 | 2:1 | 1:1 | 1:2 | 1:5 | 1:10 | 1:100 |

TABLE B-continued

| Mixture No. | Cmpd. 1 Form and | Invertebrate Pest Control Agent | Typical Mixture Ratios (by weight) | | | | | | | | |
|---|---|---|---|---|---|---|---|---|---|---|---|
| B-33 | A and | Flufenoxuron | 100:1 | 10:1 | 5:1 | 2:1 | 1:1 | 1:2 | 1:5 | 1:10 | 1:100 |
| B-34 | A and | Hexaflumuron | 100:1 | 10:1 | 5:1 | 2:1 | 1:1 | 1:2 | 1:5 | 1:10 | 1:100 |
| B-35 | A and | Hydramethylnon | 100:1 | 10:1 | 5:1 | 2:1 | 1:1 | 1:2 | 1:5 | 1:10 | 1:100 |
| B-36 | A and | Imidacloprid | 100:1 | 10:1 | 5:1 | 2:1 | 1:1 | 1:2 | 1:5 | 1:10 | 1:100 |
| B-37 | A and | Indoxacarb | 100:1 | 10:1 | 5:1 | 2:1 | 1:1 | 1:2 | 1:5 | 1:10 | 1:100 |
| B-38 | A and | Lambda-cyhalothrin | 100:1 | 10:1 | 5:1 | 2:1 | 1:1 | 1:2 | 1:5 | 1:10 | 1:100 |
| B-39 | A and | Lufenuron | 100:1 | 10:1 | 5:1 | 2:1 | 1:1 | 1:2 | 1:5 | 1:10 | 1:100 |
| B-40 | A and | Metaflumizone | 100:1 | 10:1 | 5:1 | 2:1 | 1:1 | 1:2 | 1:5 | 1:10 | 1:100 |
| B-41 | A and | Methomyl | 100:1 | 10:1 | 5:1 | 2:1 | 1:1 | 1:2 | 1:5 | 1:10 | 1:100 |
| B-42 | A and | Methoprene | 100:1 | 10:1 | 5:1 | 2:1 | 1:1 | 1:2 | 1:5 | 1:10 | 1:100 |
| B-43 | A and | Methoxyfenozide | 100:1 | 10:1 | 5:1 | 2:1 | 1:1 | 1:2 | 1:5 | 1:10 | 1:100 |
| B-44 | A and | Nitenpyram | 100:1 | 10:1 | 5:1 | 2:1 | 1:1 | 1:2 | 1:5 | 1:10 | 1:100 |
| B-45 | A and | Nithiazine | 100:1 | 10:1 | 5:1 | 2:1 | 1:1 | 1:2 | 1:5 | 1:10 | 1:100 |
| B-46 | A and | Novaluron | 100:1 | 10:1 | 5:1 | 2:1 | 1:1 | 1:2 | 1:5 | 1:10 | 1:100 |
| B-47 | A and | Oxamyl | 100:1 | 10:1 | 5:1 | 2:1 | 1:1 | 1:2 | 1:5 | 1:10 | 1:100 |
| B-48 | A and | Phosmet | 100:1 | 10:1 | 5:1 | 2:1 | 1:1 | 1:2 | 1:5 | 1:10 | 1:100 |
| B-49 | A and | Pymetrozine | 100:1 | 10:1 | 5:1 | 2:1 | 1:1 | 1:2 | 1:5 | 1:10 | 1:100 |
| B-50 | A and | Pyrethrin | 100:1 | 10:1 | 5:1 | 2:1 | 1:1 | 1:2 | 1:5 | 1:10 | 1:100 |
| B-51 | A and | Pyridaben | 100:1 | 10:1 | 5:1 | 2:1 | 1:1 | 1:2 | 1:5 | 1:10 | 1:100 |
| B-52 | A and | Pyridalyl | 100:1 | 10:1 | 5:1 | 2:1 | 1:1 | 1:2 | 1:5 | 1:10 | 1:100 |
| B-53 | A and | Pyriproxyfen | 100:1 | 10:1 | 5:1 | 2:1 | 1:1 | 1:2 | 1:5 | 1:10 | 1:100 |
| B-54 | A and | Ryanodine | 100:1 | 10:1 | 5:1 | 2:1 | 1:1 | 1:2 | 1:5 | 1:10 | 1:100 |
| B-55 | A and | Spinetoram | 100:1 | 10:1 | 5:1 | 2:1 | 1:1 | 1:2 | 1:5 | 1:10 | 1:100 |
| B-56 | A and | Spinosad | 100:1 | 10:1 | 5:1 | 2:1 | 1:1 | 1:2 | 1:5 | 1:10 | 1:100 |
| B-57 | A and | Spirodiclofen | 100:1 | 10:1 | 5:1 | 2:1 | 1:1 | 1:2 | 1:5 | 1:10 | 1:100 |
| B-58 | A and | Spiromesifen | 100:1 | 10:1 | 5:1 | 2:1 | 1:1 | 1:2 | 1:5 | 1:10 | 1:100 |
| B-59 | A and | Spirotetramat | 100:1 | 10:1 | 5:1 | 2:1 | 1:1 | 1:2 | 1:5 | 1:10 | 1:100 |
| B-59a | A and | Sulfoxaflor | 100:1 | 10:1 | 5:1 | 2:1 | 1:1 | 1:2 | 1:5 | 1:10 | 1:100 |
| B-60 | A and | Tebufenozide | 100:1 | 10:1 | 5:1 | 2:1 | 1:1 | 1:2 | 1:5 | 1:10 | 1:100 |
| B-60a | A and | Tefluthrin | 100:1 | 10:1 | 5:1 | 2:1 | 1:1 | 1:2 | 1:5 | 1:10 | 1:100 |
| B-61 | A and | Thiacloprid | 100:1 | 10:1 | 5:1 | 2:1 | 1:1 | 1:2 | 1:5 | 1:10 | 1:100 |
| B-62 | A and | Thiamethoxam | 100:1 | 10:1 | 5:1 | 2:1 | 1:1 | 1:2 | 1:5 | 1:10 | 1:100 |
| B-63 | A and | Thiodicarb | 100:1 | 10:1 | 5:1 | 2:1 | 1:1 | 1:2 | 1:5 | 1:10 | 1:100 |
| B-64 | A and | Thiosultap-sodium | 100:1 | 10:1 | 5:1 | 2:1 | 1:1 | 1:2 | 1:5 | 1:10 | 1:100 |
| B-65 | A and | Tolfenpyrad | 100:1 | 10:1 | 5:1 | 2:1 | 1:1 | 1:2 | 1:5 | 1:10 | 1:100 |
| B-66 | A and | Tralomethrin | 100:1 | 10:1 | 5:1 | 2:1 | 1:1 | 1:2 | 1:5 | 1:10 | 1:100 |
| B-67 | A and | Triazamate | 100:1 | 10:1 | 5:1 | 2:1 | 1:1 | 1:2 | 1:5 | 1:10 | 1:100 |
| B-68 | A and | Triflumuron | 100:1 | 10:1 | 5:1 | 2:1 | 1:1 | 1:2 | 1:5 | 1:10 | 1:100 |
| B-69 | A and | *Bacillus thuringiensis* | 100:1 | 10:1 | 5:1 | 2:1 | 1:1 | 1:2 | 1:5 | 1:10 | 1:100 |
| B-70 | A and | *Bacillus thuringiensis* delta-endotoxin | 100:1 | 10:1 | 5:1 | 2:1 | 1:1 | 1:2 | 1:5 | 1:10 | 1:100 |
| B-71 | A and | NPV (e.g., Gemstar) | 100:1 | 10:1 | 5:1 | 2:1 | 1:1 | 1:2 | 1:5 | 1:10 | 1:100 |

Listed below in Table C are embodiments of specific compositions comprising a solid form of Compound 1 (polymorph Form A) and an additional fungicide.

TABLE C

| Mixture No. | Cmpd. 1 Form and | Fungicide | Typical Mixture Ratios (by weight) | | | | | | | | |
|---|---|---|---|---|---|---|---|---|---|---|---|
| C-1 | A and | Probenazole | 100:1 | 10:1 | 5:1 | 2:1 | 1:1 | 1:2 | 1:5 | 1:10 | 1:100 |
| C-2 | A and | Tiadinil | 100:1 | 10:1 | 5:1 | 2:1 | 1:1 | 1:2 | 1:5 | 1:10 | 1:100 |
| C-3 | A and | Isotianil | 100:1 | 10:1 | 5:1 | 2:1 | 1:1 | 1:2 | 1:5 | 1:10 | 1:100 |
| C-4 | A and | Pyroquilon | 100:1 | 10:1 | 5:1 | 2:1 | 1:1 | 1:2 | 1:5 | 1:10 | 1:100 |
| C-5 | A and | Metominostrobin | 100:1 | 10:1 | 5:1 | 2:1 | 1:1 | 1:2 | 1:5 | 1:10 | 1:100 |
| C-6 | A and | Flutolanil | 100:1 | 10:1 | 5:1 | 2:1 | 1:1 | 1:2 | 1:5 | 1:10 | 1:100 |
| C-7 | A and | Validamycin | 100:1 | 10:1 | 5:1 | 2:1 | 1:1 | 1:2 | 1:5 | 1:10 | 1:100 |
| C-8 | A and | Furametpyr | 100:1 | 10:1 | 5:1 | 2:1 | 1:1 | 1:2 | 1:5 | 1:10 | 1:100 |
| C-9 | A and | Pencycuron | 100:1 | 10:1 | 5:1 | 2:1 | 1:1 | 1:2 | 1:5 | 1:10 | 1:100 |
| C-10 | A and | Simeconazole | 100:1 | 10:1 | 5:1 | 2:1 | 1:1 | 1:2 | 1:5 | 1:10 | 1:100 |
| C-11 | A and | Orysastrobin | 100:1 | 10:1 | 5:1 | 2:1 | 1:1 | 1:2 | 1:5 | 1:10 | 1:100 |
| C-12 | A and | Trifloxystrobin | 100:1 | 10:1 | 5:1 | 2:1 | 1:1 | 1:2 | 1:5 | 1:10 | 1:100 |
| C-13 | A and | Isoprothiolane | 100:1 | 10:1 | 5:1 | 2:1 | 1:1 | 1:2 | 1:5 | 1:10 | 1:100 |
| C-14 | A and | Azoxystrobin | 100:1 | 10:1 | 5:1 | 2:1 | 1:1 | 1:2 | 1:5 | 1:10 | 1:100 |
| C-15 | A and | Tricyclazole | 100:1 | 10:1 | 5:1 | 2:1 | 1:1 | 1:2 | 1:5 | 1:10 | 1:100 |
| C-16 | A and | Hexaconazole | 100:1 | 10:1 | 5:1 | 2:1 | 1:1 | 1:2 | 1:5 | 1:10 | 1:100 |
| C-17 | A and | Difenoconazole | 100:1 | 10:1 | 5:1 | 2:1 | 1:1 | 1:2 | 1:5 | 1:10 | 1:100 |
| C-18 | A and | Cyproconazole | 100:1 | 10:1 | 5:1 | 2:1 | 1:1 | 1:2 | 1:5 | 1:10 | 1:100 |
| C-19 | A and | Propiconazole | 100:1 | 10:1 | 5:1 | 2:1 | 1:1 | 1:2 | 1:5 | 1:10 | 1:100 |

TABLE C-continued

| Mixture No. | Cmpd. 1 Form and | Fungicide | Typical Mixture Ratios (by weight) | | | | | | | | |
|---|---|---|---|---|---|---|---|---|---|---|---|
| C-20 | A and | Fenoxanil | 100:1 | 10:1 | 5:1 | 2:1 | 1:1 | 1:2 | 1:5 | 1:10 | 1:100 |
| C-21 | A and | Ferimzone | 100:1 | 10:1 | 5:1 | 2:1 | 1:1 | 1:2 | 1:5 | 1:10 | 1:100 |
| C-22 | A and | Fthalide | 100:1 | 10:1 | 5:1 | 2:1 | 1:1 | 1:2 | 1:5 | 1:10 | 1:100 |
| C-23 | A and | Kasugamycin | 100:1 | 10:1 | 5:1 | 2:1 | 1:1 | 1:2 | 1:5 | 1:10 | 1:100 |
| C-24 | A and | Picoxystrobin | 100:1 | 10:1 | 5:1 | 2:1 | 1:1 | 1:2 | 1:5 | 1:10 | 1:100 |
| C-25 | A and | Penthiopyrad | 100:1 | 10:1 | 5:1 | 2:1 | 1:1 | 1:2 | 1:5 | 1:10 | 1:100 |
| C-26 | A and | Famoxadone | 100:1 | 10:1 | 5:1 | 2:1 | 1:1 | 1:2 | 1:5 | 1:10 | 1:100 |
| C-27 | A and | Cymoxanil | 100:1 | 10:1 | 5:1 | 2:1 | 1:1 | 1:2 | 1:5 | 1:10 | 1:100 |
| C-28 | A and | Proquinazid | 100:1 | 10:1 | 5:1 | 2:1 | 1:1 | 1:2 | 1:5 | 1:10 | 1:100 |
| C-29 | A and | Flusilazole | 100:1 | 10:1 | 5:1 | 2:1 | 1:1 | 1:2 | 1:5 | 1:10 | 1:100 |
| C-30 | A and | Mancozeb | 100:1 | 10:1 | 5:1 | 2:1 | 1:1 | 1:2 | 1:5 | 1:10 | 1:100 |
| C-31 | A and | Copper hydroxide | 100:1 | 10:1 | 5:1 | 2:1 | 1:1 | 1:2 | 1:5 | 1:10 | 1:100 |
| C-32 | A and | Fluopyram | 100:1 | 10:1 | 5:1 | 2:1 | 1:1 | 1:2 | 1:5 | 1:10 | 1:100 |
| C-33 | A and | (a) | 100:1 | 10:1 | 5:1 | 2:1 | 1:1 | 1:2 | 1:5 | 1:10 | 1:100 |

(a) 1-[4-[4-[5-(2,6-difluorophenyl)-4,5-dihydro-3-isoxazolyl]-2-thiazolyl]-1-piperidinyl]-2-[5-methyl-3-(trifluoromethyl)-1H-pyrazol-1-yl]ethanone Parasitic nematodes are controlled in agronomic and nonagronomic applications by applying a solid form of Compound 1, typically in the form of a composition, in a biologically effective amount, to the environment of the pests, including the agronomic and/or nonagronomic locus of infestation, to the area to be protected, or directly on the pests to be controlled.

Thus the present invention comprises a method for controlling a parasitic nematode in agronomic and/or nonagronomic applications, comprising contacting the parasitic nematode or its environment with a biologically effective amount of a solid form of Compound 1 or with a composition comprising at least one such compound or a composition comprising at least one such compound and at least one additional biologically active compound or agent. Examples of suitable compositions comprising a solid form of Compound 1 and at least one additional biologically active compound or agent include granular compositions wherein the additional active compound is present on the same granule as the compound of the invention or on granules separate from those of the compound of the invention.

To achieve contact with a solid form of Compound 1 or composition of the invention to protect a field crop from parasitic nematodes, the solid form of Compound 1 or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition comprising a compound of the invention can be applied to the plant foliage or the soil. Solid forms of Compound 1 can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present invention in the form of a soil drench liquid formulation. Also of note is a method for controlling a parasitic nematode comprising contacting the parasitic nematode or its environment with a biologically effective amount of a solid form of Compound 1 or with a composition comprising a biologically effective amount of a solid form of Compound 1. Of further note is this method wherein the environment is soil and the composition is applied to the soil as a soil drench formulation. Of further note is that solid forms of Compound 1 are also effective by localized application to the locus of infestation. Other methods of contact include application of a solid form of Compound 1 or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact involves a dimensionally stable fertilizer granule, stick or tablet comprising a solid form of Compound 1 or composition of the invention. The solid forms of Compound 1 can also be impregnated into materials for fabricating invertebrate control devices (e.g., insect netting).

Solid forms of Compound 1 are also useful in seed treatments for protecting seeds from parasitic nematodes. In the context of the present disclosure and claims, treating a seed means contacting the seed with a biologically effective amount of a solid form of Compound 1 which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of Compound 1 or a second active ingredient within the developing plant. Seed treatments can be applied to all types of seeds, including those from which plants genetically transformed to express specialized traits will germinate. Representative examples of genetically transformed plants include those expressing proteins toxic to parasitic nematodes, such as *Bacillus thuringiensis* toxin or those expressing herbicide resistance such as glyphosate acetyltransferase, which provides resistance to glyphosate. Seed treatments with solid forms of Compound 1 can also increase vigor of plants growing from the seed.

One method of seed treatment is by spraying or dusting the seed with a solid form of Compound 1 (i.e. as a formulated composition) before sowing the seeds. Compositions formulated for seed treatment generally comprise a film former or adhesive agent. Therefore typically a seed coating composition of the present invention comprises a biologically effective amount of a solid form of Compound 1 and a film former or adhesive agent. Seed can be coated by spraying a flowable suspension concentrate directly into a tumbling bed of seeds and then drying the seeds. Alternatively, other formulation types such as wetted powders, solutions, suspo-emulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., *Seed Treat-* ment: *Progress and Prospects*, 1994 BCPC Mongraph No. 57, and references listed therein.

Solid forms of Compound 1 and their compositions, both alone and in combination with other insecticides, nematicides, and fungicides, are particularly useful in seed treatment for crops including, but not limited to, maize or corn, soybeans, cotton, cereal (e.g., wheat, oats, barley, rye and rice), potatoes, vegetables and oilseed rape.

Other insecticides or nematicides with which solid forms of Compound 1 can be formulated to provide mixtures useful in seed treatment include but are not limited to abamectin, acetamiprid, acrinathrin, amitraz, avermectin, azadirachtin, bensultap, bifenthrin, buprofezin, cadusafos, carbaryl, carbofuran, cartap, chlorantraniliprole, chlorfenapyr, chlorpyrifos, clothianidin, cyantraniliprole, cyfluthrin, beta-cyfluthrin, cyhalothrin, gamma-cyhalothrin, lambda-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, fosthiazate, hexaflumuron, hydramethylnon, imidacloprid, indoxacarb, lufenuron, metaflumizone, methiocarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, sulfoxaflor, tebufenozide, tetramethrin, thiacloprid, thiamethoxam, thiodicarb, thiosultap-sodium, tralomethrin, triazamate, triflumuron, *Bacillus thuringiensis* delta-endotoxins, all strains of *Bacillus thuringiensis* and all strains of *Nucleo polyhydrosis* viruses.

Fungicides with which solid forms of Compound 1 can be formulated to provide mixtures useful in seed treatment include but are not limited to amisulbrom, azoxystrobin, boscalid, carbendazim, carboxin, cymoxanil, cyproconazole, difenoconazole, dimethomorph, fluazinam, fludioxonil, fluquinconazole, fluopicolide, fluoxastrobin, flutriafol, fluxapyroxad, ipconazole, iprodione, metalaxyl, mefenoxam, metconazole, myclobutanil, paclobutrazole, penflufen, picoxystrobin, prothioconazole, pyraclostrobin, sedaxane, silthiofam, tebuconazole, thiabendazole, thiophanate-methyl, thiram, trifloxystrobin and triticonazole.

Compositions comprising solid forms of Compound 1 useful for seed treatment can further comprise bacteria and fungi that have the ability to provide protection from the harmful effects of plant pathogenic fungi or bacteria and/or soil born animals such as nematodes. Bacteria exhibiting nematicidal properties may include but are not limited to *Bacillus firmus, Bacillus cereus, Bacillius subtilis* and *Pasteuria penetrans*. A suitable *Bacillus firmus* strain is strain CNCM 1-1582 (GB-126) which is commercially available as BioNem™. A suitable *Bacillus cereus* strain is strain NCMM 1-1592. Both *Bacillus* strains are disclosed in U.S. Pat. No. 6,406,690. Other suitable bacteria exhibiting nematicidal activity are *B. amyloliquefaciens* IN937a and *B. subtilis* strain GB03. Bacteria exhibiting fungicidal properties may include but are not limited to *B. pumilus* strain GB34. Fungal species exhibiting nematicidal properties may include but are not limited to *Myrothecium verrucaria, Paecilomyces lilacinus* and *Purpureocillium lilacinum*.

Seed treatments can also include one or more nematicidal agents of natural origin such as the elicitor protein called harpin which is isolated from certain bacterial plant pathogens such as *Erwinia amylovora*. An example is the Harpin-N-Tek seed treatment technology available as N-Hibit™ Gold CST.

Seed treatments can also include one or more species of legume-root nodulating bacteria such as the microsymbiotic nitrogen-fixing bacteria *Bradvrhizobium japonicum*. These inocculants can optionally include one or more lipo-chitooligosaccharides (LCOs), which are nodulation (Nod) factors produced by *rhizobia* bacteria during the initiation of nodule formation on the roots of legumes. For example, the Optimize® brand seed treatment technology incorporates LCO Promoter Technology™ in combination with an inocculant.

Seed treatments can also include one or more isoflavones which can increase the level of root colonization by mycorrhizal fungi. Mycorrhizal fungi improve plant growth by enhancing the root uptake of nutrients such as water, sulfates, nitrates, phosphates and metals. Examples of isoflavones include, but are not limited to, genistein, biochanin A, formononetin, daidzein, glycitein, hesperetin, naringenin and pratensein. Formononetin is available as an active ingredient in mycorrhizal inocculant products such as PHC Colonize® AG.

Seed treatments can also include one or more plant activators that induce systemic acquired resistance in plants following contact by a pathogen. An example of a plant activator which induces such protective mechanisms is acibenzolar-S-methyl.

The treated seed typically comprises a solid form of Compound 1 in an amount from about 0.1 g to 1 kg per 100 kg of seed (i.e. from about 0.0001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

The solid forms of Compound 1 are also suitable for treatment of plant propagation material other than seed, such as fruit, tubers or plant seedlings. The propagation material can be treated with the compounds before planting, or the compounds can be applied to the planting site when the propagation material is being planted.

For agronomic applications, the rate of application required for effective control (i.e. "biologically effective amount") will depend on such factors as the species of nematode to be controlled, the nematode's life cycle, life stage, its size, location, time of year, host crop or animal, feeding behavior, mating behavior, ambient moisture, temperature, and the like. Under normal circumstances, application rates of about 0.01 to 2 kg of active ingredients per hectare are sufficient to control nematodes in agronomic ecosystems, but as little as 0.0001 kg/hectare may be sufficient or as much as 8 kg/hectare may be required. For nonagronomic applications, effective use rates will range from about 1.0 to 50 mg/square meter but as little as 0.1 mg/square meter may be sufficient or as much as 150 mg/square meter may be required. One skilled in the art can easily determine the biologically effective amount necessary for the desired level of parasitic nematode control.

What is claimed is:
1. A polymorph of 8-chloro-N-[(2-chloro-5-methoxyphenyl)sulfonyl]-6-(trifluoromethyl)-imidazo[1,2-a]pyridine-2-carboxamide designated Form A characterized by a room-temperature powder Cu(Kα1) X-ray diffraction pattern having at least the 2θ reflection positions

| 2θ |
|---|
| 30.367 |
| 29.131 |
| 27.995 |
| 27.611 |
| 26.49 |
| 25.973 |
| 25.604 |
| 24.285 |
| 23.582 |
| 19.789. |

2. A polymorph of 8-chloro-N-[(2-chloro-5-methoxyphenyl)sulfonyl]-6-(trifluoromethyl)-imidazo[1,2-a]pyridine-2-carboxamide as a 1 to 1 solvate with toluene designated Form TS characterized by a room-temperature powder Cu(Kα1) X-ray diffraction pattern having at least the 2θ reflection positions

| 2θ |
|---|
| 28.913 |
| 26.942 |
| 25.672 |
| 24.451 |
| 23.316 |
| 22.429 |
| 20.325 |
| 19.053 |
| 18.603 |
| 12.871. |

3. A method for preparing the polymorph Form A of claim 1 comprising forming a slurry with a solvent of one or more solid forms of 8-chloro-N-[(2-chloro-5-methoxyphenyl)sulfonyl]-6-(trifluoromethyl)-imidazo[1,2-a]pyridine-2-carboxamide selected from the group of forms B, C, D, having a powder Cu(Kα1) X-ray diffraction pattern in accordance with that shown in FIG. 1, solvates, amorphous forms and mixtures of any of the foregoing with Form A and maintaining the slurry while the solid forms of 8-chloro-N-[(2-chloro-5-methoxyphenyl)sulfonyl]-6-(trifluoromethyl)-imidazo[1,2-a]pyridine-2-carboxamide convert to polymorph Form A.

4. The method of claim 3 wherein the solid forms of 8-chloro-N-[(2-chloro-5-methoxyphenyl)sulfonyl]-6-(trifluoromethyl)-imidazo[1,2-a]pyridine-2-carboxamide comprises a mixture of polymorphs Form A and Form B.

5. The method of claim 3 wherein the slurry is heated to a temperature between 30° C. and the boiling point of the solvent and agitated.

6. The method of claim 3 wherein the slurry is agitated.

7. The method of claim 3 wherein the solvent comprises water, a $C_5$-$C_8$ alkane, a $C_1$-$C_4$ alkanol or a $C_3$-$C_4$ ketone.

8. The method of claim 7 wherein the solvent comprises water or methanol.

9. A method for preparing the polymorph Form A of claim 1 comprising,
(A) contacting 8-chloro-6-trifluoromethyl-imidazo[1,2-a]pyridine-2-carbonyl chloride or a salt thereof and 2-chloro-5-methoxybenzene sulfonamide in the presence of a first solvent to form a reaction mixture containing an intermediate solid form of 8-chloro-N-[(2-chloro-5-methoxyphenyl)sulfonyl]-6-(trifluoromethyl)-imidazo[1,2-a]pyridine-2-carboxamide,
(B) separating the intermediate solid form of 8-chloro-N-[(2-chloro-5-methoxyphenyl)-sulfonyl]-6-(trifluoromethyl)-imidazo[1,2-a]pyridine-2-carboxamide, and
(C) contacting the intermediate solid form of 8-chloro-N-[(2-chloro-5-methoxyphenyl)sulfonyl]-6-(trifluoromethyl)-imidazo[1,2-a]pyridine-2-carboxamide with a second solvent, optionally heated to a temperature between 30° C. and the boiling point of the second solvent, to convert the intermediate solid form to the polymorph Form A of claim 1.

10. The method of claim 9 wherein the intermediate solid form of 8-chloro-N-[(2-chloro-5-methoxyphenyl)sulfonyl]-6-(trifluoromethyl)-imidazo[1,2-a]pyridine-2-carboxamide is a solvate.

11. The method of claim 10 wherein the intermediate solid form of 8-chloro-N-[(2-chloro-5-methoxyphenyl)sulfonyl]-6-(trifluoromethyl)-imidazo[1,2-a]pyridine-2-carboxamide is a solvate with toluene.

12. The method of claim 9 wherein the intermediate solid form of 8-chloro-N-[(2-chloro-5-methoxyphenyl)sulfonyl]-6-(trifluoromethyl)-imidazo[1,2-a]pyridine-2-carboxamide is an unsolvated polymorph or mixture of polymorphs.

13. The method of claim 9 wherein the first solvent comprises a mixture of toluene with ethyl acetate and the second solvent comprises water, methanol, acetone or n-heptane.

14. A nematocidal composition comprising (a) the polymorph Form A of claim 1 and (b) at least one additional component selected from the group consisting of surfactants, solid diluents and liquid carriers.

15. A nematocidal composition comprising (a) the polymorph Form A of claim 1 and (b) at least one other nematocide, insecticide or fungicide.

16. A method for protecting a plant from nematodes comprising applying to the plant, or portion, or seed thereof, or to the growing medium of the plant, a nematocidally effective amount of 8-chloro-N-[(2-chloro-5-methoxyphenyl)sulfonyl]-6-(trifluoromethyl)-imidazo[1,2-a]pyridine-2-carboxamide comprising the polymorph Form A of claim 1.

17. The nematicidal composition of claim 15 wherein component (b) is selected from: abamectin, acetamiprid, acrinathrin, amitraz, avermectin, azadirachtin, bifenthrin, buprofezin, carbaryl, cartap, chlorantraniliprole, chlorfenapyr, chlorpyrifos, clothianidin, cyantraniliprole, cyfluthrin, beta-cyfluthrin, cyhalothrin, lambda-cyhalothrin, gamma-cyhalothrin, cypermethrin, alpha-cypermethrin, zeta-cypermethrin, cyromazine, deltamethrin, dieldrin, dinotefuran, diofenolan, emamectin, endosulfan, esfenvalerate, ethiprole, etofenprox, etoxazole, fenothiocarb, fenoxycarb, fenvalerate, fipronil, flonicamid, flubendiamide, flufenoxuron, fluvalinate, formetanate, hexaflumuron, hydramethylnon, imidacloprid, indoxacarb, lufenuron, metaflumizone, methiodicarb, methomyl, methoprene, methoxyfenozide, nitenpyram, nithiazine, novaluron, oxamyl, pymetrozine, pyrethrin, pyridaben, pyridalyl, pyriproxyfen, ryanodine, spinetoram, spinosad, spirodiclofen, spiromesifen, spirotetramat, tebufenozide, tetramethrin, thiacloprid, thiamethoxam, thiodicarb, thiosultap-sodium, tralomethrin, triazamate, triflumezopyrim, triflumuron, all strains of *Bacillus thuringiensis* and all strains of *Nucleo polyhedrosis* viruses.

\* \* \* \* \*